(12) United States Patent
Chuang

(10) Patent No.: US 11,016,111 B1
(45) Date of Patent: May 25, 2021

(54) STRIDE MONITORING

(71) Applicant: Thomas Chu-Shan Chuang, San Francisco, CA (US)

(72) Inventor: Thomas Chu-Shan Chuang, San Francisco, CA (US)

( * ) Notice: Subject to any disclaimer, the term of this patent is extended or adjusted under 35 U.S.C. 154(b) by 418 days.

(21) Appl. No.: 13/754,901

(22) Filed: Jan. 31, 2013

Related U.S. Application Data

(60) Provisional application No. 61/593,140, filed on Jan. 31, 2012.

(51) Int. Cl.
*G01P 1/00* (2006.01)
*G06F 17/00* (2019.01)

(52) U.S. Cl.
CPC ............... *G01P 1/00* (2013.01); *G06F 17/00* (2013.01)

(58) Field of Classification Search
CPC ........................................................ G01P 1/00
USPC ........................................................ 702/142
See application file for complete search history.

(56) References Cited

U.S. PATENT DOCUMENTS

| | | | |
|---|---|---|---|
| 4,736,312 A | | 4/1988 | Dassler et al. |
| 4,763,287 A | | 8/1988 | Gerhaeuser et al. |
| 5,586,398 A | | 12/1996 | Carlson |
| 5,689,099 A | | 11/1997 | Domburg |
| 6,018,705 A | * | 1/2000 | Gaudet ................ A61B 5/1121 235/105 |
| 6,145,389 A | * | 11/2000 | Ebeling ................ A61B 5/1038 73/865.4 |
| 6,292,792 B1 | | 9/2001 | Baffes et al. |
| 6,356,856 B1 | * | 3/2002 | Damen ..................... A43B 3/00 482/3 |
| 6,493,652 B1 | * | 12/2002 | Ohlenbusch ......... A61B 5/1038 324/160 |
| 6,611,789 B1 | * | 8/2003 | Darley ................. A61B 5/1038 702/141 |
| 6,876,947 B1 | * | 4/2005 | Darley ................. A43B 3/0005 702/160 |
| 6,882,955 B1 | * | 4/2005 | Ohlenbusch ......... A43B 3/0005 702/160 |
| 6,898,550 B1 | * | 5/2005 | Blackadar et al. ........... 702/182 |
| 7,220,220 B2 | | 5/2007 | Stubbs et al. |
| 7,355,519 B2 | | 4/2008 | Grold et al. |
| 7,467,060 B2 | * | 12/2008 | Kulach et al. ................ 702/141 |
| 7,603,255 B2 | | 10/2009 | Case, Jr. et al. |
| 7,617,071 B2 | | 11/2009 | Darley et al. |
| 7,647,196 B2 | * | 1/2010 | Kahn et al. .................... 702/149 |

(Continued)

OTHER PUBLICATIONS

Brambert et al. "Gait Analysis Using a Shoe-Integrated Wireless Sensor System" IEEE Transactions on Information Technology in Biomedicine, vol. 12, No. 4, Jul. 2008.

(Continued)

*Primary Examiner* — Raymond L Nimox
(74) *Attorney, Agent, or Firm* — Chuang Intellectual Property Law; Thomas Chuang

(57) ABSTRACT

Methods and apparatuses for stride monitoring are disclosed. In one example, a first sensor monitors a first user motion parameter during a user running activity and provides a first sensor output and a second sensor monitors a second user motion parameter during the user running activity and provides a second sensor output. The first sensor output and the second sensor output are processed to determine a user parameter associated with both the first sensor output and the second sensor output.

31 Claims, 25 Drawing Sheets

(56) References Cited

U.S. PATENT DOCUMENTS

| | | | |
|---|---|---|---|
| 7,857,772 B2 | 12/2010 | Bouvier et al. | |
| 8,056,268 B2 | 11/2011 | DiBenedetto et al. | |
| 8,070,654 B2 | 12/2011 | Chapa, Jr. et al. | |
| 8,128,410 B2 | 3/2012 | Prstojevich | |
| 8,480,541 B1* | 7/2013 | Brunts | A63B 22/0242 482/1 |
| 2002/0019296 A1 | 2/2002 | Freeman et al. | |
| 2002/0099516 A1* | 7/2002 | Guzman | A43B 1/0036 702/160 |
| 2004/0102931 A1* | 5/2004 | Ellis | A61B 5/1038 702/188 |
| 2001/0122483 | 6/2004 | Nathan et al. | |
| 2005/0184878 A1* | 8/2005 | Grold | A43B 3/0005 340/573.7 |
| 2007/0123806 A1 | 5/2007 | Bouvier et al. | |
| 2007/0202478 A1 | 8/2007 | Al-Obaidi et al. | |
| 2007/0203665 A1 | 8/2007 | Darley et al. | |
| 2007/0208544 A1* | 9/2007 | Kulach | A61B 5/112 702/189 |
| 2007/0272011 A1 | 11/2007 | Chapa, Jr. et al. | |
| 2008/0146968 A1 | 6/2008 | Hanawaka et al. | |
| 2008/0190202 A1* | 8/2008 | Kulach | A63B 24/0062 73/514.01 |
| 2008/0214360 A1* | 9/2008 | Stirling | A61B 5/1038 482/9 |
| 2008/0249736 A1 | 10/2008 | Prstojevich | |
| 2009/0043531 A1* | 2/2009 | Kahn | A61B 5/0022 702/149 |
| 2009/0047645 A1* | 2/2009 | Dibenedetto | G16H 15/00 434/258 |
| 2009/0233770 A1* | 9/2009 | Vincent | A63B 24/0021 482/8 |
| 2010/0260011 A1 | 10/2010 | Berger et al. | |
| 2011/0003665 A1 | 1/2011 | Burton et al. | |
| 2011/0022349 A1* | 1/2011 | Stirling | A61B 5/1038 702/141 |
| 2011/0054809 A1* | 3/2011 | Templeman | A61B 5/1118 702/44 |
| 2011/0184225 A1* | 7/2011 | Whitall | A63B 24/0003 600/28 |
| 2012/0035509 A1 | 2/2012 | Wilson et al. | |
| 2013/0053990 A1* | 2/2013 | Ackland | G06Q 30/02 700/91 |

OTHER PUBLICATIONS

Chen, et al. "Intelligent Shoes for Abnormal Gait Detection". 2008 IEEE International Conference on Robotics and Automation Pasadena, CA, USA, May 19-23, 2008.

Morris Rick, "Overstriding and how to correct it" May 31, 2009.

Morris, et al. Shoe Integrated Sensor System for Wireless Gait Analysis and Real time feedback. Oct. 23-26, 2012.

\* cited by examiner

1500

| Split | Average Pace | Average Stride Rate |
|---|---|---|
| 1 | 8:26 | 78 |
| 2 | 8:26 | 78 |
| 3 | 7:45 | 82 |
| 4 | 7:45 | 81 |
| 5 | 7:20 | 83 |
| 6 | 6:50 | 87 |
| 7 | 7:20 | 84 |
| 8 | 6:55 | 88 |
| 9 | 6:50 | 88 |
| 10 | 6:50 | 88 |
| 11 | 6:55 | 88 |
| 12 | 7:20 | 83 |
| 13 | 7:20 | 82 |
| 14 | 8:26 | 77 |
| 15 | 8:26 | 78 |

| Average Pace | Average Stride Rate |
|---|---|
| 6:50 | 87.67 |
| 6:55 | 88 |
| 7:20 | 82.67 |
| 7:45 | 81.5 |
| 8:26 | 77.75 |

| Split | Average Pace | Average Stride Rate |
|---|---|---|
| 1 | 8:05 | 83 |
| 2 | 8:04 | 83 |
| 3 | 8:26 | 80 |
| 4 | 8:26 | 80 |
| 5 | 7:50 | 84 |
| 6 | 7:45 | 84 |
| 7 | 8:26 | 79 |
| 8 | 7:45 | 84 |
| 9 | 6:50 | 90 |
| 10 | 6:51 | 90 |
| 11 | 6:50 | 90 |
| 12 | 6:50 | 90 |

| Average Pace | Average Stride Rate |
|---|---|
| 6:50 | 90 |
| 6:51 | 90 |
| 7:45 | 84 |
| 7:50 | 84 |
| 8:04 | 83 |
| 8:05 | 83 |
| 8:26 | 79.67 |

| Average Pace | 1st Run | 2nd Run |
|---|---|---|
| 6:50 | 87.67 | 90 |
| 7:45 | 81.5 | 84 |
| 8:26 | 77.75 | 79.67 |

FIG. 19

STRIDE MONITORING

CROSS REFERENCE TO RELATED APPLICATIONS

This application claims priority to Provisional Patent Application No. 61/593,140, entitled "Stride Monitoring," to Thomas C. Chuang, and filed Jan. 31, 2012, the entire disclosure of which is incorporated herein by reference for all purposes.

This application is related to patent application Ser. No. 13/431,744, entitled "Athletic Performance Monitoring with Overstride Detection", to Thomas C. Chuang, and filed Mar. 27, 2012, claiming priority to Provisional Patent Application No. 61/475,635, entitled "Athletic Performance Monitoring with Overstride Detection," to Thomas C. Chuang, and filed Apr. 14, 2011, and patent application Ser. No. 13/431,789, entitled "Athletic Performance Monitoring with Overstride Detection", to Thomas C. Chuang, and filed Mar. 27, 2012, claiming priority to Provisional Patent Application No. 61/475,635, entitled "Athletic Performance Monitoring with Overstride Detection," to Thomas C. Chuang, and filed Apr. 14, 2011.

BACKGROUND OF THE INVENTION

Good running form is essential for a runner to achieve his or her best results as well as minimize the occurrence of injury. A runner's stride is the critical component to good form, and development of a proper stride should be sought by runners of all abilities.

As a result, methods and apparatuses for monitoring runner stride are needed.

BRIEF DESCRIPTION OF THE DRAWINGS

The present invention will be readily understood by the following detailed description in conjunction with the accompanying drawings, wherein like reference numerals designate like structural elements.

FIG. 15 illustrates a table having split, average page, and average run cadence data for a first run performed by a user.

FIG. 16 illustrates a table where the data shown in FIG. 15 has been processed to show a use stride rate as a function of speed (e.g., pace).

FIG. 17 illustrates a table having split, average page, and average run cadence data for a second run performed by a user.

FIG. 18 illustrates a table where the data shown in FIG. 17 has been processed to show a use stride rate as a function of speed (e.g., pace).

FIG. 19 illustrates a table where the data in FIG. 16 and FIG. 18 has been processed to show changes in stride rate from the first run to the second run based on a same average pace.

DESCRIPTION OF SPECIFIC EMBODIMENTS

Figure 1:
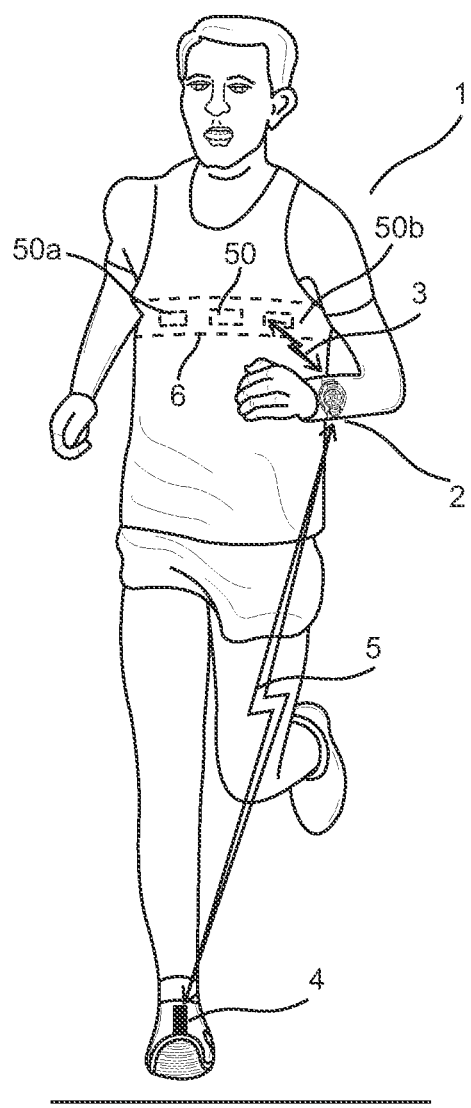
FIG. 1 illustrates a system for athletic performance monitoring being worn by a runner in one example.

Methods and apparatuses for athletic performance monitoring are disclosed. The following description is presented to enable any person skilled in the art to make and use the invention. Descriptions of specific embodiments and applications are provided only as examples and various modifications will be readily apparent to those skilled in the art. The general principles defined herein may be applied to other embodiments and applications without departing from the spirit and scope of the invention. Thus, the present invention is to be accorded the widest scope encompassing numerous alternatives, modifications and equivalents consistent with the principles and features disclosed herein. For purpose of clarity, details relating to technical material that is known in the technical fields related to the invention have not been described in detail so as not to unnecessarily obscure the present invention.

In one example, a system for athletic training includes a first inertial foot sensor operable for coupling to a first portion of a user foot and configured to generate a first output signal corresponding to a first portion motion, the first portion motion comprising a rearward upward kick and a forward motion in the air in a direction of locomotion. The system includes a second inertial foot sensor operable for coupling to a second portion of the user foot and configured to generate a second output signal corresponding to a second portion motion, the second portion motion comprising a rearward upward kick and a forward motion in the air in the direction of locomotion. The system further includes a processing system configured to compare the first output signal corresponding to the first portion motion to the second output signal corresponding to the second portion motion. In one example, the processing system is configured to compare the first output signal corresponding to the first portion motion to the second output signal corresponding to the second portion motion to identify a reduction in user overstride. In one example, the first inertial sensor includes a first accelerometer and the second inertial sensor includes a second accelerometer. In one example, the processing system is further configured to process the first output signal and process the second output signal to identify a user overstride during running. The user speed or distance travelled may also be identified. In one example, the processing system is further configured to determine a percentage of user strides which are overstrides over a given time period. In one example, the system further includes a user interface in communication with the processing system, the user interface configured to output an alert if the percentage of user overstrides exceeds a tolerance. In one example, the system further includes a user interface in communication with the processing system, the user interface configured to output a vibrate indication, visual indication or an audible indication of the user overstride. In one example, the system is further configured to analyze the first output signal corresponding to the first portion motion and the second output signal corresponding to the second portion motion to identify a user stride improvement.

In one example, a method includes generating a first inertial foot sensor output signal responsive to a motion of a first portion of a user foot, the motion comprising a takeoff rearward upward kick and a forward motion in the air in a direction of locomotion. The method includes generating a second inertial foot sensor output signal responsive to a motion of a second portion of the user foot, the motion comprising a takeoff rearward upward kick and a forward motion in the air in the direction of locomotion. The method further includes comparing the first inertial foot sensor output signal and the second inertial foot sensor output signal.

In one example, a system includes a first foot sensor configured to output a first signal responsive to a takeoff rearward kick and a landing of a first portion of an athlete foot in a direction of locomotion. The system includes a second foot sensor configured to output a second signal responsive to a takeoff rearward kick and a landing of a second portion of the athlete foot in the direction of locomotion. The system further includes a processing system configured to analyze the first sensor output signal and the second sensor output signal to identify a user overstride. In one example, the first foot sensor includes a first inertial sensor and the second foot sensor includes a second inertial sensor. For example, the first sensor includes a first accelerometer and the second sensor includes a second accelerometer. In one example, the processing system is configured to identify a user overstride by determining a landing of the athlete foot relative to an athlete center of gravity. In one example, the first foot sensor is a pressure sensor and the second foot sensor is a pressure sensor. In yet another example, the first foot sensor is an inertial sensor and the second foot sensor is a pressure sensor. In one implementation, this last embodiment is advantageous as the pressure sensor can be built into a shoe and shipped with the shoe and the inertial sensor can be added on by the user at a later time. The inertial sensor can be worn on the laces or be worn in a compartment in the shoe as provided by certain manufacturers. This combination allows for the user of a lower cost pressure sensor as one of the sensors while offering the advantages of utilizing an inertial sensor as the second sensor, which allows for detection of speed and other more complex motion factors.

In one example, a method includes generating a first sensor output signal responsive to a takeoff rearward kick of an athlete foot and a landing of a first portion of the athlete foot in a direction of locomotion. The method includes generating a second sensor output signal responsive to a takeoff rearward kick of the athlete foot and a landing of a second portion of the athlete foot in the direction of locomotion. The method further includes analyzing the first sensor output signal and the second sensor output signal to identify a user overstride. In one example, the first sensor output signal is a first accelerometer output signal and the second sensor output signal is a second accelerometer output signal. In one example, the method further includes determining a percentage of user strides which are overstrides over a given time period. In one example, analyzing the first sensor output signal and the second sensor output signal to identify a user overstride includes comparing the first sensor output signal and the second sensor output signal to stored motion profiles. In one example, the method further includes processing the first sensor output signal or the second sensor output signal to determine a user speed or distance travelled. In one example, the method further includes analyzing the first sensor output signal and the second sensor output signal to identify a reduction in user overstride (i.e., an improved user stride).

In one example, a system includes a first acceleration sensor configured to measure a first acceleration in a moving direction of a first portion of a foot during locomotion and outputting a first acceleration signal responsive to the first acceleration. The system includes a second acceleration sensor configured to measure a second acceleration in a moving direction of a second portion of a foot during locomotion and outputting a second acceleration signal responsive to the second acceleration. The system further includes a processing system configured to process the first acceleration signal and the second acceleration signal to identify a user overstride. In one example, the processing system identifies a difference in motion between the first portion and the second portion. In one example, the processing system is operable to receive and process the first acceleration signal to produce a first measured motion profile and receive and process the second acceleration signal to produce a second measured motion profile, wherein the processing system is configured to utilize the first measured motion profile and the second measured motion profile in comparison with pre-stored motion profiles to identify a user overstride.

In one example, a system includes an acceleration sensor configured to measure an acceleration in a moving direction of a user foot during locomotion and output an acceleration signal responsive to the acceleration. The system includes a memory storing an overstride acceleration motion profile associated with a user overstride. The system further includes a processing system configured to process the first acceleration signal to produce a measured motion profile and compare with the overstride acceleration motion profile to identify a user overstride.

In one example, the memory further stores a plurality of acceleration motion profiles associated with user stride motions, and wherein the processing system matches the measured motion profile with an acceleration motion profile in the plurality of acceleration motion profiles to identify a user stride motion.

In one example, the accelerometer is configured to be disposed at a midfoot region of a user foot during operation. In this example, by placing the accelerometer at the midfoot, a direct mid-foot landing on the user midfoot during a desired running motion will maximize the amplitude of the accelerometer output signal, thereby making it easier to distinguish from a heel first landing and determine whether the user is running with a desirable stride motion.

In one example, an athletic performance monitoring system includes a first foot worn device configured to be worn on a first foot portion, including a first sensor configured to output first sensor data associated with movement of the first foot portion. The system includes a second foot worn device configured to be worn on a second foot portion, including a second sensor configured to output second sensor data associated with movement of the second foot portion. The system further includes a wrist worn device configured to be worn device worn an arm of a person, including a processing system comprising a processor configured to receive the first sensor data and the second sensor data and identify a user overstride motion. The system further includes a user interface such as a display and audio output.

In one example, the first sensor includes a first accelerometer and the second sensor includes a second accelerometer. In one example, the first foot worn device further includes a first wireless transceiver and the second foot worn device further includes a second wireless transceiver.

In one example, a method for detecting user stride motion includes prompting a user to run with an overstride stride motion during an overstride time period, receiving a sensor output signal during the overstride time period, and processing the sensor output signal to generate an overstride motion profile. The method further includes prompting the user to run with a goal stride motion during a goal time period, receiving a sensor output signal during the goal time period, processing the sensor output signal to generate a goal motion profile, receiving a sensor output signal during a user running activity, processing the sensor output signal to generate a running activity motion profile, and matching the running activity motion profile to the overstride motion profile or the goal motion profile.

In one example, prompting the user to run with a goal stride motion during a goal time period includes instructing the user to run with a hips-forward body position during running. In one example, prompting the user to run with a goal stride motion during a goal time period includes instructing the user to run with a high step cadence during running. In one example, prompting the user to run with a goal stride motion during a goal time period includes instructing the user to run with decreased stride length during running. In one example, prompting the user to run with a goal stride motion during a goal time period includes instructing the user to maintain a bent knee during running. In one example, prompting a user to run with an overstride stride motion includes instructing the user to run with a hips-back or seated position during running.

In one example, a system includes an inertial sensor configured to measure an acceleration in a moving direction of a user foot of a user during locomotion and output an acceleration signal responsive to the acceleration, a memory storing a stride acceleration motion profile, and a processing system configured to process the acceleration signal and the stride acceleration motion profile to determine a user stride improvement. In one example, the stride improvement is relative to a prior locomotion by the user.

In one example, a system includes an inertial sensor configured to measure an acceleration in a moving direction of a user foot of a user during locomotion and output an acceleration signal responsive to the acceleration, a memory storing an undesired stride acceleration motion profile, and a processing system configured to process the acceleration signal and the undesired stride acceleration motion profile to identify a reduced user overstride. In one example, the undesired stride acceleration motion profile is generated from a prior locomotion by the user. In one example, the undesired stride acceleration motion profile corresponds to a normal running motion of the user. In one example, the processing system processes the acceleration signal to calculate an average cadence and an average stride length for a same speed. In one example, the memory further stores a plurality of acceleration motion profiles associated with the user, and wherein the processing system matches the acceleration signal with an acceleration motion profile in the plurality of acceleration motion profiles to identify a user stride motion. In one example, the memory further stores a goal stride acceleration motion profile generated from a prior locomotion by the user. For example, the goal stride acceleration motion profile is generated responsive to a user prompt instructing the user to run with a goal stride motion.

In one example, a system for athletic training includes a first body sensor such as an inertial sensor operable for coupling with a user foot or leg (either directly or via a shoe or article of clothing, etc.) and oriented relative to a user foot motion direction to generate a first output signal corresponding to the user foot motion and a second body sensor such as an inertial sensor operable for coupling with a user arm and oriented relative to a user arm motion direction to generate a second output signal corresponding to the user arm motion. The system includes a processing system configured to analyze the first output signal to identify a first motion condition when the user foot motion includes a forward motion and analyze the second output signal to identify a second motion condition when the user arm motion includes a forward motion, the processing system further configured to output a synchronization parameter utilizing the first motion condition and the second motion condition. In one example, the first inertial sensor includes a first accelerometer and the second inertial sensor includes a second accelerometer.

A system for athletic training includes a first inertial sensor operable for coupling with a user foot, the first inertial sensor oriented relative to a user foot motion to generate a first output signal corresponding to the user foot motion, and a second inertial sensor operable for coupling with an opposite side user arm on a body side opposite the user foot, the second inertial sensor oriented relative to an opposite side user arm motion to generate a second output signal corresponding to the opposite side user arm motion. The system includes a processing system in communication with the first inertial sensor and the second inertial sensor, the processing system configured to analyze the first output signal to estimate a foot direction parameter and the analyze the second output signal to estimate an opposite side user arm direction parameter, the processing system further configured to generate a synchronization parameter associated with a degree to which the foot direction parameter matches the opposite side user arm direction parameter.

In one example, the system further includes a user interface in communication with the processing system, the user interface configured to output a visual indication or an audible indication of the synchronization parameter. In one example, the system further includes a first housing adapted to house the first initial sensor and the second housing adapted to house the second inertial sensor and the processing system.

A method for monitoring athletic activity includes measuring with a first acceleration sensor a first acceleration in a moving direction of a foot of an athlete and outputting a first acceleration signal responsive to the first acceleration, processing the first acceleration signal to identify a moving direction component of the foot substantially parallel to a surface beneath the athlete, and measuring with a second acceleration sensor a second acceleration in a moving direction of an arm of an athlete and outputting a second acceleration signal responsive to the second acceleration. The method further includes processing the second acceleration signal to identify a moving direction component of the arm substantially parallel to a surface beneath the athlete, and comparing the moving direction component of the foot to the moving direction component of the arm to determine a degree of synchronization between the foot and the arm.

In one example, the moving direction component of the foot substantially parallel to a surface beneath the athlete includes a forward facing direction and the moving direction component of the arm substantially parallel to a surface beneath the athlete includes the forward facing direction. In one example, the degree of synchronization between the foot and the arm is between an opposing arm and leg on different sides of the athlete body. In one example, the degree of synchronization between the foot (i.e., the first accelerometer) and the arm (i.e., the second accelerometer) is associated with the extent to which both the arm and the foot are simultaneously moving together in a forward direction. In one example, a series of audible tones are output when the degree of synchronization is high, where each audible tone is associated with a simultaneous movement of both the arm and the foot of the athlete during a running motion. In one example, an audible alarm is output when the degree of synchronization is low.

A system for monitoring athletic activity includes a first acceleration sensor configured to measure a first acceleration in a moving direction of a foot of an athlete and output a first acceleration signal responsive to the first acceleration, and a second acceleration sensor configured to measure a second acceleration in a moving direction of an arm of an athlete and output a second acceleration signal responsive to the second acceleration. The system includes a processor configured to process the first acceleration signal to identify a moving direction component of the foot substantially parallel to a surface beneath the athlete and process the second acceleration signal to identify a moving direction component of the arm substantially parallel to a surface beneath the athlete. The processor is further configured to compare the moving direction component of the foot to the moving direction component of the arm to determine a degree of synchronization between the foot and the arm.

A method for analyzing activity of an athlete includes generating a first sensor output signal responsive to forward movement of an athlete foot in a stepping direction, and generating a second sensor output signal responsive to a forward movement of an opposite athlete arm, the opposite athlete arm on a body side opposite the athlete foot. The method includes analyzing the first sensor output signal and the second sensor output signal to identify whether the athlete foot and the opposite athlete arm forward movement are substantially synchronized. In one example, the forward movement of an athlete foot and the forward movement of an opposite athlete arm are associated with movement during running activity.

A system for analyzing activity of an athlete includes a first sensor configured to generate a first sensor output signal responsive to forward movement of an athlete foot in a stepping direction, a second sensor configured to generate a second sensor output signal responsive to a forward movement of an opposite athlete arm, the opposite athlete arm on a body side opposite the athlete foot, and a processor configured to analyze the first sensor output signal and the second sensor output signal to identify whether the athlete foot and the opposite athlete arm forward movement are substantially synchronized.

A system for analyzing activity of a person running in a forward direction on a surface includes a first sensor to be supported in relation to a foot of the person, the first sensor configured and arranged to output a first sensor output signal in response to movement of the foot during running, and a second sensor to be supported in relation to an arm of the person, the second sensor configured and arranged to output a second sensor output signal in response to movement of the arm during running. The system includes a processor configured to receive and analyze the first sensor output signal and the second sensor output signal to determine a degree of synchronization between the foot and the arm in the forward direction.

A system for body motion sensing includes a first motion sensor operable to measure first sensor data on motion of a first body part, and a second motion sensor operable to measure second sensor data on motion of a second body part. The system includes a processor in communication with the first motion sensor and the second motion sensor to receive and process the first sensor data and the second sensor data to produce a first measured motion profile and a second measured motion profile, where the processor is configured to compare the first measured motion profile and the second measured motion profile to produce an indicator signal indicating a deviation of the first measured motion profile from the second measured motion profile with respect to a motion directional component. The processing may occur in real time as the $1^{st}$ and $2^{nd}$ sensor data is being received. In one example, the system further includes a user interface configured to output an alert signal responsive to the indicator signal indicating the deviation exceeds a tolerance range. In one example, the motion sensor is a tri-axial accelerometer.

An athletic performance monitoring system includes a leg worn device configured to be worn on a leg of a person. The leg worn device includes a first inertial sensor configured to output first sensor data associated with movement of the leg, and a first wireless transceiver. The athletic performance monitoring system includes a wrist worn device configured to be worn device worn an arm of a person on a body side opposite the leg worn device. The wrist worn device includes a second inertial sensor configured to output second sensor data associated with movement of the arm, a second wireless transceiver operable for communication with the first wireless transceiver, a user interface, and a processing system. The processing system includes a processor configured to receive the first sensor data and the second sensor data and determine a degree of synchronization between the leg and the arm. In one example, the degree of synchronization is based upon whether the extent to which the arm and leg are simultaneously moving in a forward direction. In one example, the leg worn device and the wrist worn device are synchronized in time.

In one example, the user interface is configured to output an indication responsive to the degree of synchronization between the leg and the arm. For example, the indication output by the user interface includes a series of audible tones when the degree of synchronization is in a high state, wherein a tone is output for each forward motion of the arm and the leg substantially together.

In one example, the processing system is further configured to generate an audible rhythm assist tool, the audible rhythm assist tool output at the user interface. In one example, the audible rhythm assist tool includes an audible tone output for each forward motion of the arm and the leg substantially together.

FIG. 1 illustrates a system for athletic performance monitoring being worn by a walker or runner 1 in one example. FIG. 1 shows a walking or running person 1 wearing a sensor unit 2 around his wrist and wearing athletic shoes to which a sensor unit 4 is attached. However, the sensor unit 4 may also be incorporated in the sole of the shoe or elsewhere on or within the shoe. The sensor unit 4 may also be attached directly to the foot of the person. The person 1 is also wearing a sensor unit 6 around his torso.

Sensor units 2, 4, and 6 are placed on or attached to person 1 directly or indirectly. For example, sensor units 2, 4, and 6 may be attached to or on, placed within, or otherwise integrated with worn shoes, accessories, clothing, or equipment. Sensor units 2, 4, and 6 may be mounted directly on runner 1 by adhesives, bands, straps, hooks, other mechanical connectors.

In some examples, the sensor unit 2 may be attached to the user's wrist in an enclosure which is similar to a watch and combined with other functionality such as timekeeping or with other sensors such the navigation device. In further examples, the sensor unit 2 may be attached to the user's arm using an enclosure similar to an armband and combined with other devices such as a cellular phone, an audio device and/or the navigation device.

In some examples, the sensor unit 4 may be attached to the top of a user's shoe with removable fasteners such as clips. In other examples, the sensor unit 4 may be inserted within the user's shoe, such as within a recess formed in the sole of the shoe.

In one example, the sensor unit 6 includes one or more sensors 50 (e.g., accelerometers) or other inertial sensors and may be attached to the user with a chest strap in an enclosure which may include other sensors such as a heart-rate monitor (HRM) sensor. In the example shown in FIG. 1, sensor unit 6 includes sensors 50a and 50b which are triaxial accelerometers mounted in parallel on both the left and right side of the runner 1 torso.

In further examples, the sensor unit 6 may be attached to the user's waist using a belt, clip, or other means. In one example, one of the sensors 50 is oriented in sensor unit 6 so that the vertical displacement of the user torso (i.e., along an axis running between the user foot and head) is monitored with each stride. In one example, this vertical displacement (i.e., the variation in height off of the running surface) of the user torso is compared to the stride length to generate a vertical displacement/horizontal displacement ratio. Advantageously, utilizing a torso mounted accelerometer reduces the complexity of calculating the vertical displacement of the user relative to a foot mounted sensor as the user torso does not move in a rearward direction at any time during striding. The vertical displacement/horizontal displacement ratio may be utilized to determine whether the user is undesirably exerting unnecessary energy in a vertical upwards direction for a given horizontal displacement. In a further example, the vertical displacement may be compared to a horizontal velocity or horizontal acceleration. In a further example, a vertical acceleration/horizontal acceleration ratio is calculated.

For example, if the vertical displacement/horizontal displacement ratio exceeds a predetermined threshold value, an audible alarm may be output to the user. In one example, the threshold value is specific to the user. For example, the system including sensor unit 4 and sensor unit 6 may enter a learning/teaching mode whereby the user runs in the desired form for a test interval and the target vertical displacement/horizontal displacement ratio is measured. For example, during the learning mode, the runner may focus on avoiding unnecessary excess vertical displacement or vertical acceleration. In a further example, the threshold ratio value is determined using test measurements of other runners or established norms and stored by the system prior to use by the runner.

In a further example, the measured motion parameter utilized is the vertical displacement by itself. For example, if the vertical displacement exceeds a predetermined threshold value, an audible alarm may be output to the user. In one example, the threshold value is specific to the user. For example, the system including sensor unit 6 may enter a learning mode whereby the user runs in the desired form for a test interval and the target vertical displacement is measured. In a further example, the threshold value is determined using test measurements of other runners or using established norms and stored by the system prior to use by the runner. In yet another example, the threshold value is set to a specific amount. For example, the threshold value may be set to approximately between 2 to 4 inches. In yet another example, the threshold value is adjusted in real-time based upon the speed of the user. For example, as the speed of the user increases while running, the threshold value may be adjusted in an upward direction. As the speed of the user decreases while running, the threshold value may be adjusted in a downward direction. As described elsewhere herein, threshold values may be set or determined in a variety of ways, including a learning mode whereby values are set specific to the user and/or preset during manufacturing based on tests of other runners, such as elite runners known to perform at high levels, or based on theoretical calculations.

In one example, the vertical threshold is adjusted upward as the user increases speed in the direction of locomotion and adjusted downward as the user decreases speed. Again, the amount of adjustment maybe set/calibrated specific to the user based on the learning mode tests at different speeds and/or pre-set during manufacturing. The average vertical displacement/horizontal displacement ratio or the average vertical displacement over a given time or distance interval may be calculated and output to the user in real time or during subsequent workout analysis.

Sensor units 2, 4, and 6 are operable to sense data associated with the athletic performance such as physical or physiological data. For example, sensor unit 4 may output a signal which is processed to determine step count, step impact, velocity, jump height, distance and other data associated with walking and running activities.

Sensor unit 2 may output a signal which is processed to determine arm motion of runner 1. Sensor unit 2 may also be operable to sense global positioning system (GPS) data, such as location and altitude data. Sensor unit 6 may also monitor time data. Sensor unit 6 may include sensors operable to sense heart rate, temperature and movement in the horizontal and vertical direction.

In further examples, any number of sensors may be provided to sense any desired type of athletic performance information. Furthermore, as used herein, the term "sensor" may refer to one or more sensors. Sensor of varying types may be placed at the same desired location on runner 1. For example, sensor unit 2 may include both an inertial sensor and a GPS locator. Sensor unit 6 may include both an inertial sensor and a heart rate sensor.

Sensor units 2, 4, and 6 are operable to communicate wirelessly amongst themselves. In the example shown in FIG. 1, sensor unit 6 is in communication with sensor unit 2 via a wireless link 3 and sensor unit 4 is in communication with sensor unit 2 via a wireless link 5.

Sensor unit 2 may also be configured to communicate with computing devices, exercise devices, navigation devices, sensors, and any other enabled devices through a communication network, such as a local area network, a wide area network, or the Internet. Such communication may occur via wired or wireless links.

In the example shown in FIG. 1, sensor unit 2 for has been incorporated into a wrist-worn device. For example, wrist worn device may assume a watch form factor having some form of visual display and audio output. Data collected by sensor unit 4 and sensor unit 6 are transmitted to sensor unit 2 (i.e., the wrist worn device) for processing and/or output together with data collected by sensor unit 2. The collected sensor data is processed, stored, and/or displayed at sensor unit 2.

In a further example, data collected by sensor units 2, 4, and 6 are transmitted to an electronic device for processing, where the electronic device need not itself have a sensor. For example, the electronic device may be an MP3 or other type of digital music player, watch, handheld computing device, cellular telephone, or any other device capable of displaying information or outputting audio. The electronic device may process the received sensor data and output associated information to the user via a user interface output such as a LCD display. The electronic device may be attached to the runner's body in any manner similar to that of a sensor so that it is easily carried, moved, heard, or viewed during running. Utilizing the user interface 7, real-time feedback is provided as to the user's arm/opposite leg synchronization, arm rotation across the torso, and vertical/horizontal displacement ratio.

Figure 2:
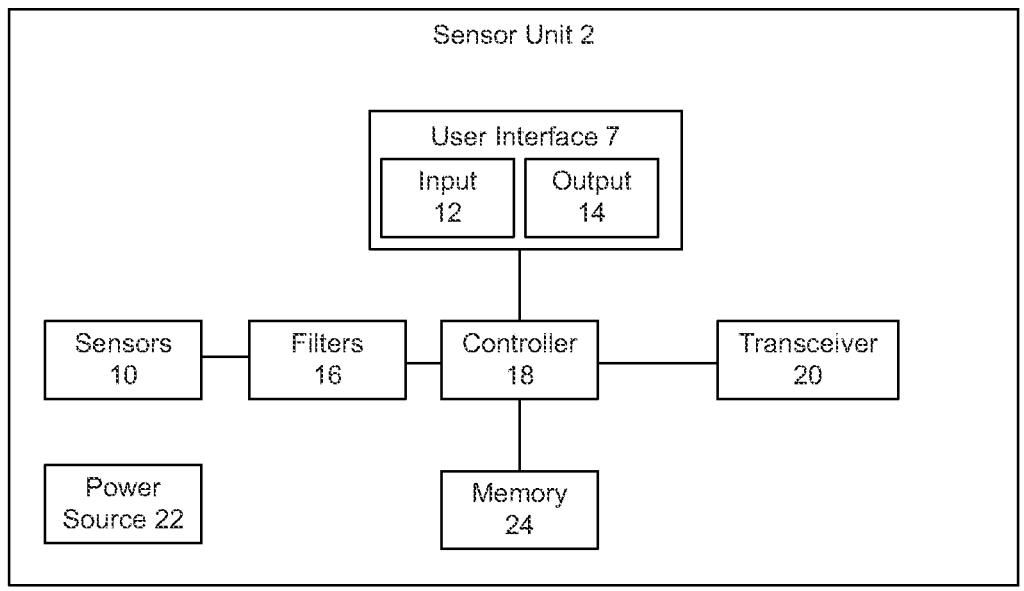
FIG. 2 illustrates a simplified block diagram of a wrist worn component of the system shown in FIG. 1.

FIG. 2 illustrates a simplified block diagram of a wrist worn component, sensor unit 2, of the system shown in FIG. 1. Although shown worn on the wrist, sensor unit 2 may be worn on the user's forearm or arm in further examples. Sensor unit 2 includes a user interface 7. User interface 7 includes an input device 12 and an output device 14. For example, input device 12 may be one or more buttons, switches, a touch bezel, or a touch screen.

Output device 14 may include speakers for outputting audio and a visual display screen. The output device 14 may also include a vibrate element to notify users of information via mechanical vibration. Although shown integrated with sensors 10 within sensor unit 2, in further examples, the user interface 7 can be positioned separately from any sensor devices. The user interface 7 may also include various processing and memory devices to facilitate its functionality. The user interface 7 is operable to receive inputs from the user to control the functionality of the sensor unit 2 and elements associated therewith.

Output device 14 enables users to receive real-time feedback concerning the estimated motion parameter and associated information. For instance, the user interface 7 may present the currently estimated motion parameter, such as degree of synchronization between the user arm and opposite user leg, current stride speed and distance, and/or information associated therewith or with other motion parameters, such as total distance or combinations thereof.

In various examples, the user may configure the sensor unit 2 utilizing the user interface 7 to monitor estimated motion parameters and alert the user through the output device 14 when one or more estimated motion parameters either fall within or fall outside a user-defined condition such as an acceptable parameter range, threshold, or variance.

Sensor unit 2 includes one or more sensors 10. In one example, sensors 10 include one or more accelerometers. In one example, the accelerometer is a tri-axial accelerometer. In one example, the one or more accelerometers are linear accelerometers. In a further example, sensors 10 include a gyroscope in addition to an accelerometer.

Sensor unit 2 also includes filters 16, controller 18, transceiver 20, power source 22, and memory 24. Controller 18 may include one or more signal processors. In one example, power source 22 is a battery, which may be rechargeable or not rechargeable.

Memory 24 may include any computer-readable memory or combination of computer-readable memories operable to store data for use by the controller 18. For instance, the memory may be operable to store acceleration data, motion parameter metric data, statistical data, motion parameter data, filtering data, configuration data, or any combination thereof.

The sensors 10, filters 16, and controller 18 may be integrated together or form discrete elements that may be associated with each other. The controller 18 is operable to analyze measurements provided by the sensors 10 to estimate parameters corresponding to one or more parameter types.

Controller 18 and its included processors are generally operable to couple with the one or more sensors 10 to estimate a motion parameter corresponding to a motion parameter type. The controller 18 may include various analog and digital components operable to perform the various functions discussed herein. For example, the controller 18 may include a microprocessor, a microcontroller, a programmable logic device, digital and analog logic devices.

The controller 18 additionally utilizes information acquired from sensors other than the one or more sensors 10 via wireless links using transceiver 20 to enable real-time comparison of information generated by various sensors in the system. For example, the controller 18 receives information from sensor unit 4 and sensor unit 6 to generate one or more motion parameters using such information.

Similarly, the controller 18 may couple with other sensors to acquire any type of information, For example, to acquire additional information, the controller may couple with, and/or include, gyroscopes, altimeters, compasses, and pressure sensors, and other inertial sensors, or any combination thereof, disposed at sensor unit 2, 4, 6, or elsewhere.

Utilizing various signal processing algorithms, the controller 18 may analyze and compare measurements provided by sensors 10, sensors 40, and sensors at sensor unit 6. For example, by identifying and/or comparing the minimum(s), maximum(s), period, frequency, waveform, rate of change, combinations thereof, and the like, the processing system 16 may process the acceleration signatures to determine one or more motion parameters. Controllers at each sensor unit 4 and 6 may implement similar signal processing algorithms.

In a further example, sensor unit 2 includes a navigation device adapted to provide geographic location information.

The navigation device 24 may include a GPS receiver or may use cellular or other positioning signals instead of the GPS to determine geographic position and generate navigation information. For example, the navigation device is operable to determine speed, current and previous locations, bearing and heading, and altitude. In further examples, the various components of the sensor unit 2 may be housed integrally or separately in any combination.

In one example, undesirable arm swing in a circular direction across the front of the user torso (as opposed to the desirable swing direction maintained back and forth along an axis or plane defined by the direction of movement) is measured with two accelerometers, a triaxial accelerometer, or a gyroscope housed within sensor unit 2. In one example, measured translational accelerations are used to compute angular acceleration which can be doubly integrated to obtain the amount of arm swing in a plane substantially perpendicular to the direction of travel.

Figure 3A:
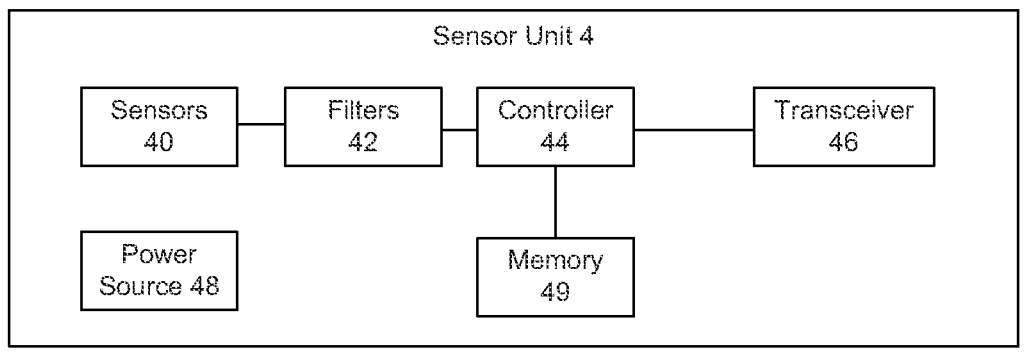
FIG. 3A illustrates a simplified block diagram of a foot mounted component of the system shown in FIG. 1.

FIG. 3A illustrates a simplified block diagram of a foot mounted component, sensor unit 4, of the system shown in FIG. 1. Sensor unit 4 includes sensors 40, filters 42, controller 44, transceiver 46, power source 48, and memory 49. Controller 44 may include one or more signal processors. In one example, power source 48 is a battery.

Sensor unit 4 includes one or more sensors 40. In one example, sensors 40 include one or more accelerometers. In a further example, sensors 40 include a gyroscope in addition to an accelerometer. In one example, the accelerometer is a tri-axial accelerometer. In one example, the one or more accelerometers are linear accelerometers.

The sensors 40, filters 42, and controller 44 may be integrated together or form discrete elements that may be associated with each other. The controller 44 is operable to analyze measurements provided by the sensors 40 to estimate parameters corresponding to one or more parameter types.

The one or more sensors 10 and 40 are each operable to measure an acceleration and generate an acceleration measurement corresponding to the measured acceleration. The acceleration measurement may be embodied as a signal operable to be utilized by the filters 16 and 42 and/or controllers 18 and 44.

In some embodiments, one or more of the sensors 10 and 40 may be operable to output an analog signal corresponding to an acceleration measurement. For instance, each accelerometer may output an analog voltage signal that is proportional to measured accelerations.

However, the one or more sensors 10 and 40 may include any digital and analog components operable to generate a signal corresponding to a measured acceleration. Thus, in some embodiments, one or more of the sensors 10 and 40 are operable to output a digital signal representing measured accelerations. Further, in some embodiments, one or more of the sensors 10 and 40 may comprise linear accelerometers.

In some embodiments, more than one of the sensors 10 and 40 may be integrated into the same integrated circuit package to allow the single package to provide acceleration measurements along more than one axis. Sensors 10 and 40 may each include two or more accelerometers each operable to output a signal corresponding to a measured acceleration.

In some examples, sensors 10 and 40 each include two accelerometers adapted to measure accelerations in two directions separated by an angle greater than zero degrees and each provide a signal corresponding to the measured acceleration. In some examples, sensors 10 and 40 may each include at least three accelerometers adapted to measure accelerations in three directions each separated by an angle greater than zero degrees and each provide a signal corresponding to the measured acceleration. In some embodiments, the three accelerometers may be oriented in a mutually perpendicular configuration. In one example, sensors 10 and sensors 40 are each a triaxial accelerometer. However, sensors 10 and 40 may include any number of accelerometers, including a single accelerometer positioned in any configuration to provide acceleration measurements.

Transceiver 20 and transceiver 46 are configured for wireless communication using various RF protocols. For example, transceiver 20 and transceiver 46 may communicate utilizing Bluetooth, ANT, and/or any other wireless protocols.

The filters 16 and 42 are operable to couple with the one or more accelerometers and filter acceleration measurements and/or signals corresponding to acceleration measurements. The filters 16 and 42 may include analog and digital components operable to filter and/or provide other pre-processing functionality to facilitate the estimation of motion parameters by the processors at controllers 18 and 44. In various examples, the filters 16 and 42 are operable to filter signals provided by the one or more accelerometers, or signals derived therefrom, to attenuate perpendicular acceleration, to compensate for gravity, and/or to minimize aliasing. The filters 16 and 42 may include discrete components for performing each of these filtering functions or use the same components and hardware for these, and other, filtering functions.

The anti-aliasing provided by the filters 16 and 42 generally reduces or prevents aliasing caused by sampling of the signals provided by, or derived from, the one or more accelerometers. In some embodiments, the filters 16 and 42 include a relatively wideband filter designed to attenuate signal frequencies in excess of one-half of the sampling frequency used in any subsequent analog-to-digital conversions provided by the controllers.

The filters 16 and 42 may include any analog and digital components for filtering signals and measurements, including passive and active electronic components, processors, controllers, programmable logic devices, digital signal processing elements, combinations thereof, and the like. The filters 16 and 42 may also include an analog-to-digital converter to convert analog signals provided by the one or more accelerometers to digitize signals for use by the processors at controllers 18 and 44. The filters 16 and 42 may also include conventional pre-sampling filters. In some examples, the low-pass filter 18 may be an adaptive filter operable to employ static and/or varying cut-off frequencies between about 0.5 Hz and 10 Hz.

In one example, sensor unit 6 worn about the user chest contains substantially similar components to that of sensor unit 4 illustrated and described in reference to FIG. 3A. In one example, sensor unit 6 includes a heart rate monitor to advantageously benefit from its position across the user chest.

Figure 3B:
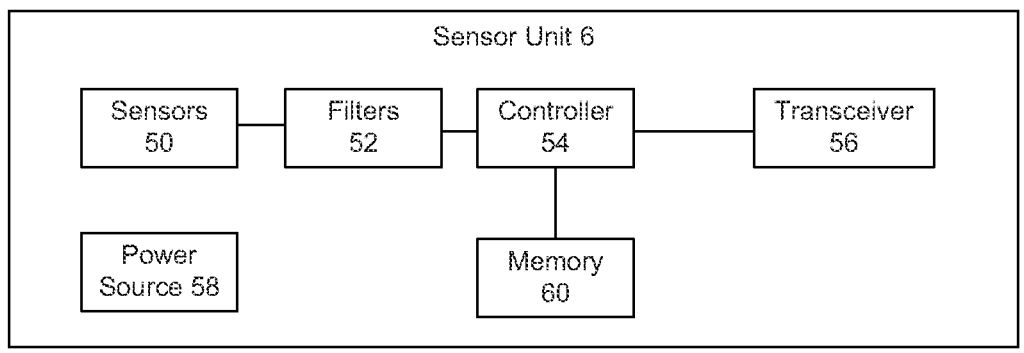
FIG. 3B illustrates a simplified block diagram of a torso mounted component of the system shown in FIG. 1.

FIG. 3B illustrates a simplified block diagram of a torso mounted component, sensor unit 6, of the system shown in FIG. 1. Sensor unit 6 includes sensors 50, filters 52, controller 54, transceiver 56, power source 58, and memory 60. Controller 54 may include one or more signal processors. In one example, power source 58 is a battery. Operation of the various components of sensor unit 6 are substantially similar to that of the similarly named components of sensor unit 4 described above with respect to FIG. 3A.

Sensor unit 6 includes one or more sensors 50. In one example, sensors 50 include one or more accelerometers. In one example, the sensors 50 include a gyroscope. In one example, the sensors 50 include a heart rate monitor. In one example, the one or more accelerometers include one or more tri-axial accelerometers. In one example, the one or more accelerometers are linear accelerometers. In one example, sensors 50 include a pair of sensors 50a and 50b which are parallel spaced triaxial accelerometers as shown in FIG. 1.

Depending upon the location of the sensor, one or more motion analysis algorithms may be used to determine one or more motion parameters. Sensor unit 2, sensor unit 4, and sensor unit 6 may store in memory a database of motion analysis algorithms corresponding to various combinations of attachment positions and motion classifications as appropriate. For example, the memory may include motion analysis algorithms for: foot, chest, and arm attachment locations.

Utilizing one or more selected motion analysis algorithms and acceleration signals provided by the sensors, the sensor unit 2, sensor unit 4, or sensor unit 6 may estimate, calculate, identify, or otherwise determine one or more motion parameters. For example, the motion parameter may correspond to direction of movement of a user leg or arm in any direction, degree of synchronization of movement of an opposite user arm and leg, vertical displacement of the user torso (and effectively, the user head), rotation of the user torso, side to side (i.e., left to right or horizontal) movement of the user torso in a plane centered between the front and back of the runner substantially perpendicular to the direction of locomotion, rotation of the user arm about the user torso or movement of the user arm in a side to side direction, stride speed, acceleration, velocity, stride distance, total distance, gait efficiency, energy, maximum impact, speed variability, strike time, steps, step cadence (e.g., number of steps per minute, also referred to herein as "stride rate" herein) and combinations thereof, or any other motion parameter described herein. Furthermore, the motion parameter determined may correspond to any parameter associated with the motion of the user. In one example, motion parameters are calculated at each individual sensor unit 2, sensor unit 4, and sensor unit 6. In a further example, sensor unit 2 receives data from sensor unit 4 and/or sensor unit 6 and calculates motion parameters.

In one example, the output of sensors 40 at sensor unit 4 is processed to determine the time at which a stride begins and ends by determining when a runner's foot impacts the ground, when a runner's foot leaves the ground, and when a runner's foot is stationary relative to the ground. By analyzing various changes in measured accelerations, the controller 44 or controller 18 may compute the stride direction and duration and information corresponding thereto, such as stride frequency. The stride frequency may represent the number of strides per second or other indications of the rate of stride.

In various embodiments, the controller 18 is operable to compute the motion parameter metrics and/or estimate the motion parameters for each detected stride to facilitate the accurate analysis of movement, where the motion parameters are associated with sensor unit 2, sensor unit 4, and/or sensor unit 6. Alternatively, motion parameter metrics are calculated for each detected stride at sensor unit 2, 4, and 6, respectively.

In one example, sensor units 2, 4, and 6 are accelerometer-based sensor units. Sensor units 2, 4, and 6 each include one or more accelerometers and an amplifier circuit (including a high-pass filter integrated therein). The accelerometer or accelerometers in each unit may comprise any of numerous devices or circuits capable of detecting acceleration of the body part to which the sensor unit is attached and produce an output signal in response thereto, and the invention is not limited to the use of any particular type of accelerometer. In further examples, the accelerometer may be replaced with other suitable devices which may alternatively be used Sensor units 2, 4, and 6 include accelerometers arbitrarily oriented relative to the direction of user motion for generation of a signal corresponding to user motion. Sensors may be placed in any location or combination of locations on his or her body.

In one example, the accelerometers are piezo-electric accelerometers, such as those manufactured by Murata or Analog Devices, Inc. The sensor units include amplifiers which amplify the acceleration signal from the accelerometer to a level suitable for an analog-to-digital converter (A/D converter or ADC) which converts the amplified analog acceleration signal to a digital signal. The digital signal is supplied to a microprocessor which performs the analysis of the waveform of the acceleration sensor signal, the computation of the speed, stride length and other parameters of the running person. The electronic components necessary to perform the functions of the sensor unit 2, 4, and 6 may be mounted on a small printed circuit board, which is placed in a housing to be attached to the desired runner body part.

The example system shown in FIG. 1 includes a sensor unit 4 system shown in FIG. 3A for sensing and transmitting some type of athletic performance data. More specifically, in this example structure, athletic performance data (e.g., physical or physiological data associated with an athletic performance) is sensed by sensor(s) 40, and data from these sensor(s) is sent to the sensing system's processing system, e.g., a microprocessors at controller 44, which optionally may cause the data to be stored (e.g., in a storage system or memory 49), further processed, etc. A power source 48 may be provided to operate the various components of the sensor unit 4 system, such as the sensors 40, the controller 44 and associated microprocessors, the transceiver 46, memory 49, and/or any other necessary or desired components. If desired, the microprocessor on board the sensor unit 4 system, if any, may process the sensor data, change its form or format, or otherwise manipulate the data prior to sending it on to other parts of the system, such as to sensor unit 2.

At an appropriate or desired time (e.g., when a data request is received, periodically, automatically, upon user demand, etc.), the sensor unit 4 system may send at least some portion of its data (e.g., raw data directly from one or more of the sensors, data derived at least in part from the raw data, etc.) to the sensor unit 2, illustrated in FIG. 2, for further processing and/or eventual output to a user via user interface 7. This may be accomplished, for example, as shown in FIG. 1, via a wireless data transmission system (e.g., from wireless data transfer or transceiver element 46 in the sensor unit 4 system to wireless data receiving element transceiver 20 in the sensor unit 2) or in any other desired manner without departing from this invention. Any desired wireless protocol, broadcast protocol, or other data transmission protocol may be used without departing from the invention.

Once received at the sensor unit 2, the athletic performance data may be further processed, if necessary or desired, and then supplied to the processing system (e.g., a microprocessor at controller 18) of the sensor unit 2. This may be accomplished at any suitable desired time or timing (e.g., when a data request is received, automatically, periodically, on user demand, etc.) based on the measured motion parameter without departing from this invention. From there, the data may be further processed, if necessary or desired, and then sent to an output device in a form suitable for output to a user (e.g., in audio, video, and/or alphanumeric form, etc.).

Figure 4:
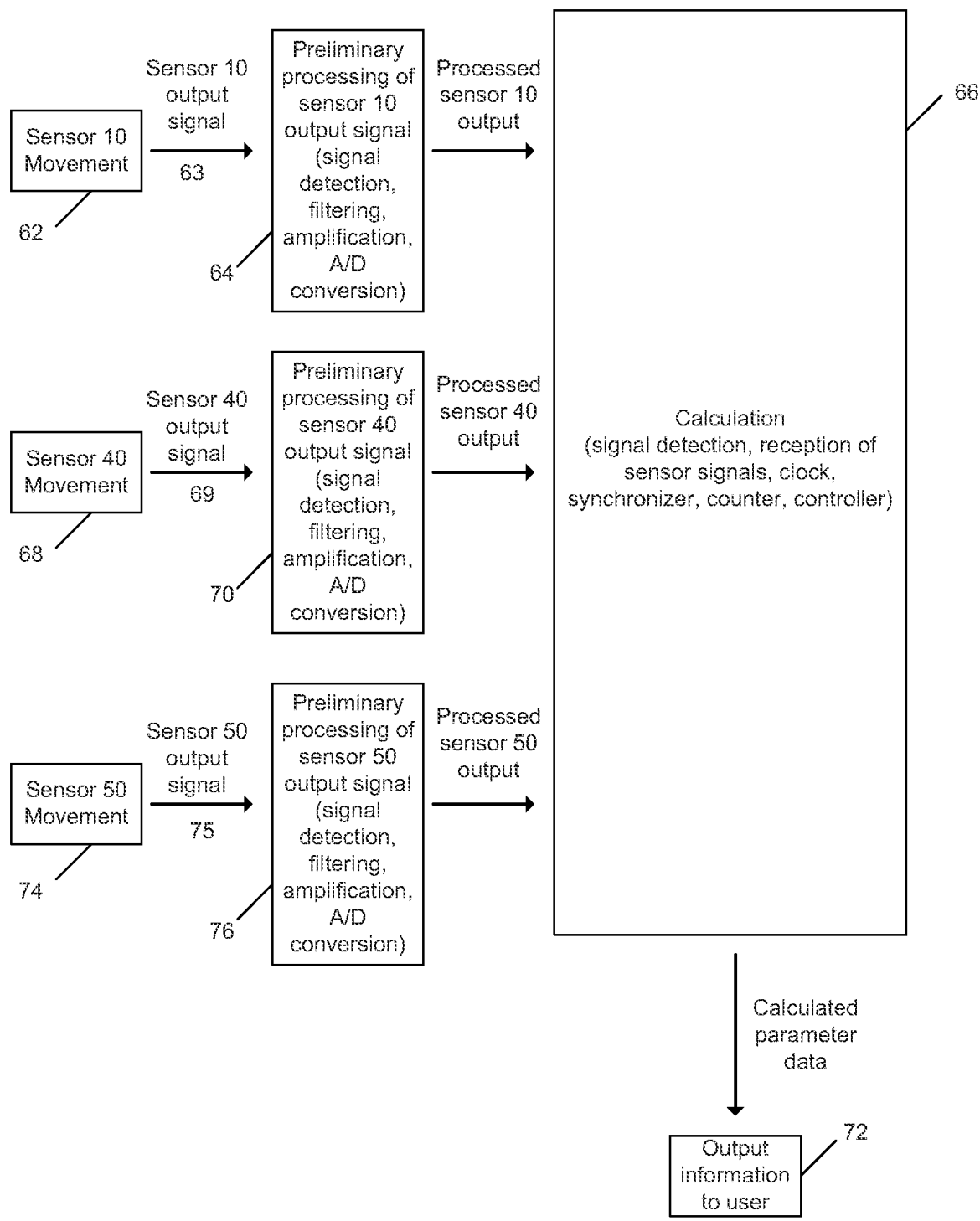
FIG. 4 illustrates an example of an athletic performance monitoring arrangement.

FIG. 4 illustrates an example of an athletic performance monitoring arrangement. During operation, sensor 10 movement 62 results in a sensor 10 output signal 63 which is sent to preliminary signal processing 64. In one example, preliminary signal processing 64 includes amplifying, filtering, signal detection, and transmission. Following preliminary signal processing 64, a processed sensor 10 output is sent to calculation unit 66 for further processing.

Similarly, sensor unit 40 movement 68 results in a sensor unit 40 output signal 69 which is sent to preliminary signal processing 70. In one example, preliminary signal processing 70 includes amplifying, filtering, signal detection, and transmission. Following preliminary signal processing 70, a processed sensor unit 40 output is sent to calculation 66 for further processing.

Similarly, sensor unit 50 movement 74 results in a sensor unit 50 output signal 75 which is sent to preliminary signal processing 76. In one example, preliminary signal processing 76 includes amplifying, filtering, signal detection, and transmission. Following preliminary signal processing 76, a processed sensor unit 50 output is sent to calculation 66 for further processing.

Calculation unit 66 receives multiple sensor output signals for calculating various desired motion parameters as described herein. Calculation 66 includes one or more signal receivers for receiving the sensor signals associated with the measurement variable from sensors 10, sensors 40, sensors 50, or any other system sensors. In certain examples, data from only select sensors is received and processed, depending on the desired motion parameter to be monitored. The one or more signal receivers also receive other information. Calculation unit 66 also includes signal processing for processing all of the received information. In operation, calculation unit 66 may perform processing functions including reception of sensor signals, clocking, synchronization, counting, timing, and signal detection.

The athletic performance monitoring arrangement illustrated in FIG. 4 includes processing to determine the motion parameters described herein. In one example, the determination of whether the runner arm and leg motions are synchronized are determined as described below in reference to FIGS. 5-7 utilizing the accelerometer output signals. Calculated motion parameter data is output to user 72 as set by the user via a user interface.

In various examples, the essential functions of the performance monitoring and measuring arrangement described can be implemented using separate components, integrated circuits, ASIC circuits, software or any combination of these. Various functions can be distributed among several components or performed at a single component as desired.

Figure 5:
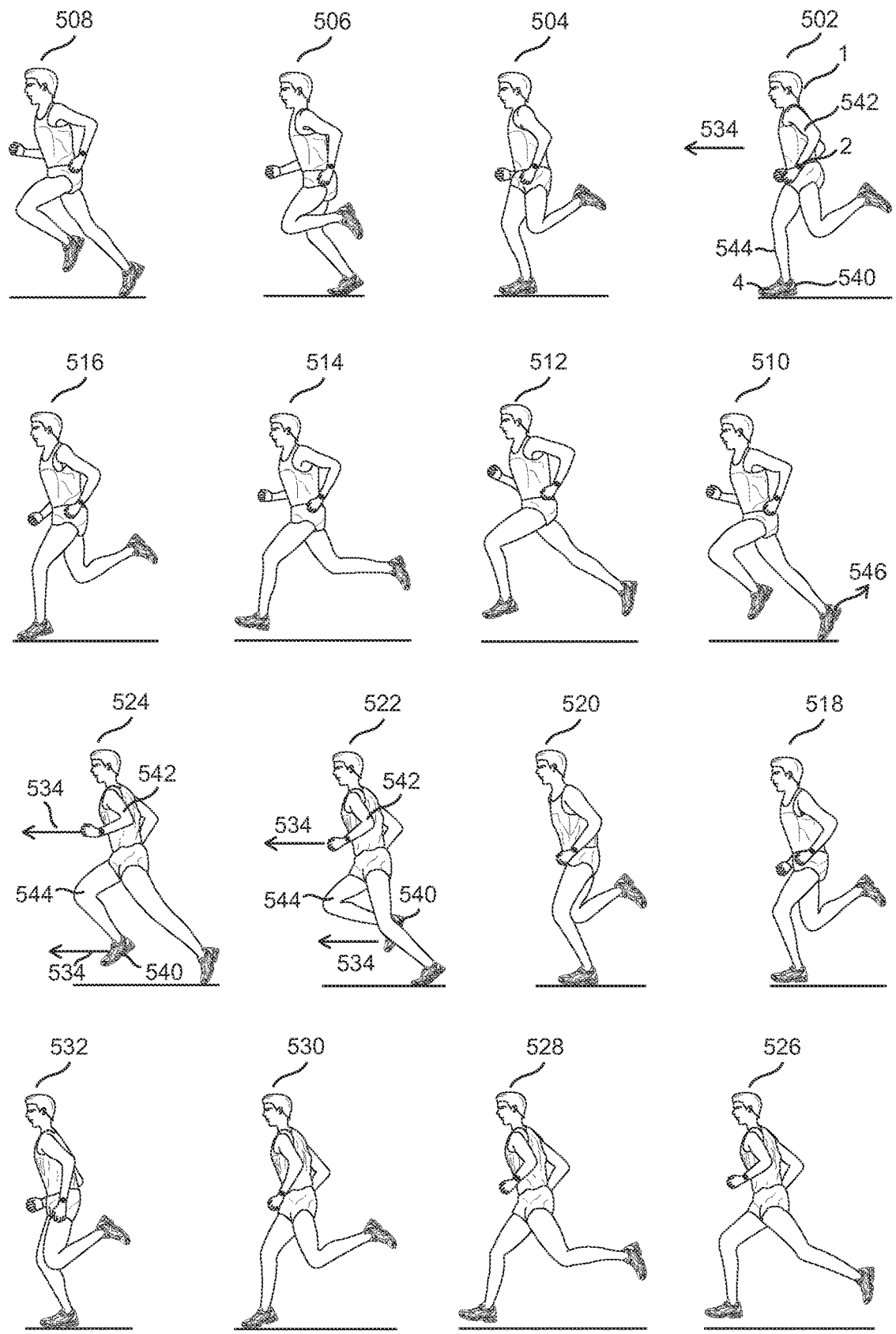
FIG. 5 illustrates a running progression of a runner wearing the system for athletic performance monitoring in one example.

FIG. 5 illustrates a running progression of a runner wearing the system for athletic performance monitoring in one example. FIG. 5 shows a running person 1 wearing a right shoe 540 with built-in sensor unit 4. The arrow 534 indicates a forward direction of acceleration of the shoe 540 along the line between the nose and heel of the shoe 4. The arrow 534 indicates a forward direction of acceleration of the sensor unit 2 (i.e., the runner left arm 542). As shown in FIG. 5, the forward direction is the direction in which runner 1 is running. The sensor units 2 and 4 should be mounted and oriented to be sensitive in the direction indicated with the arrows in FIG. 5. For example, the sensor unit 4 comprises an acceleration sensor unit 4 mounted in such a way that it senses acceleration in a direction substantially parallel to a line between the nose and the heel of the shoe 540.

In the running progression shown in FIG. 5, various time progressive snapshots 502 through 532 of the runner 1 are shown. The runner 1 is wearing a sensor unit 2 in the form of a wristwatch on a left arm 542 and is wearing sensor unit 4 on a right leg 544. In a further example, the runner 1 may wear sensor unit 2 on a left arm and wear sensor unit 4 on a right leg. In this example, sensor unit 2 and sensor unit 4 are worn are worn on opposite sides of the body (i.e., right side versus left side). Thus, if sensor unit 2 is worn on a right arm, sensor unit 4 is worn on the left leg. If sensor unit 2 is worn on a left arm, sensor unit 4 is worn on a right leg.

At snapshot 510, the runner right shoe 540 is or has just left the ground, referred to also as "toe-off" event, in a rearward direction 546 (i.e., a direction opposite the forward running direction) and upward direction. Overlapping with the rearward and upward direction of the right shoe 540, the runner left arm 542 is swung in a rearward direction (i.e., a direction opposite the forward running direction).

At snapshot 520, the runner right shoe 540 has reached its maximum rearward back kick height and is about to be begin its swing forward in the forward direction 534. At snap shot 522, the runner right shoe 540 is moving forward in forward direction 534, toward its maximum forward acceleration. Overlapping with the forward direction of the right shoe 540, the runner left arm 542 is swung in the forward direction 534.

At snap shot 532, the runner right shoe 540 has landed on the running surface, referred to as a foot strike event, returning to the position shown in the start of the stride in snapshot 502. Snap shot 532 illustrates the completion of one stride of the user right foot began at snap shot 502. During locomotion the runner will then repeat the sequence shown in snap shots 502-532.

In the runner stride between a toe-off event and a foot strike event for a given foot, the foot is in the air for a "foot in air" amount of time. In the runner stride after foot strike but before toe-off, the foot is on the ground for a "foot on ground" amount of time. Snapshots 502 to 532 show a sequence in which the runner left arm 542 and right leg 544 are desirably substantially synchronized in direction, with overlapping movement in either the rearward direction or forward direction.

Systems and methods described herein are operable to detect whether left arm 542 and the right leg 544 are desirably synchronized in either the rearward or forward direction or whether they are substantially unsynchronized such that the left arm 542 is substantially moving forward while the right leg 544 is moving rearward, or vice versa. The degree of synchronization may be measured. For example, the amount of overlap between movement of both left arm 542 and right leg 544 in the same direction is monitored. A threshold amount of overlap may be set, above which synchronization is determined to be present and below which synchronization is determined not to be present.

In one example, the threshold amount of overlap is set using the learning/calibration mode described above whereby a user runs with a desired synchronization between the opposite arm and leg and the amount of overlap in the same direction is measured and set as the threshold value or used as the basis for setting the threshold value. For example, the actual threshold value used during regulation operation (i.e., non-learning mode) is set slightly below the measured threshold value.

Figure 6:
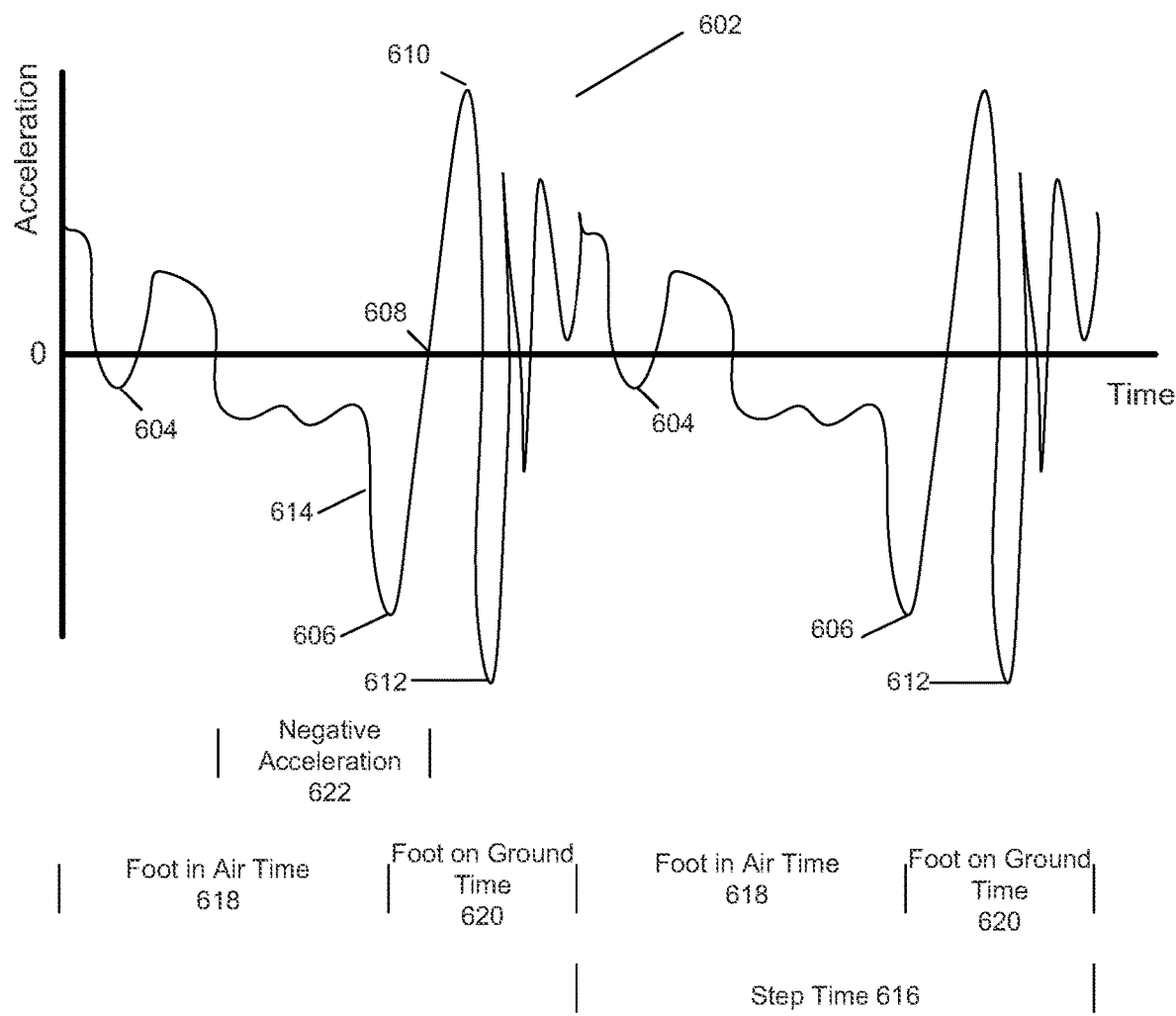
FIG. 6 illustrates a graph showing a typical output signal of a sensor mounted on a runner foot during locomotion.

FIG. 6 illustrates a graph showing an exemplary typical output signal of a sensor mounted on a runner foot during locomotion. FIG. 6 shows an example of an amplified accelerometer output signal 602 that may be provided by the sensor unit 4 to the controller 44 when the runner 1 is in locomotion on foot. Output signal 602 may be converted into digital values.

As also shown in FIG. 6, the signal 602 may fluctuate dynamically in response to movement of the user's foot that occur when the user is walking or running. When the level of the signal 602 is greater than zero, this indicates that the accelerometer is sensing a positive acceleration along the acceleration sensing axis, and when the level of the signal 602 is less than zero, this indicates that the accelerometer is sensing a negative acceleration along the acceleration axis. The acceleration signal 602 is subjected to an algorithm executed by a microprocessor.

Particular characteristics of the signal 602 may be identified which are indicative of particular occurrences during each footstep. In one example, signal 602 is analyzed to (1) identify occasions when the user's foot first leaves the walking or running surface after having been in contact with the ground during a footstep (e.g., a "toe-off" events), (2) to identify occasions when the user's foot first impacts the ground after having been airborne (e.g., "foot strike" events), (3) to identify occasions when the user's foot is airborne, (4) to identify occasions when the user's foot is moving forward in the direction of locomotion, and (5) to identify occasions when the user's foot is moving rearward opposite the direction of locomotion.

The relatively small negative peaks 604 indicate the beginning of a stride which corresponds to the moment the shoe leaves the ground and starts moving rearward and upward (i.e., a toe-off event). The zero crossing 608 after the large negative peak 606 indicates the end of the stride which corresponds to the moment the shoe lands on the ground again (i.e., a foot strike event). Following foot strike, but before toe-off, the user foot is in contact with the ground for a period of time ("foot on ground time"). Following toe-off, but before foot-strike, the user foot is in the air ("foot in air time" or simply "air-time"). The stride time may be measured as the time between zero crossings after the large negative peak 606.

In one example, an algorithm identifies the beginning and end of a stride. The signal 602 is analyzed to find the relatively small negative peaks 604 in the signal which are indicative of the beginning of a stride and the relatively large negative peaks 606 just before the zero crossings 608 which are indicative of the end of a stride. For example, negative peaks are detected by monitoring when the first derivative of the acceleration signal changes from negative to positive. Further, a smoothed version of the acceleration signal 602 is constantly monitored. Finally two minima are logged, the overall minimum and a local minimum somewhere around the smaller negative peak 604 at the moment the foot leaves the ground. When, at a certain negative peak, the value of the acceleration signal is below a certain limit, the peak is detected. This limit lies half way between the smoothed signal and the minimum.

In one example, toe-off events are identified by monitoring the signal 602 for characteristics that indicate a toe-off event may have potentially occurred. For example, one characteristic in the signal 602 indicative of a potential toe-off event is a large inflection in the signal 602. In this example, inflections in the signal 602 are monitored to identify and to continuously update the identification of a largest inflection to occur in the signal 602 subsequent to the most recent foot-strike event.

In a further example, toe-off events are identified by monitoring the signal 602 for characteristics that indicate the foot is definitely airborne. Such characteristics are referred to herein as the signal's "air signature". The air signature may, for example, be an identified period of relative smoothness substantially free from sharp transitions in the signal 602. When it is determined that the foot is airborne (i.e., an air signature is identified), the most recently identified potential toe-off event is identified as the actual toe off event. The end of the stride can be recognized comparatively easily in the acceleration signal 602, because the hard strike of the foot's landing on the ground causes high acceleration peaks 610 and 612, for example.

In one example, foot-strike events may be identified by monitoring the signal 602 for sudden, sharp inflections following the relatively smooth condition of the signal 602 generated while the foot is airborne. In one example, characteristics of the signal 602 are monitored to determine whether the signals satisfy at least one of a plurality of predetermined criteria consistent with the occurrence of a foot-strike event. In one example, after an air signature of the signal 602 has been identified (i.e., it has been determined that the foot of the user is airborne), a subsequent sharp, positive peak 610 in the signal 602 is one characteristic in the signal 602 that is indicative of the foot of the user impacting the running surface.

In one example, periods in which the user's foot is moving forward in the direction of locomotion such as in a stepping motion may be identified by monitoring the signal 602 for: (a) characteristics that indicate the foot is airborne combined with period of negative acceleration 622 with an increasing negative acceleration 614 leading to a large negative peak 606, or (b) characteristics that indicate a foot strike has occurred, where a period of negative acceleration prior to the foot strike indicates movement in the forward direction, or (c) a period of negative acceleration prior to the relatively large negative peaks 606 just before the zero crossings 608.

In one example, periods in which the user's foot is moving rearward in a backward and upward direction following initial toe-off may be identified by monitoring the signal 602 for: (a) characteristics that indicate the foot is airborne combined with period of positive acceleration, or (b) the period of time immediately following toe-off, but prior to movement of the foot in an identified forward direction.

In one example, the algorithm performs a single and double integration of the acceleration signal 602 during the integration time between the beginning of the stride and the end of the stride. The single integration of the acceleration signal results in the speed v(t) of the travelling foot as a function of time, while the double integral of the acceleration signal gives the travelled distance x(t) of the foot as a function of time.

As shown in FIG. 6, the period of a complete footstep of the runner (i.e., a step time 616) may be measured between the identified foot-strike events of the runner. The portion of each measured step time 616 during which the user's foot is in contact with the running surface (i.e., a foot on ground time 620) may be measured between each detected foot-strike event and a subsequently-detected toe-off event 704.

The portion of each measured step time 616 during which the user's foot is airborne (i.e., a foot in air time 618) may be measured between each detected toe-off event and a subsequently-detected foot-strike event. Thus, for each complete footstep taken by the user, an accurate measurement may be made of each step time 616 of the user, as well as the portions of that step time 616 attributable to foot on ground time 620 and foot in air time 618. A complete footstep means a movement cycle during which the foot of a user begins in a particular position and again returns to that same position. In one example, this information may be used by processors at the sensor unit 2 or sensor unit 4 to accurately calculate the speed and/or pace of the user, the distance traveled by the user, etc., during the corresponding footstep taken by the user.

In one example, radio transmissions between the foot-mounted sensor unit 4 and the wrist-mounted sensor unit 2 may be made only during the time during which the foot is on the ground because the controller 44 need not be employed to monitor the signal 602 during these time periods. After each foot-strike event the foot of the user will necessarily be on the ground for at least a minimum period of time, and it is not necessary during this period of time to analyze the signal 602 to identify potential occurrences of a toe-off event. Therefore, it is possible to ignore the signals during this particular period of time. Similarly, in one example, calculations involving data accumulated by the foot-mounted sensor unit 4 may be made only during this foot on the ground time 620, thereby consuming processing power only during time periods when the signal 602 need not be actively analyzed.

Similar to the manner in which the accelerometer output signal of a foot mounted accelerometer within sensor unit 4 is processed, the accelerometer output signal of an arm mounted accelerometer within sensor unit 2 is processed. However, analysis of the arm acceleration signal is simplified in that the signal does not contain characteristics associated with a ground strike nor a period of time in which the arm remains on the ground. Rather, during running, the user arm is typically swung forward and backward in a periodic manner. Sensor unit 2 and sensor unit 4 are synchronized in time and clocking to compare the outputs of sensor unit 2 and sensor unit 4.

The arm acceleration signal may fluctuate dynamically in response to movement of the user's arm that occur when the user is walking or running. In one example, the accelerometer is oriented such that when the level of the arm mounted accelerometer signal is greater than zero, this indicates that the accelerometer is sensing a positive acceleration along the acceleration sensing axis, and when the level of the arm mounted accelerometer signal is less than zero, this indicates that the accelerometer is sensing a negative acceleration along the acceleration axis. The accelerometer output signal may be converted into digital values, in which case the positive/negative acceleration boundary may be an arbitrary positive value instead of zero.

The arm acceleration signal is subjected to an algorithm executed by a microprocessor. In one example, a smoothed version of the arm acceleration signal is constantly monitored to simplify monitoring. For example, a smoothed signal resembling a sinusoidal signal representing back and forth motion of the arm in a direction of sensitivity may be monitored.

Particular characteristics of the arm acceleration signal may be identified which are indicative of particular occurrences during each arm swing. In one example, the arm acceleration signal is analyzed utilizing an algorithm to (1) identify occasions when the user's arm is being swung forward in the direction of locomotion, and (2) to identify occasions when the user's arm is being swung backward in a direction opposite the direction of locomotion, and (3) to identify occasions and/or the extent to which the user's arm is being swung rotationally about the user's torso.

In one example, forward swings/movement of the arm are identified by monitoring the arm acceleration signal for characteristics that indicate the arm is being swung forward. In one example, the acceleration signal is analyzed to identify periods of negative acceleration. In one example, an increasing negative acceleration leading to a large negative peak is identified.

In one example, rearward swings/movement of the arm are identified by monitoring the arm acceleration signal for characteristics that indicate the arm is being swung rearward. In one example, the acceleration signal is analyzed to identify periods of positive acceleration. In one example, an increasing positive acceleration leading to a large positive peak is identified. In further examples, other algorithms may be utilized to determine the direction which the user arm is being swung. Although the user arm swing may have both a forward/reverse component and an up/down component, in one example, only sensitivity in the forward/reverse direction is analyzed. In further examples, sensitivity in the up/down direction is analyzed and/or sensitivity in a rotational direction about the user torso or left/right direction across the user body is analyzed in addition to the forward/reverse direction.

The system can be further extended by including in sensor unit 2 additional accelerometers oriented to measure arm swing in different directions. In a further example, three perpendicularly oriented linear accelerometers or a triaxial accelerometer sensitive to movement in three perpendicular directions is utilized to monitor the user arm swing in a plurality of directions, including forward/reverse (e.g., relative to the direction of locomotion), left/right (e.g., across the user's torso/body towards the opposite arm), and up/down (along an axis defined by and running through the user's head and feet). In one example, the user arm swing in a left/right direction and up/down direction is determined in much the same way as the forward/reverse swing is measured. In a further example, rotation of the arm about the user torso can be measured using a gyroscope.

In one example, a forward/reverse to left/right ratio is calculated. For example, where the sensor unit 2 is worn on the left arm, the amount of displacement (or alternatively, acceleration) in the forward direction is compared to the amount of the displacement (or alternatively, acceleration) in the rightward direction.

In a further example, a forward/reverse to up/down ratio is calculated. In a further example, a forward/reverse to rotation ratio is calculated. For any direction, either the displacement or acceleration may be measured.

In one example, too much left to right motion of the left arm or right to left motion of the right arm indicates the user is undesirably rotating the torso rather than maintaining it in a forward direction. Too much left to right motion of the left arm or right to left motion of the right arm may also indicate undesirable running form even when the user torso is not rotating back and forth during locomotion. Movement of the user torso is independently measured using chest mounted sensors as described herein. In one example, the system detects whether the user is undesirably swinging his arms in a left to right manner while maintaining a relatively still torso. In one example, the system detects whether the user is both undesirably swinging his arms in a left to right manner and undesirably rotating his torso during locomotion. In one example, the system detects whether the user is undesirably rotating the user torso even if the arms are maintained in a desired forward/reverse direction.

In further examples, the user may wear sensor unit 2 on his right arm instead of his left, or the user may wear sensor units having the necessary functionality of sensor unit 2 on both the left and right arm to monitor both arms and determine whether arm motion is symmetrical for both the left arm and the right arm.

As described previously, a learning/calibration mode (also referred to as a test mode herein) may be utilized to set the threshold values for the amount of rotation of the torso or left/right movement of the arms below which is acceptable and above which is unacceptable. As described previously, during learning mode where the runner is instructed to run with the desired form, and various parameters are measured corresponding to the desired range of motion. Often, the runner may be able to run with correct form for a brief time, as in the test mode, but will deviate if not completely mindful of correct form, as during longer training runs or races where the runner is otherwise occupied. These values are then stored and then used to compare to the actual motion of the runner during running. If the runner deviates from the test established values, an alarm is output. The learning/calibration mode may be utilized to establish threshold values for any monitored parameter, including opposite arm/leg synchronization, torso vertical displacement during locomotion, torso rotation, torso horizontal movement, arm horizontal movement (e.g., left to right or right to left), arm rotation (e.g., arm twisting) about the torso.

In the learning mode where the runner consciously minimized movement, the system stores measurements for how much side to side/rotational twisting occurred, and up/down movement occurred. Alternatively, values can be set at the factory based on tests of other normal users or based on elite athletes performing at a high level. Also, the settings may be varied based on a current speed of user. The system allows individual coaches and users option of modifying settings based on their ability levels, natural running style, current running form (e.g., adjust settings as user improves form), etc.

During running, it is desirable for the user to minimize unnecessary movement of the torso, either up and down, side to side, or rotational/twisting. In one example, the chest strap includes a rotation sensor to determine torso rotation. Rotation about an axis running the length of the user torso is measured (e.g., the left shoulder moves forward in the direction of travel while the right shoulder simultaneously moves rearward). In one example, the rotation sensor is a pair of spaced substantially parallel accelerometer sensors 50*a* and 50*b* which can be used to calculate angular acceleration based on the difference of the signals. In another embodiment, the rotation sensor is a gyroscope.

In one example, sensors 50*a* and 50*b* are triaxial accelerometers, thereby enabling measurement of the user torso in a multitude of directions. For example, the two accelerometers are utilized to measure horizontal (e.g., side to side or left to right) movement of the torso along an axis running perpendicular to the vertical length of the torso.

In one example, the chest strap includes at least one accelerometer oriented to measure acceleration along an axis perpendicular to the running surface (i.e., in a direction running the length of the user torso). This accelerometer may be utilized to calculate the height/distance that the torso moves along this axis during location in a manner similar to that described above in calculating distance travelled of a foot stride in the direction of locomotion. Utilizing a chest mounted accelerometer to calculate the distance the runner travels in the vertical direction (i.e., the vertical displacement height during the striding motion) is preferable over utilizing foot mounted sensors to perform this calculation as calculations are simplified since the motion of the torso during striding is less complex than the user foot which, for example, travels rearward and upward to a height not representative of the overall vertical displacement height.

In a further example, the chest strap includes at least two accelerometers in a substantially mutually perpendicular orientation which provide signals for use by the processing system to determine acceleration both along an axis perpendicular to the running surface and along an axis parallel to the running surface running from the back of the user torso to the front of the user torso in the direction of locomotion. These two accelerometers may be utilized to calculate a striding angle of the torso in the forward and upward direction.

In a further example, in addition to the two accelerometers mounted in a substantially mutually perpendicular orientation as discussed above, a third accelerometer is included. The third accelerometer is mounted in a direction substantially perpendicular to the other two accelerometers. The acceleration measured by the third accelerometer is used to determine the amount of motion along an axis running from the left side of the user body to the right side of the user body (i.e., side to side or left to right). In general, excess motion in this direction during running is undesirable. In one example, a triaxial accelerometer may be used in place of the one, two, or three accelerometer embodiments to measure acceleration in any of the desired directions of motion.

In one example, sensors 50*a* and 50*b* are two tri-axial accelerometers placed in parallel within the chest strap on each side of the user torso. The output of the two tri-axial accelerometers is processed to measure vertical displacement height during locomotion, torso rotation, left to right motion, or other undesirable torso motion.

Figure 7:
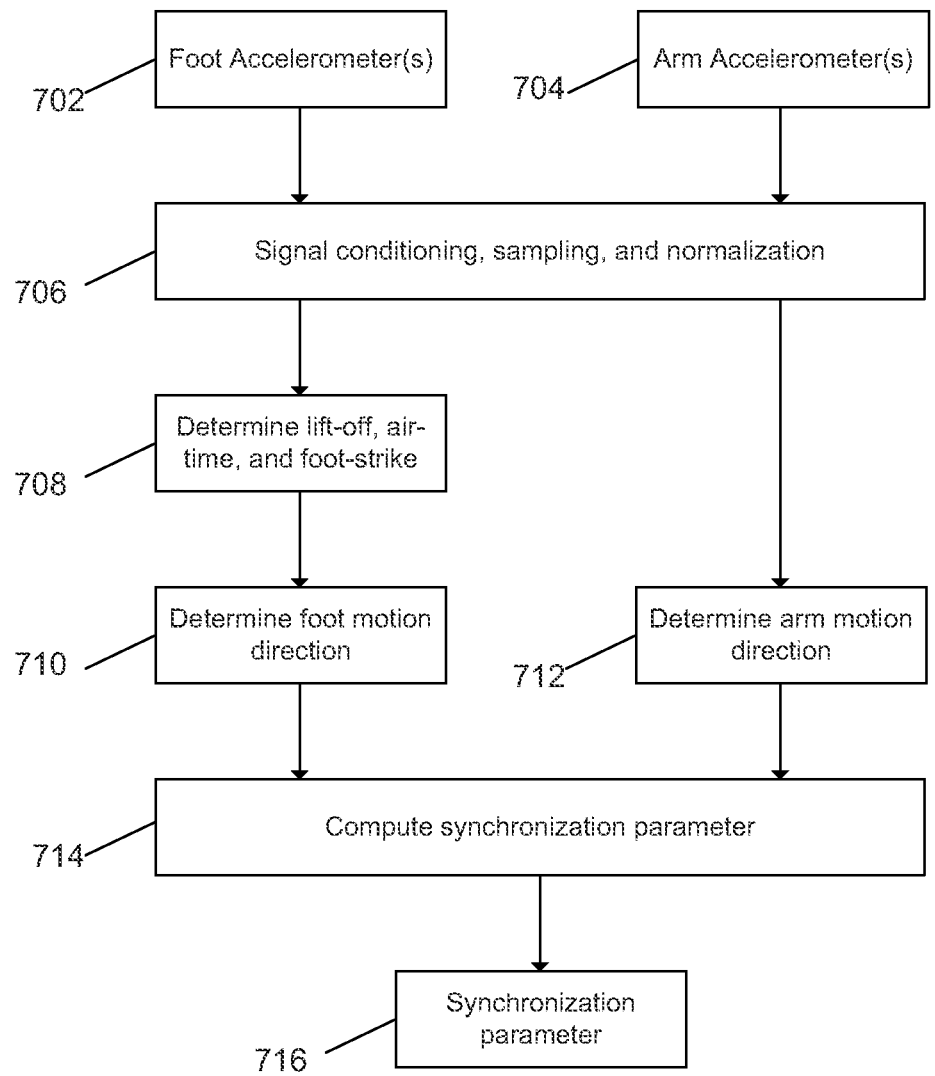
FIG. 7 illustrates an exemplary processing method.

FIG. 7 illustrates an exemplary processing method 700. Acceleration signals for each accelerometer 702, 704 in the system are sampled and stored for the duration of each user stride and processed as detailed in the exemplary block diagram of FIG. 7.

At block 706, the acceleration signals output from the foot mounted accelerometers are conditioned, sampled, and normalized. Similarly, the acceleration signals output from the arm mounted accelerometers are conditioned, sampled, and normalized.

At block 708, the acceleration signals output from the foot mounted accelerometers 702 are analyzed to determine lift off (e.g., toe-off), air-time, and foot-strike for each stride. At block 710, a foot direction motion is determined. At block 712, the acceleration signals output from the arm mounted accelerometers 704 are analyzed to determine an arm direction motion for each stride.

At block 714, utilizing the foot and arm direction motion, a synchronization parameter 716 is computed and output. For example, the amount of time in which the user foot and arm are moving in a same direction may be calculated. In one example, the calculated synchronization parameter is compared to a threshold value determined via a learning mode. In a further example, the calculated synchronized parameter is compared to a pre-determined value stored during manufacturing of the system.

Figure 8A:
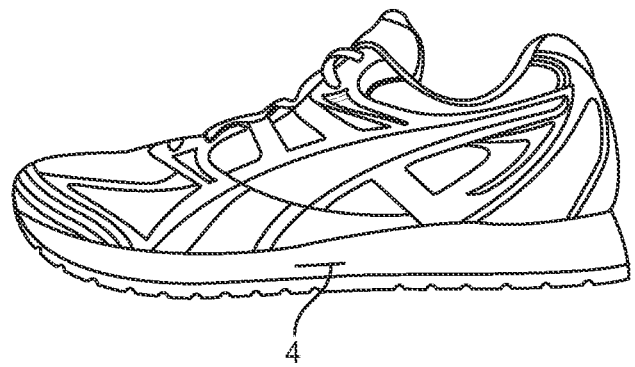
FIGS. 8A-8C illustrate examples of athletic performance monitoring systems to monitor user overstriding.
Figure 8B:
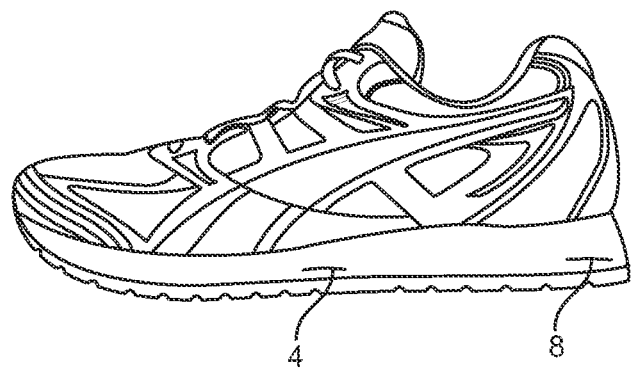
Figure 8C:
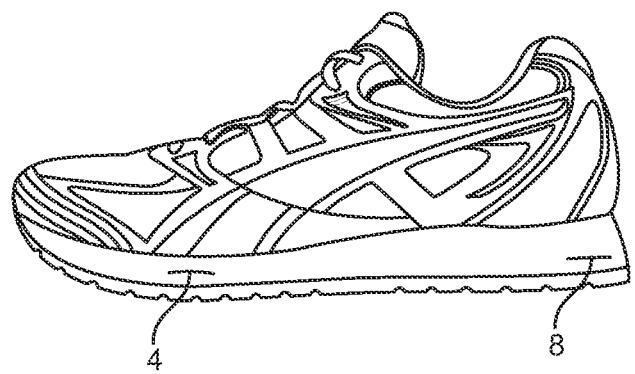

FIGS. 8A-8C illustrate examples of athletic performance monitoring systems to monitor user overstriding. In one example, sensor unit 4 is utilized to identify undesirable user overstriding. Overstriding is when, during running, the runner's foot lands in front of the runner's center of gravity. In other words, the runner's foot is landing too far in front of the user's body as opposed to closer beneath the user's body. Overstriding results in decreased performance as landing the foot in front of the runner's center of gravity produces a braking effect, slowing the runner down by stopping his or her forward momentum. Furthermore, overstriding results in loss of elastic recoil potential of the runner's muscles. Energy is stored in the runner's muscles when they are stretched. When these muscles recoil, the energy is released. Loss of elastic recoil potential results in less force production and more ground contact time. In addition, overstriding places greater impact stress on the runner's legs, producing greater stress on the runner's knees, hips and upper back, causing many running injuries.

The extent to which a specific runner overstrides may vary. In one example, what is desired is to reduce the amount of overstride specific to the user of the system. Thus, in one example, the user's stride improvement is measured with respect to a measured motion profile of the specific user/runner. For example, at the beginning of a training period, the user is directed to run with their normal/typical running motion. If the user typically overstrides, the user normal running motion will be an overstride. This "normal" running motion is profiled and stored in memory for baseline comparison. As used herein, the term "profile" refers to data or set of data portraying the characteristics of something. For example, a profile may be in graphic form, such as a sensor output signal, in table form, or may be data associated with the results of processing of such an output signal.

During the training phase, such as when the user is out running, the current user stride is monitored and profiled. The current user stride is then compared to the stored baseline motion profile to determine whether the user is running with reduced overstride compared to the user's stride at the beginning of the training phase. Advantageously, by using as the baseline comparison a previously stored undesirable stride motion profile (as opposed to a desirable stride motion profile), the initial user stride at the beginning of the training phase can be used since the user is already running with the undesired stride and therefore need not alter his or her stride to generate the baseline comparison profile. As such, the baseline profile has increased accuracy. Furthermore, this allows the baseline profile to be specific to the user. This advantageously allows the system to measure whether and the extent to which the user has improved their stride (i.e., reduced the amount they are overstriding) with respect to their own specific initial baseline stride since the start of the training phase. This is advantageous because it is desirable for the user to reduce the amount they are overstriding (e.g., the distance which the user foot is landing in front of the user's center of gravity) relative to when they began training even if the user has not completely eliminated overstriding or reduced it below a threshold level. In a further example, the system also determines whether the user is overstriding or not based without the need to compare the user current running stride to a previously stored motion profile.

In one example shown in FIG. 8A, sensor unit 4 is disposed in an athletic shoe beneath a midfoot area of the runner foot. In further examples, sensor unit 4 is disposed in an athletic shoe beneath a forefoot area of the runner foot, or beneath a heel area of the runner foot.

In this example, sensors 40 of sensor unit 4 include acceleration sensors configured to measure acceleration in a moving direction of a user foot during locomotion and output an acceleration signal responsive to the acceleration. The system includes a memory 49 storing an overstride acceleration motion profile associated with a user overstride. The system further includes a processing system configured to process the acceleration signal output from sensors 40 to produce a measured motion profile and compare with the stored overstride acceleration motion profile to identify a user overstride. The measured motion profile is a stride "signature" representative of the user stride. This acceleration signature varies based on whether the user foot lands in front of the user center of gravity or below the user's center of gravity. For example, if the measured motion profile matches the overstride acceleration motion profile, a user overstride is identified. Advantageously, the use of an accelerometer provides an output signal that varies based on takeoff from the ground, motion through the air in different directions and speeds, and contact with the ground, as shown in FIG. 6, thereby allowing the system to generate a measured motion profile of the user stride (i.e., the user's stride signature) and compare the measured motion profile with pre-stored motion profiles corresponding to different stride types to identify user overstride using a sensor located at only one position on the user foot.

In one example, the memory 49 further stores a plurality of acceleration motion profiles associated with user stride motions, and wherein the processing system matches the measured motion profile with an acceleration motion profile in the plurality of acceleration motion profiles to identify a user stride motion. For example, in addition to an overstride acceleration motion profile, other acceleration motion profiles may include motion profiles associated with desired user strides, such as user stride whereby the user foot lands beneath the user's center of gravity, such as beneath the user's hip. In one example, the stored motion profile includes a motion profile corresponding to the user foot landing on the user midfoot beneath the user's hip. The measured motion profile is compared to the stored motion profiles to identify the closest match.

In one example, the stored motion profile or profiles are user specific generated during a "learning" or calibration mode. In one example, the user may enter the learning mode with a user interface input action at sensor unit 2, such as by pressing a "learning mode" command button. During learning mode, the user is prompted to run with an overstride stride motion during an overstride time period. In one example, prompting a user to run with an overstride motion includes instructing the user to run in a manner such that the user foot lands in front of the user body's center of gravity. In one example, prompting a user to run with an overstride motion includes instructing the user to run in a manner such that the user foot lands far in front of the user body. In one example, prompting a user to run with an overstride stride motion includes instructing the user to run with a hips-back or seated position during running. In a further example, prompting a user to run with an overstride stride motion includes instructing the user to run in a manner such that the user foot lands heel first in front of the user body. During the overstride time period, the sensor output signal is received and processed to generate an overstride motion profile.

During learning mode, the user is also then prompted to run with a goal/desired stride motion during a goal stride time period. In one example, prompting the user to run with a goal stride motion during a goal time period includes instructing the user to run with the user foot landing beneath their body center of gravity. In one example, prompting the user to run with a goal stride motion during a goal time period includes instructing the user to run with a hips-forward body position during running. In one example, prompting the user to run with a goal stride motion during a goal time period includes instructing the user to run with a high step cadence during running. In one example, prompting the user to run with a goal stride motion during a goal time period includes instructing the user to run with decreased stride length during running. In one example, prompting the user to run with a goal stride motion during a goal time period includes instructing the user to maintain a bent knee during running throughout the entire stride motion. In one example, prompting the user to run with a goal stride motion during a goal time period includes instructing the user to run with the user foot landing beneath their body center of gravity landing on the ball of their foot first.

During the goal stride time period, the sensor output signal is received and processed to generate a goal/desired motion profile. The overstride motion profile and the goal/desired motion profile are then stored in memory for subsequent use during a running activity.

After the learn mode is completed, in operation during a running activity where the user is running with his or her normal stride, a sensor output signal is received and processed to generate a running activity motion profile. The running activity motion profile is then matched to the closest profile stored in memory. In this example, the running activity motion profile is matched to either the overstride motion profile or the goal/desired motion profile to identify whether the user is overstriding.

In a further example, the stored motion profile or profiles are pre-loaded onto the system memory, and are generated based empirical testing across a number of users. For example, the stored overstride motion profile may be a composite profile constructed based on the overstride profiles of a number of test users. Similarly, the stored goal/desired motion profile may be a composite profile constructed based on the goal/desired profiles of a number of test users. In a further example, both a learning mode and pre-loaded motion profiles are available to the user.

In one example, the pre-loaded stored motion profiles may offer the user a "beginner", "intermediate", or "advanced", or other comparable or similar designation levels (e.g., level 1, 2, or 3), from which the user may select. For example, if the user selects the "beginner" level, the system will output an indication that the user is overstriding only in the most severe case of overstriding (i.e., where the user's foot is landing far in front of the user's center of gravity). As the user improves his stride gradually to reduce overstriding, the user may progressively select more difficult/higher levels. For example, at the "advanced" level, the system may output an indication that the user is overstriding even when there is only slight overstriding.

In one example, sensor unit 4 is used in conjunction with a sensor unit 8 to identify user overstriding. In one example, sensor unit 4 is disposed in a midfoot region of a user foot as shown in FIG. 8B and a sensor unit 8 is disposed in a heel region. In a further example, as shown in FIG. 8C, sensor unit 4 is disposed in a forefoot region of a user foot and a sensor unit 8 is disposed in a heel region. In one example, sensor unit 8 is substantially similar to sensor unit 4 in both components and functionality. Sensor unit 8 includes sensor, filters, a controller, memory, transceiver, and power source having functionality as described above with respect to sensor unit 4. In a further example, sensor unit 8 is physically coupled to sensor unit 4 via a wired connection such as an electrical lead and does not utilize a wireless transceiver.

In one example, sensors 40 of sensor unit 4 include an acceleration sensor configured to measure a first acceleration in a moving direction of a first portion of a foot (e.g., the midfoot or forefoot) during locomotion and outputting a first acceleration signal responsive to the first acceleration. In one example, the first acceleration sensor is operable for coupling to a first portion of a user foot (e.g., the midfoot or forefoot) and configured to generate a first output signal corresponding to a first portion motion, the first portion motion comprising a rearward upward kick and a forward motion in the air in a direction of locomotion. For example, components of the first output signal corresponding to the rearward upward kick and forward motion in the air in a direction of locomotion are illustrated and described above in relation to FIG. 6. As shown in FIG. 6, the output signal varies as a result of the in-the-air motion of the user foot.

Sensor 8 includes an acceleration sensor configured to measure a second acceleration in a moving direction of a second portion of a foot (e.g., the heel of the foot) during locomotion and outputting a second acceleration signal responsive to the second acceleration. In one example, the second acceleration sensor is operable for coupling to a second portion of the user foot (e.g., the heel of the foot) and configured to generate a second output signal corresponding to a second portion motion, the second portion motion comprising a rearward upward kick and a forward motion in the air in the direction of locomotion.

The system further includes a processing system configured to process the first acceleration signal and the second acceleration signal to identify a user overstride. The processing system may be located at sensor 4, sensor 8, or a remote device such as a wrist worn device.

In one example, the processing system is operable to receive and process the first acceleration signal to produce a first measured motion profile and receive and process the second acceleration signal to produce a second measured motion profile, wherein the processing system is configured to utilize the first measured motion profile and the second measured motion profile in comparison with pre-stored motion profiles to identify a user overstride.

The pre-stored motion profiles may be generated (i.e., either during a learning mode or prestored by the manufacturer) as described above in reference to FIG. 8A with the difference that in addition to storing profiles generated by sensor unit 4, profiles generated by sensor unit 8 disposed at the user heel are also stored for both an overstride motion and goal/desired stride motion.

In operation during a running activity where the user is running with his or her normal stride (i.e., non-learning mode), sensor output signals from sensor unit 4 and sensor unit 8 are processed to generate measured running activity motion profiles (i.e., stride signatures) corresponding to the user midfoot (e.g., FIG. 8B) or user forefoot (e.g., FIG. 8C) and the user heel (e.g., FIGS. 8B and 8C). The measured running activity motion profiles are then matched to the closest (e.g., most similar waveform) pre-stored profiles stored in memory to identify the user stride type (e.g., overstride or desired). For example, pre-stored motion profiles corresponding to an overstride stride and desired stride may be pre-processed so that comparison with the measured motion profiles to identify the user stride type may be performed quickly.

In one example, the running activity motion profiles for both sensor unit 4 and sensor unit 8 must both match the corresponding overstride profiles stored in memory in order for an overstride determination to be made. In other words, the measured motion profile for sensor unit 4 must match the stored overstride motion profile for sensor unit 4 and the measured motion profile for sensor unit 8 must match the stored overstride motion profile for sensor unit 8 for the system to conclude a stride is an overstride. In this example, by requiring signatures from both sensor unit 4 and sensor unit 8 to match the stored overstride motion profiles, the system notifies the user that he is overstriding only when it is certain that the user is overstriding, indicating that the user is likely overstriding a significant amount. This requirement may also account for errors in analyzing the signatures and matching them to the stored profiles.

In one example, where one or both of the running activity motion profiles for sensor unit 4 and sensor unit 8 match the corresponding goal/desired profiles stored in memory, the system outputs a determination that the user stride is not an overstride (i.e., a goal/desired stride). In a further example, only one of the running activity motion profiles of either sensor unit 4 or sensor unit 8 need to match the corresponding stored overstride motion profile for the system to output a determination that the user stride is an overstride. This configuration is useful where analysis of whether one of the measured stride signatures is an overstride is indeterminate.

Figure 14:
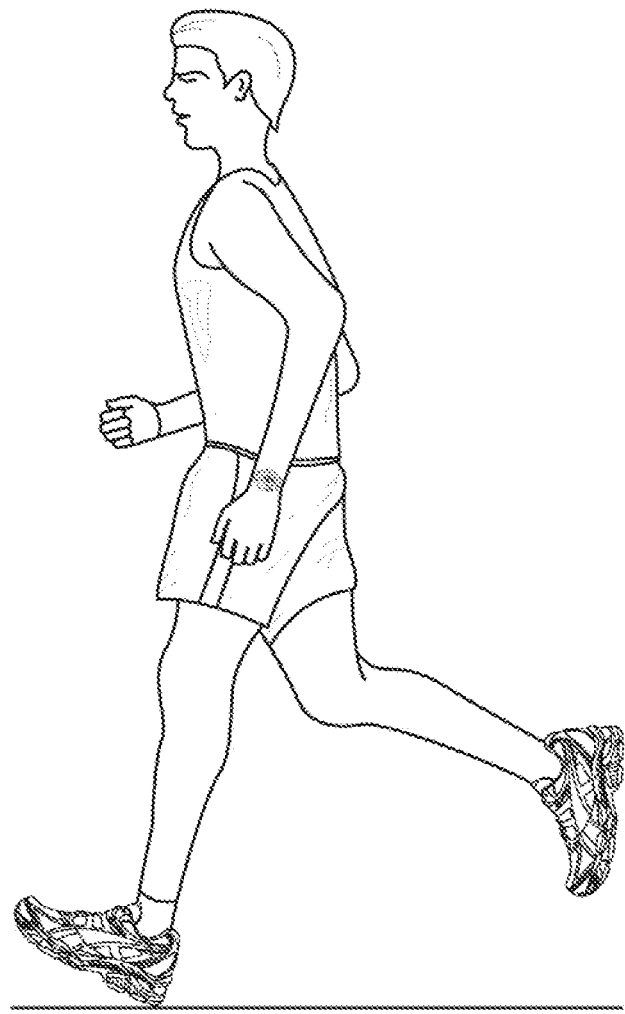
FIG. 14 illustrates one example indication of a user overstride where the runner heel strikes the ground prior to the midfoot or forefoot.

In a further example, the processing system compares the first output signal from sensor unit 4 and the second output signal from sensor unit 8 and identifies a difference in motion between the first foot portion (i.e., the midfoot or forefoot) and the second foot portion (i.e., the heel) in order to identify a user overstride. In one example, an algorithm is utilized to process the first output signal and the second output signal to identify whether the first foot portion or the second foot portion strikes the ground first. In one example, an algorithm is utilized to process the first output signal from sensor unit 4 to identify when the user midfoot or forefoot strikes the ground. An algorithm is utilized to process the output signal from sensor unit 4 to identify when the user heel strikes the ground. In this example, the system identifies an overstride if the user heel strikes the ground before the user midfoot or forefoot. FIG. 14 illustrates one example indication of a user overstride where the runner heel strikes the ground prior to the midfoot or forefoot in front of the runner's center of gravity. For example, identifying the occurrence of a foot strike on the running surface from the sensor signal is performed similar to as described above in reference to FIG. 6.

In a further example, the output of sensor units 4 and 8 are both compared to each other to identify user overstride and compared to pre-stored motion profiles to identify user overstride. Thus, the system advantageously allows for user overstride to be determined using two independent methods using the same two sensor units 4 and 8. In one example, both methods must determine that the user stride is an overstride for the system to output that the user stride is an overstride.

In one example, the processing system is further configured to determine a percentage of user strides which are overstrides over a given time period. Thus, each stride is designated as either an overstride or not an overstride. In one example, the system further includes a user interface in communication with the processing system, the user interface configured to output an alert if the percentage of user overstrides exceeds a tolerance. This tolerance may be pre-set by the manufacturer or configured by the user. For example, the tolerance may be preset or the user may set the tolerance at an alert percentage within the range of 30-60%, whereby an alert is output if the percentage of user strides which are overstrides exceeds the selected alert percentage. The user may adjust the alert percentage as his training progresses and reduces the extent of overstriding during his running activity.

In one example, the system further includes a user interface in communication with the processing system, the user interface configured to output a visual indication or an audible indication of the user overstride. In one example, the user interface is located at a wrist worn device in communication with sensor unit 4 and/or sensor unit 8 as necessary. In one example, the wrist worn device is configured to be worn device worn an arm of a person and includes a processing system including a processor configured to receive the first sensor data and the second sensor data and identify a user overstride motion. The wrist worn device further includes a user interface such as a display and audio output. In one example, the wrist worn device may be embodied in sensor unit 2 as described above in reference to FIG. 2.

In one example, a system includes a first foot sensor configured to output a first signal responsive to a takeoff rearward kick and a landing of a first portion of an athlete foot in a direction of locomotion. The system includes a second foot sensor configured to output a second signal responsive to a takeoff rearward kick and a landing of a second portion of the athlete foot in the direction of locomotion. The system further includes a processing system configured to analyze the first sensor output signal and the second sensor output signal to identify a user overstride. In one example, the first foot sensor includes a first inertial sensor and the second foot sensor includes a second inertial sensor. For example, the first inertial sensor is a sensor unit 4 having sensors 40 which include one more accelerometers and the second inertial sensor is a sensor unit 8 which includes one or more accelerometers, where sensor unit 4 and sensor unit 8 are operable as described above in reference to FIG. 8B and FIG. 8C.

In one example, sensor unit 4 is attached to the shoe upper in the region of the shoe laces via a clipping device and sensor unit 8 is attached via a clipping device to the shoe upper at the area above the heel area. Thus, sensor unit 4 and sensor unit 8 may be attached to any conventional shoe. In a further example, sensor unit 4 and sensor unit 8 are attached within a midsole area of a show such that sensor unit 4 and sensor unit 8 rest below the user foot when the shoe is worn.

In one example, the processing system is configured to identify a user overstride by determining a landing of the athlete foot relative to an athlete center of gravity, such as whether the athlete foot lands in front of the athlete body's center of gravity or approximately beneath the body's center of gravity.

In one example, sensors 40 of sensor unit 4 include an acceleration sensor configured to measure a first acceleration in a moving direction of a first portion of a foot (e.g., the midfoot or forefoot) during locomotion and outputting a first acceleration signal responsive to the first acceleration. In one example, the first acceleration sensor is operable for coupling to a first portion of a user foot (e.g., the midfoot or forefoot) and configured to generate a first output signal corresponding to a first portion motion, the first portion motion comprising a rearward upward kick and a forward motion in the air in a direction of locomotion. For example, components of the first output signal corresponding to the rearward upward kick and forward motion in the air in a direction of locomotion are illustrated and described above in relation to FIG. 6. As shown in FIG. 6, the output signal varies as a result of the in-the-air motion of the user foot.

Sensor 8 includes an acceleration sensor configured to measure a second acceleration in a moving direction of a second portion of a foot (e.g., the heel of the foot) during locomotion and outputting a second acceleration signal responsive to the second acceleration. In one example, the second acceleration sensor is operable for coupling to a second portion of the user foot (e.g., the heel of the foot) and configured to generate a second output signal corresponding to a second portion motion, the second portion motion comprising a rearward upward kick and a forward motion in the air in the direction of locomotion.

The system further includes a processing system configured to process the first acceleration signal and the second acceleration signal to identify a user overstride. The processing system may be located at sensor 4, sensor 8, or a remote device such as a wrist worn device.

In one example, the processing system is operable to receive and process the first acceleration signal to produce a first measured motion profile and receive and process the second acceleration signal to produce a second measured motion profile, wherein the processing system is configured to utilize the first measured motion profile and the second measured motion profile in comparison with pre-stored motion profiles to identify a user overstride.

The pre-stored motion profiles may be generated (i.e., either during a learning mode or prestored by the manufacturer) as described above in reference to FIG. 8A with the difference that in addition to storing profiles generated by sensor unit 4, profiles generated by sensor unit 8 disposed at the user heel are also stored for both an overstride motion and goal/desired stride motion.

In operation during a running activity where the user is running with his or her normal stride (i.e., non-learning mode), sensor output signals from sensor unit 4 and sensor unit 8 are processed to generate measured running activity motion profiles (i.e., stride signatures) corresponding to the user midfoot (e.g., FIG. 8B) or user forefoot (e.g., FIG. 8C) and the user heel (e.g., FIGS. 8B and 8C). The measured running activity motion profiles are then matched to the closest (e.g., most similar waveform) pre-stored profiles stored in memory to identify the user stride type (e.g., overstride or desired). For example, pre-stored motion profiles corresponding to an overstride stride and desired stride may be pre-processed so that comparison with the measured motion profiles to identify the user stride type may be performed quickly.

In one example, the running activity motion profiles for both sensor unit 4 and sensor unit 8 must both match the corresponding overstride profiles stored in memory in order for an overstride determination to be made. In other words, the measured motion profile for sensor unit 4 must match the stored overstride motion profile for sensor unit 4 and the measured motion profile for sensor unit 8 must match the stored overstride motion profile for sensor unit 8 for the system to conclude a stride is an overstride. In this example, by requiring signatures from both sensor unit 4 and sensor unit 8 to match the stored overstride motion profiles, the system notifies the user that he is overstriding only when it is certain that the user is overstriding, indicating that the user is likely overstriding a significant amount. This requirement may also account for errors in analyzing the signatures and matching them to the stored profiles.

In one example, where one or both of the running activity motion profiles for sensor unit 4 and sensor unit 8 match the corresponding goal/desired profiles stored in memory, the system outputs a determination that the user stride is not an overstride (i.e., a goal/desired stride). In a further example, only one of the running activity motion profiles of either sensor unit 4 or sensor unit 8 need to match the corresponding stored overstride motion profile for the system to output a determination that the user stride is an overstride. This configuration is useful where analysis of whether one of the measured stride signatures is an overstride is indeterminate.

In a further example, the processing system compares the first output signal from sensor unit 4 and the second output signal from sensor unit 8 and identifies a difference in motion between the first foot portion (i.e., the midfoot or forefoot) and the second foot portion (i.e., the heel) in order to identify a user overstride. In one example, an algorithm is utilized to process the first output signal and the second output signal to identify whether the first foot portion or the second foot portion strikes the ground first. In one example, an algorithm is utilized to process the first output signal from sensor unit 4 to identify when the user midfoot or forefoot strikes the ground. An algorithm is utilized to process the output signal from sensor unit 4 to identify when the user heel strikes the ground. In this example, the system identifies whether the user foot is landing in front of the body's center of gravity by determining if the user heel strikes the ground before the user midfoot or forefoot. Thus, the determination of whether the user heel strikes the ground before the user midfoot or forefoot may be used as an indicia of overstriding. Furthermore, in this example, the extent of overstriding can be determined by measuring the time between the heel strike and the midfoot or forefoot strike, with a greater amount of time indicating a larger amount of overstriding. By tracking this time, the system can determine if the user has reduced the amount they are overstriding relative to when they first began the training program. Thus, the system tracks not only whether the user is ovestriding or not overstriding, but the extent to which the user is overstriding.

In one example, sensor unit 4 and sensor unit 8 utilize pressure sensors such as piezo-electric sensors or piezoresistive pressure sensors in place of or in addition to accelerometers. Functionality in identifying overstriding is somewhat different where pressure sensors are utilized in that pressure sensors cannot create a motion profile or stride "signature" the way that accelerometers do as their output signal does not vary while the user foot is in the air based on foot movement in the air. As such, pre-stored motion profiles (e.g., "learned" or prestored overstride stride signatures or goal stride signatures) generated either during a learning mode or pre-loaded by the manufacturer are not utilized to identify overstriding, and two sensor units placed at different locations on the user foot are required. Where pressure sensors are utilized, sensor unit 4 and sensor unit 8 are disposed within a midsole or insole of the shoe at the midfoot or forefoot (e.g., sensor unit 4) and the heel (e.g., sensor unit 8). In this example, during running in a forward direction, the pressure sensor at sensor unit 4 outputs a signal indicating a transition from applied pressure to no-applied pressure responsive to a takeoff rearward kick of a first portion of the user foot, and outputs a signal indicating a transition from no-applied pressure to applied pressure responsive to a landing of the first portion of the user foot following takeoff. Similarly, the pressure sensor at sensor unit 8 outputs a signal indicating a transition from applied pressure to no-applied pressure responsive to a takeoff rearward kick of a second portion of the user foot, and outputs a signal indicating a transition from no-applied pressure to applied pressure responsive to a landing of the second portion of the user foot following takeoff.

In one example, the processing system is further configured to determine a percentage of user strides which are overstrides over a given time period. Thus, each stride is designated as either an overstride or not an overstride. In one example, the system further includes a user interface in communication with the processing system, the user interface configured to output an alert if the percentage of user overstrides exceeds a tolerance. This tolerance may be pre-set by the manufacturer or configured by the user. For example, the user may set the tolerance at an alert percentage within the range of 30-50%, whereby an alert is output if the percentage of user strides which are overstrides exceeds the selected alert percentage. The user may adjust the alert percentage as his training progresses and reduces the extent of overstriding during his running activity.

In one example, the system further includes a user interface in communication with the processing system, the user interface configured to output a visual indication or an audible indication of the user overstride. In one example, the user interface is located at a wrist worn device in communication with sensor unit 4 and/or sensor unit 8 as necessary. In one example, the wrist worn device is configured to be worn device worn an arm of a person and includes a processing system including a processor configured to receive the first sensor data and the second sensor data and identify a user overstride motion. The wrist worn device further includes a user interface such as a display and audio output. In one example, the wrist worn device may be embodied in sensor unit 2 as described above in reference to FIG. 2.

In one example, the system identifies a user overstride (e.g., whether the user foot is landing in front of the body's center of gravity) by determining after takeoff of the user foot whether sensor unit 8 at the user heel strikes the ground before sensor unit 4 at the user midfoot or forefoot and the amount of time between ground strike of sensor unit 8 and sensor unit 4, and the system outputs an indication of the extent of the user overstride. The greater the amount of time, the greater the amount of user overstride. For example, if the user is greatly overstriding, multiple alert beeps may be output whereas if the user is only slightly overstriding, a single alert beep is output. Whether a measured amount of time between sensor unit 4 and sensor unit 8 is deemed a large amount of overstride or a slight amount of overstride may be determined using a look-up table stored in memory. The look-up table matching time between strikes and overstride extent may be pre-loaded at the manufacturer and based on tests of various athletes of varying ability.

In one example, the amount of time between landing of sensor unit 4 disposed at the user forefoot and the sensor unit 8 at the heel is measured and utilized to determine the overstride angle at which the user foot leading with the user heel is striking the ground, where the overstride angle is defined by a line through the forefoot and heel and the ground. The greater the measured time, the greater the overstride angle. In one example, by monitoring whether the overstride angle has decreased, it is determined whether the user has reduced the amount of overstride.

In a further example, a single threshold time is utilized, above which it is output that the user is overstriding. The single threshold time may be stored in memory based on the results of a learning mode where the user is instructed to run with an overstride motion, where the system measures the time between the heel strike and midfoot strike and sets the threshold time based on the measured time during learning mode. For example, the single threshold time may automatically beset to a time 5-10 percent less than the measured time. In a further example, the user is provided with the option to adjust the threshold time upwards or down incrementally after learning mode based on actual usage. In a further example, during learning mode, the user first runs with a high amount of overstride and a first threshold time is measured. The user then runs with a moderate amount of overstride and a second threshold time is measured. The first threshold time and second threshold time are utilized during normal operation (e.g., non-learning mode) to identify whether the user is greatly overstriding or moderately overstriding based on the measured time between heel strike and midfoot or forefoot strike.

In this example, the system identifies a desired user stride by determining after takeoff of the user foot whether sensor unit 8 at the user heel strikes the ground after sensor unit 4 at the user midfoot or forefoot. In one example, if the stride is a desired stride, the amount of time between ground strike of sensor unit 8 and sensor unit 4 is monitored. In one example, the amount of time between landing of sensor unit 4 disposed at the user forefoot and the sensor unit 8 at the heel is measured and utilized to determine the angle at which the user foot leading with the forefoot is striking the ground, where the angle is defined by a line through the heel and forefoot and the ground. The greater the amount of measured time, the greater the angle at which the user foot is striking the ground, indicating that the user is running with a stride emphasizing running on the forefoot or "ball" of the user foot. A look-up table matching time between strikes and landing angle may be pre-loaded at the manufacturer and based on tests of various athletes of varying ability. Thus, the user may track their progress in increasing the angle of foot strike if the user desires to run with a stride emphasizing forefoot first striking. Using the measured time between strikes, the relative position of the user heel, midfoot, and forefoot in the air relative to the ground is determined prior to striking the ground.

In yet another example, the system is configured to track and determine whether and the extent to which the user has improved their stride, including reducing their amount of overstride, relative to when they began a training cycle (e.g., a period of time in which the user is attempting to reduce their overstride) using sensor unit 4. At the beginning of the training cycle, the user is instructed to run with their normal or ordinary running motion. This run may be referred to as a "baseline run", and is an example type of learning mode. For example, the baseline run may be short (e.g., a few seconds or minutes), or long (e.g., several miles). The baseline run may be one of the typical runs that a user may do as part of their running schedule. In one example, the user is instructed to run at a particular speed which is monitored. In one example, the speed is tracked with sensor unit 4. In a further example, the speed is tracked utilizing a GPS unit. Also monitored during the baseline run is the user step cadence (i.e., the baseline cadence) and the user stride length (i.e., baseline stride length).

The output signal of sensor unit 4 during this baseline run is monitored and processed to generate a baseline overstride profile. This baseline overstride profile may be an average over the entire time period of the baseline run. The baseline overstride profile may, for example, be the accelerometer output signal similar to that shown in FIG. 6, an average thereof, or the results of analysis of such an accelerometer output signal to identify select indicia from the signal plot. In one example, the landing of various portions of the user foot, including the heel and the midfoot or forefoot are identified in the plot. A baseline data set is generated and stored in memory 49 including the baseline overstride profile, baseline cadence, and baseline stride length. In one example, the overstride profile cadence, and stride length are correlated to the speed of the baseline run, which is also included in the baseline data set.

During the training cycle, a user running activity is monitored to identify whether the user has reduced their amount of overstride. In one example, the user running activity is performed at the same approximate constant speed as the baseline run. The output signal of sensor unit 4 is processed to generate a current overstride profile. The current overstride profile is compared to the baseline overstride profile to determine whether the user has reduced the amount of overstride relative to the start of the training cycle.

In one example, an analysis algorithm processes the baseline overstride profile to determine a baseline overstride extent. The analysis algorithm processes the current overstride profile to determine a current overstride extent, and compares the current overstride extent to the baseline overstride extent to determine whether the user has reduced the amount of overstride.

In one example, the analysis algorithm is generated based on an analysis of output signals corresponding to a range of motion profiles ranging from severe overstriding to zero overstriding with any number of motion profiles in between. Indicia from a profile being analyzed can be matched to one of the range of motion profiles using pattern matching. The range of motion profiles may be generated empirically across multiple users and processed at the manufacturer to create the analysis algorithm that is stored in the system. The system may output an indication to the user of whether the user is running with improved overstride or not.

Advantageously, in order to track improvement of the user stride, the user need only run with their normal and ordinary stride at the beginning of the training cycle. In one example, during the learning phase at the beginning of the training cycle, the user is prompted to run with their normal and ordinary stride. The user normal and ordinary stride is designated as corresponding to a user baseline overstride motion. Thus, since the user need not modify their stride, the user can easily and therefore accurately perform the baseline overstride motion forming the basis of the baseline overstride motion profile. Furthermore, since the baseline overstride motion profile is specific to the user, any subsequent running activity is analyzed not only to determine whether the user is overstriding and the extent to which the user is overstriding, but also whether the user has reduced their amount of overstriding. For certain runners, this is particularly advantageous because it may not be possible for a runner to completely eliminate overstride from their running, or it may not be possible to reduce the amount of overstriding below a certain fixed amount. For these runners, what is desired is to determine whether the user has reduced their overstriding.

In yet another example, the baseline cadence and baseline stride length taken together are correlated to a user overstride at a particular speed. The inventor has recognized that detection of an increase in cadence or a decrease in stride length for a same given speed indicates that the user has reduced their overstride. During the training phase, a user running activity is monitored to identify the current user cadence and current stride length. The user is directed to run at a same given speed as that during the baseline run. The system determines whether for a same speed the user has reduced their amount of overstride by determining whether the user has increased their cadence or decreased their stride length relative to the baseline cadence and baseline stride length.

In a variation of the immediately preceding embodiment, in addition to performing the baseline run using an ordinary and normal stride, the user is directed to run with a goal stride motion (e.g., non-overstriding or reduced overstride motion) by landing on the midfoot or forefoot. This run may be referred to as a "goal stride run", and is an example type of learning mode. In one example, the user is instructed to run at a particular speed which is monitored. Also monitored during the goal stride run is the user step cadence (i.e., the goal cadence) and the user stride length (i.e., goal stride length). In one example, the system confirms that the user is properly running using a goal stride by determining whether the goal cadence is higher than the baseline cadence and the goal stride length is less than the baseline stride length, thereby increasing the reliability of the goal stride profile.

The output signal of sensor unit 4 during this goal stride run is monitored and processed to generate a goal stride profile in a manner similar to that described above for the baseline overstride profile. A goal stride data set is generated including the goal stride profile, goal cadence, and goal stride length. In one example, the goal profile, cadence, and stride length are correlated to the speed of the goal stride run, which is also included in the goal stride data set.

During the training cycle, a user running activity is monitored to identify whether the user has reduced their amount of overstride. In one example, the user running activity is performed at the same approximate constant speed as the baseline run and the goal stride run. The output signal of sensor unit 4 is processed to generate a current overstride profile. The current overstride profile is analyzed to determine whether the user has reduced the amount of overstride relative to the start of the training cycle.

In one example, an analysis algorithm processes the current overstride profile to identify whether and where the current overstride profile falls between the baseline overstride profile and the goal stride profile to determine the extent of overstride and amount of improvement from the baseline overstride profile. The current cadence is also monitored and analyzed to see whether and where it falls between the baseline cadence and the goal cadence. Similarly, the current stride length is also monitored and analyzed to see whether and where it falls between the baseline stride length and the goal stride length.

In yet another example, the system is configured to track and determine whether and the extent to which the user has improved their stride, including reducing their amount of overstride, relative to when they began a training cycle (e.g., a period of time in which the user is attempting to reduce their overstride) using both sensor unit 4 and sensor unit 8. At the beginning of the training cycle, the user is instructed to run with their normal or ordinary running motion. This run may be referred to as a "baseline run", and is an example type of learning mode. For example, the baseline run may be short (e.g., a few seconds or minutes), or long (e.g., several miles). The baseline run may be one of the typical runs that a user may do as part of their running schedule. In one example, the user is instructed to run at a particular speed which is monitored. In one example, the speed is tracked with sensor unit 4. In a further example, the speed is tracked utilizing a GPS unit.

The output of sensor unit 4 and sensor unit 8 are processed to generate a baseline overstride profile by determining a baseline time between a heel strike and the midfoot or forefoot strike. This baseline time is an average time across all the foot strikes during the measured baseline run.

The extent of overstriding is determined by measuring the time between the heel strike and the midfoot or forefoot strike, with a greater amount of time indicating a larger amount of overstriding. By tracking this time, the system can determine if the user has reduced the amount they are overstriding relative to when they first began the training cycle. Thus, the system tracks not only whether the user is overstriding or not overstriding, but the extent to which the user is overstriding. Thus, even if the user continues to overstride as the training cycle progresses, whether the user has improved their stride (i.e., reduced the amount of overstride) is determined and can be output to the user as positive feedback.

During the training cycle, a user running activity is monitored to identify whether the user has reduced their amount of overstride. In one example, the user running activity is performed at the same approximate constant speed as the baseline run. The output signal of sensor unit 4 and sensor unit 8 are processed to generate a current overstride profile by determining the current time between a heel strike and the midfoot or forefoot strike.

The current overstride profile is compared to the baseline overstride profile to determine whether the user has reduced the amount of overstride relative to the start of the training cycle by determining whether the measured current time is less than the baseline time between the heel strike and the midfoot or forefoot strike.

In one example, a system for athletic training includes a first foot sensor operable for coupling to a heel portion of a user foot and configured to generate a first output signal corresponding to a user heel motion, a second foot sensor operable for coupling to a midfoot or forefoot portion of the user foot and configured to generate a second output signal corresponding to a midfoot or forefoot motion, and a processing system configured to compare the first output signal corresponding to the user heel motion to the second output signal corresponding to the midfoot or forefoot motion. For example, the first sensor is a first inertial sensor (e.g., an accelerometer) and the second sensor is a second inertial sensor (e.g., an accelerometer). In one example, the processing system is further configured to process the first output signal to identify the user heel motion including a heel strike on a surface and the process the second output signal to identify the user midfoot or forefoot motion including a midfoot or forefoot strike on a running surface, the processing system further configured to measure a time period between the heel strike and the midfoot or forefoot strike.

In one example, the processing system is further configured to process the first output signal to identify the user heel motion comprising a forward motion in the air in a direction of user locomotion followed by a heel strike on a surface and the process the second output signal to identify the user midfoot or forefoot motion comprising a forward motion in the air in the direction of user locomotion followed by a midfoot or forefoot strike on a running surface, the processing system further configured to measure the time between and determine a temporal order of the heel strike and the midfoot or forefoot strike. In one example, the processing system identifies a foot strike as an overstride strike upon a determination that the heel strike occurs before the midfoot or forefoot strike greater than a threshold amount of time.

In one example, a method includes generating a first sensor output signal responsive to forward movement of a heel portion of an athlete foot in a stepping direction, the forward movement of the heel portion comprising a heel strike on a running surface, generating a second sensor output signal responsive to a forward movement of a midfoot or forefoot portion of the athlete foot in a stepping direction, the forward movement of the midfoot or forefoot portion of the athlete foot comprising a midfoot or forefoot strike on the running surface, and analyzing the first sensor output signal and the second sensor output signal to measure the amount of time between the heel strike and the midfoot or forefoot strike on the running surface.

In one example, a system for analyzing a foot strike of a person running in a forward direction on a surface including a first sensor to be supported in relation to a heel portion of a foot of the person, the first sensor configured and arranged to output a first sensor output signal in response to movement of the heel portion during running, a second sensor to be supported in relation to a midfoot or forefoot of the person, the second sensor configured and arranged to output a second sensor output signal in response to movement of the midfoot or forefoot during running, and a processor configured to receive and analyze the first sensor output signal and the second sensor output signal to determine a difference in motion between the heel portion and the midfoot or forefoot portion. In one example, the difference in motion is the time between the heel portion striking a running surface prior to the midfoot or forefoot portion.

In one example, a system for foot motion sensing includes a first motion sensor operable to measure first sensor data on motion of a first foot part, a second motion sensor operable to measure second sensor data on motion of a second foot part, and a processor in communication with the first motion sensor and the second motion sensor to receive and process the first sensor data and the second sensor data to produce a first measured motion profile and a second measured motion profile. In one example, the measured motion is the direction of acceleration of the user foot, including whether the direction is rearward, upward, or forward in the air relative to the direction of locomotion. In one example, the processor is configured to analyze the first measured motion profile and the second measured motion profile to output a determination of a surface strike order of the first foot part and the second foot part.

Figure 9:
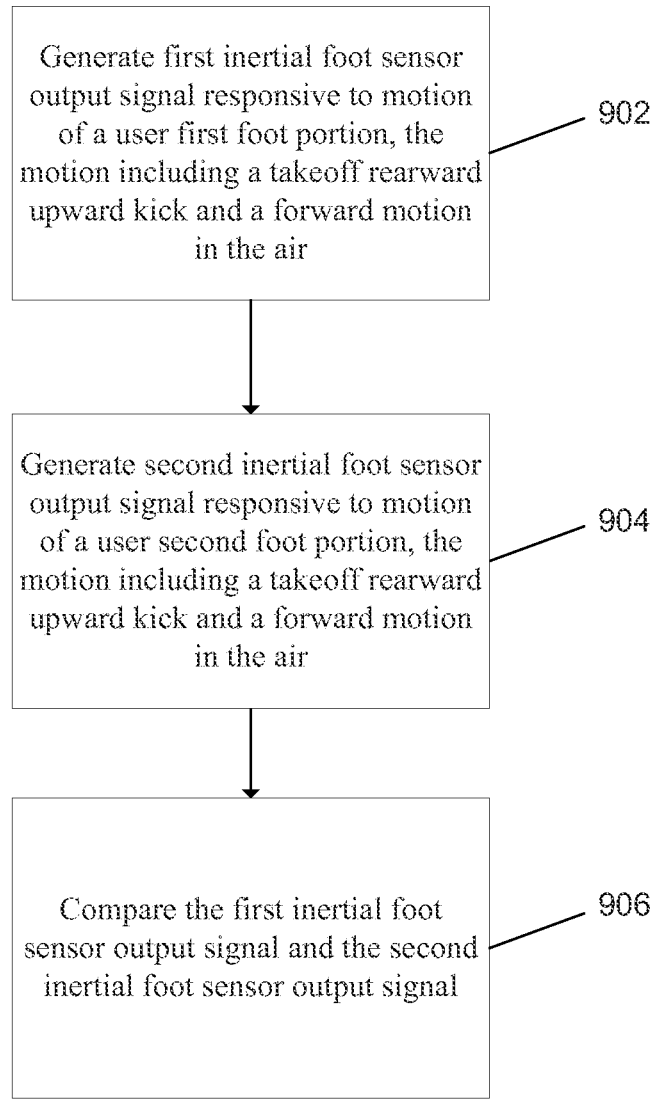
FIG. 9 is a flow diagram illustrating a method for athletic performance monitoring in one example.

FIG. 9 is a flow diagram illustrating a method for athletic performance monitoring in one example. At block 902, a first inertial foot sensor output signal is generated responsive to motion of a user first foot portion, the motion including a takeoff rearward upward kick and a forward motion in the air. At block 904, a second inertial foot sensor output signal is generated responsive to motion of a user second foot portion, the motion including a takeoff rearward upward kick and a forward motion in the air. At block 906, the first inertial foot sensor output signal and the second inertial foot sensor output signal are compared.

Figure 10:
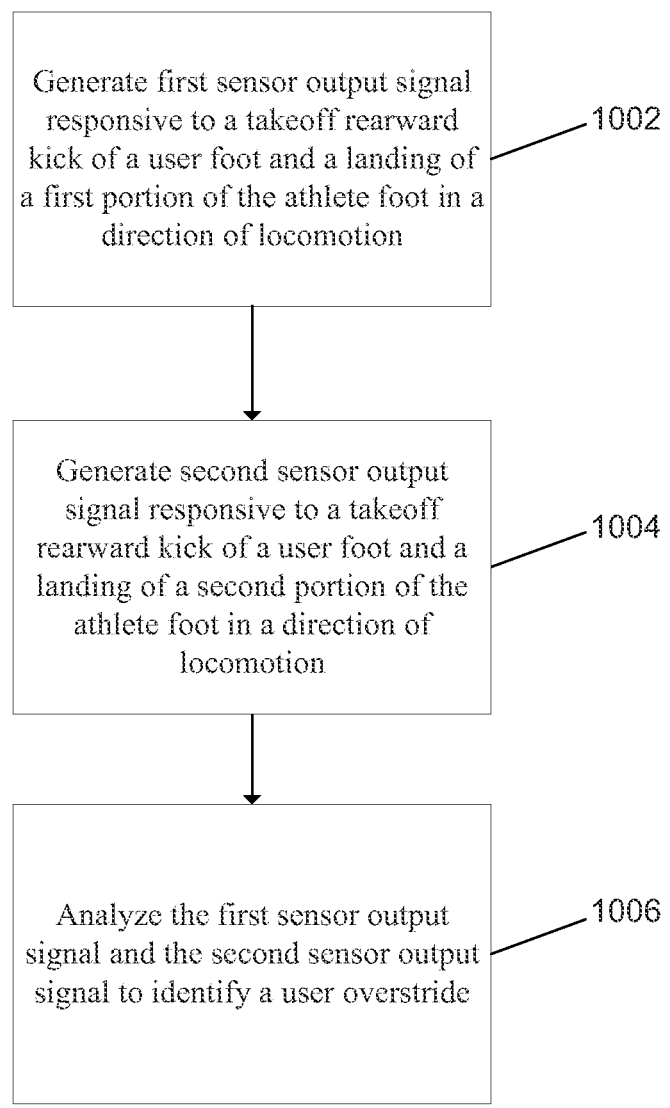
FIG. 10 is a flow diagram illustrating a method for athletic performance monitoring to detect user overstride in one example.

FIG. 10 is a flow diagram illustrating a method for athletic performance monitoring to detect user overstride in one example. At block 1002, a first sensor output signal is generated responsive to a takeoff rearward kick of a user foot and a landing of a first portion of the athlete foot in a direction of locomotion. At block 1004, a second sensor output signal is generated responsive to a takeoff rearward kick of a user foot and a landing of a second portion of the athlete foot in a direction of locomotion. At block 1006, the first sensor output signal and the second sensor output signal are analyzed to identify a user overstride.

Figure 11A:
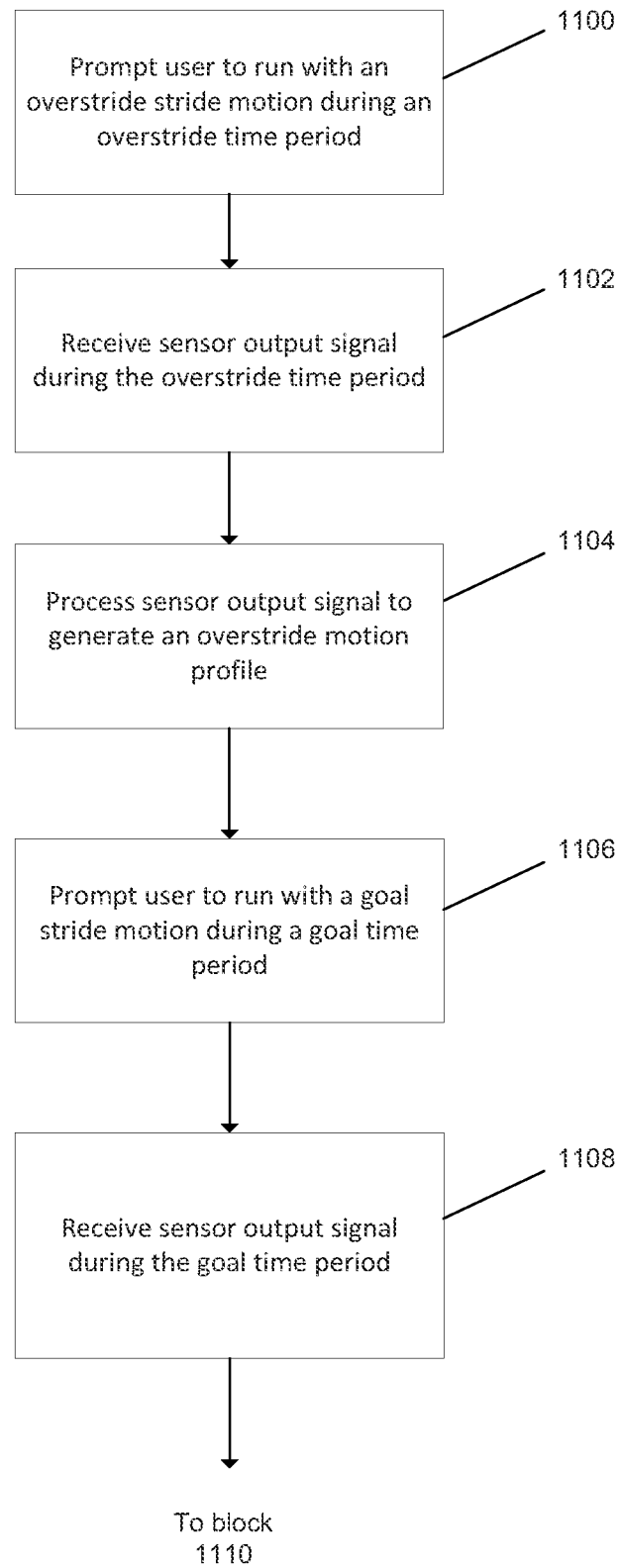
FIGS. 11A and 11B are a flow diagram illustrating a method for athletic performance monitoring in a further example.
Figure 11B:
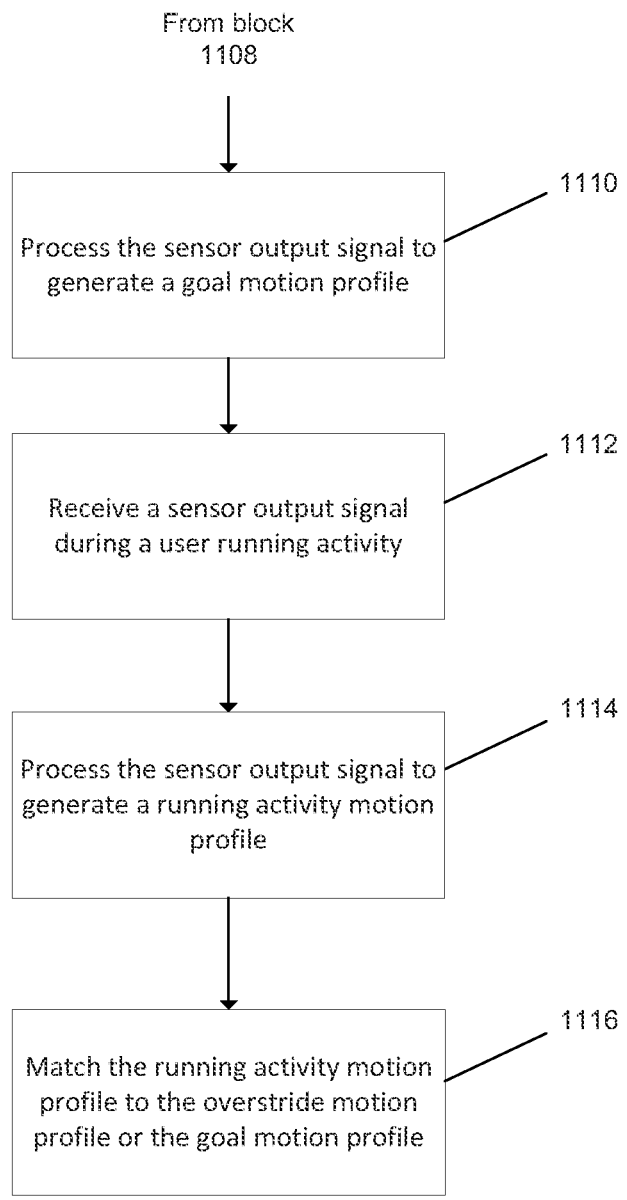

FIGS. 11A and 11B are a flow diagram illustrating a method for athletic performance monitoring in a further example. At block 1100, a user is prompted to run with an overstride motion during an overstride time period. At block 1102, a sensor output signal during the overstride time period is received. At block 1104, the sensor output signal is processed to generate an overstride motion profile. At block 1106, a user is prompted to run with a goal stride motion during a goal time period. At block 1108, a sensor output signal during the goal time period is received. At block 1110, the sensor output signal is processed to generate a goal motion profile. At block 1112, a sensor output signal during a user running activity is received. At block 1114, the sensor output signal is processed to generate a running activity motion profile. At block 1116, the running activity motion profile is matched to the overstride motion profile or the goal motion profile.

Figure 12:
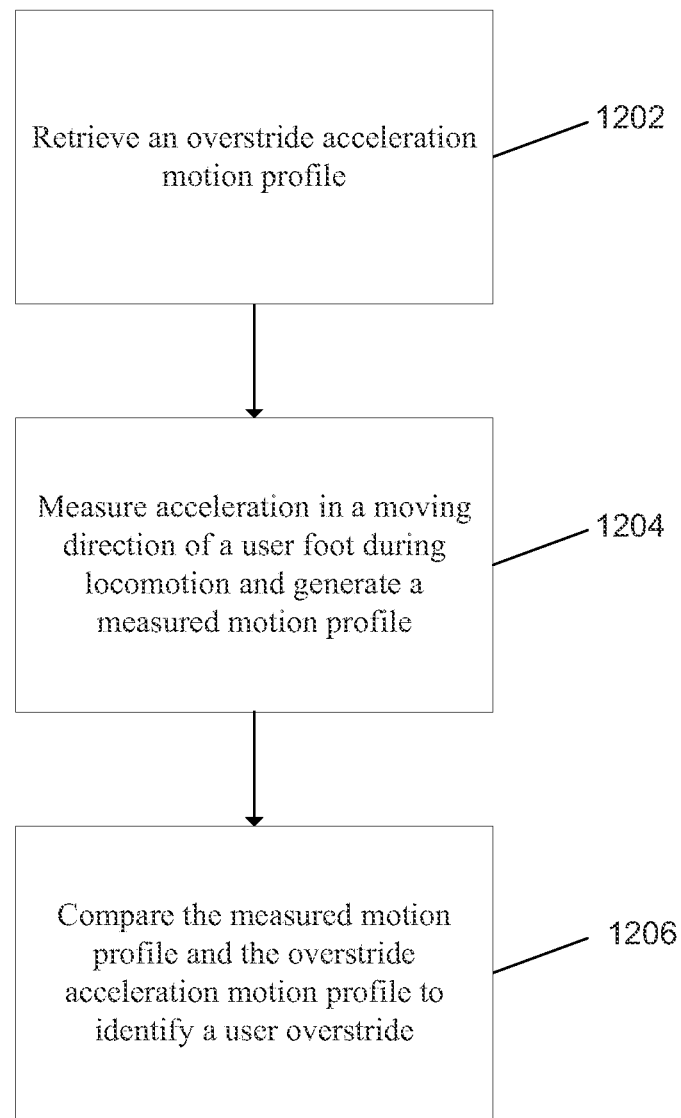
FIG. 12 is a flow diagram illustrating a method for athletic performance monitoring to detect user overstride in a further example.

FIG. 12 is a flow diagram illustrating a method for athletic performance monitoring to detect user overstride in a further example. At block 1202, an overstride acceleration motion profile is retrieved. At block 1204, an acceleration in a moving direction of a user foot during locomotion is measured and a measured motion profile is generated. At block 1206, the measured motion profile and the overstride acceleration motion profile are compared to identify a user overstride.

Figure 13:
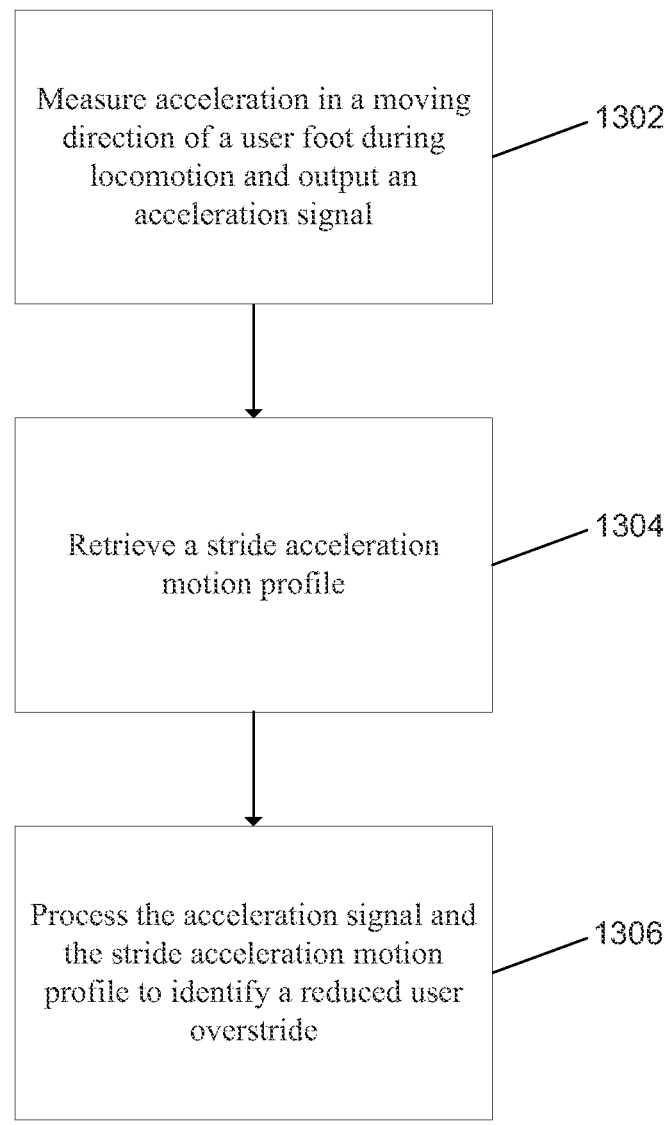
FIG. 13 is a flow diagram illustrating a method for athletic performance monitoring to identify a reduced user overstride in one example.

FIG. 13 is a flow diagram illustrating a method for athletic performance monitoring to identify a reduced user overstride. At block 1302, an acceleration in a moving direction of a user foot during locomotion is measured and an acceleration signal is output. At block 1304, a stride acceleration motion profile is retrieved. In one example, the stride acceleration motion profile is generated from a prior locomotion by the user. In one example, the stride acceleration motion profile is an undesired stride acceleration motion profile (e.g., it corresponds to a user overstride motion). In one example, the stride acceleration motion profile corresponds to a normal running motion of the user. At block 1306, the acceleration signal and the stride acceleration motion profile are processed to identify a reduced user overstride. In one example, the acceleration signal is processed to calculate an average cadence and an average stride length for a same speed. In one example, the acceleration signal is matched with an acceleration motion profile from a plurality of acceleration motion profiles associated with the user to identify a user stride motion.

In one example, a system for monitoring a user running stride includes a first sensor configured to monitor a first user motion parameter such as user speed during a user running activity and provide a first sensor output and a second sensor configured to monitor a second user motion parameter during the user running activity and provide a second sensor output. The system further includes a processor configured to process the first sensor output and the second sensor output to determine a processed user parameter associated with both the first sensor output and the second sensor output. In one example, the processed user parameter is determined in real time, i.e., during the user running activity.

In one example, a method for monitoring a user running stride includes receiving a first sensor output data to monitor a first user motion parameter during a user running activity, receiving a second sensor output data to monitor a second user motion parameter during the user running activity, and processing the first sensor output data and the second sensor output data to determine a processed user parameter associated with both the first sensor output data and the second sensor output data. In one example, a computer readable storage memory stores instructions that when executed by a computer cause the computer to perform this recited method for monitoring a user running stride.

In one example, a system for determining an improved user stride includes a first sensor providing a first sensor output, a second sensor providing a second sensor output, and a processor configured to process the first sensor output and the second sensor output to calculate a user motion parameter associated with both the first sensor output and the second sensor output, retrieve a baseline value of the user motion parameter, and identify an improved user stride associated with an increase in the user motion parameter relative to the baseline value.

In one example, a method for determining an improved user stride includes processing a first sensor output and a second sensor output to calculate a user motion parameter associated with both the first sensor output and the second sensor output, retrieving a baseline value of the user motion parameter, and identifying an improved user stride associated with an increase in the user motion parameter relative to the baseline value. In one example, a computer readable storage memory stores instructions that when executed by a computer cause the computer to perform this recited method for determining an improved user stride.

In one example, a system for determining an improved user stride includes a first sensor configured to monitor a first user motion parameter during a user running activity and provide a first sensor output, a second sensor configured to monitor a second user motion parameter during the user running activity and provide a second sensor output, and a processor. The system further includes a memory storing a stride analysis program configured to process the first sensor output and the second sensor output to determine a first user motion parameter in excess of a threshold value and identify an improved user stride associated with both a decrease in the first user motion parameter and an increase in the second user motion parameter.

In one example, a method for determining an improved user stride includes detecting a first user motion parameter in excess of a threshold value, determining a second user motion parameter, and identifying an improved user stride associated with both a decrease in the first user motion parameter and an increase in the second user motion parameter. In one example, a computer readable storage memory stores instructions that when executed by a computer cause the computer to perform this recited method for determining an improved user stride.

In one example, a method for determining an improved user stride includes detecting a first user motion parameter in excess of a threshold value, determining a second user parameter, and identifying an improved user stride associated with both a decrease in the first user motion parameter and a maintenance of the second user motion parameter at an approximately same value. In one example, a computer readable storage memory stores instructions that when executed by a computer cause the computer to perform this recited method for determining an improved user stride. As used herein, the terms determining and monitoring may be utilized interchangeably.

In one example, a system for instructing a runner includes a first sensor configured to monitor a first user motion parameter during a user running activity and provide a first sensor output, a second sensor configured to monitor a second user motion parameter during the user running activity and provide a second sensor output, and a processor. The system further includes a memory storing a stride analysis program configured to process the first sensor output and the second sensor output to detect the second user motion parameter in excess of a threshold value and responsively prompt the runner to decrease the second user motion parameter and increase the first user motion parameter.

In one example, a method for instructing a runner includes monitoring a first user motion parameter, detecting a second user motion parameter in excess of a threshold value, and prompting the runner to decrease the second user motion parameter and increase the first user motion parameter. In one example, a computer readable storage memory stores instructions that when executed by a computer cause the computer to perform this recited method for instructing a runner.

In one example, a method for diagnosing a runner stride motion defect includes determining a foot motion parameter associated with movement in a rearward direction opposite a direction of running and comparing the foot motion parameter to a threshold value to identify an excessive foot motion.

In one example, a method for determining an improved user stride includes processing a speed sensor output and a stride rate sensor output to calculate a current stride rate as a function of speed, retrieving baseline data associated with a baseline stride rate as a function of speed, and identifying an improved user stride associated with an increase in the current stride rate relative to the baseline stride rate for a same speed. In one example, a computer readable storage memory stores instructions that when executed by a computer cause the computer to perform this recited method for determining an improved user stride.

A runner's stride may have several defects (also referred to herein as "stride inefficiencies") which detract from the efficiency of his stride. Common stride defects include overstriding, excessive vertical displacement, and excessive rearward foot motion. Stride defects generally result in wasted energy or wasted motion and greater impact stress on the runner's legs and body. Eliminating or limiting these defects to improve the runner's stride efficiency will allow the runner to run farther, faster, and/or with less injury. Finally, an efficient stride enables the runner to have a more compact stride, as discussed below. As a result, methods and apparatuses are needed to identify stride defects and to determine whether the runner has decreased or eliminated any identified defects.

Furthermore, continuous, real time monitoring of stride efficiency is critical because user form often deteriorates as the runner tires, as towards the end of a race. Thus, though the user may be able to maintain proper form early in a run or race (e.g., as confirmed by systems and methods described herein), systems and methods are needed to detect breakdowns in stride efficiency during latter stages of the run so that the user can be prompted to make corrections.

Compact Stride

Relative to casual runners, betters runners typically have a shorter stride length for a given same speed. This will be referred to herein as having a "compact stride". Stride defects limit the compactness of a runner's stride, and since better runners have fewer stride defects, better runners have a more compact stride. Shorter strides for a given same speed necessarily correlates to a higher stride rate (cadence) for that given speed by better runners.

In other words, a more compact stride is a more efficient stride. However, whether a user has a compact stride is specific to each user based on their particular body physiology. As a result, the inventor has recognized that it would be useful to have methods and apparatuses to measure the compactness of a user stride. For example, methods and apparatuses are needed to measure stride length as a function of speed. The inventor has recognized that an improvement in the compactness of a user stride is an improvement in the efficiency in the user stride. As a result, it would be useful to have methods and apparatuses for determining whether a user has improved the compactness of their stride.

In one example, a system for monitoring a user running stride includes a first sensor configured to monitor a first user motion parameter during a user running activity and provide a first sensor output and a second sensor configured to monitor a second user motion parameter during the user running activity and provide a second sensor output. In one example, the first sensor may be implemented with sensor unit 2 and the second sensor may be implemented with sensor unit 4, as described above in reference to FIG. 1 and FIG. 2. The system further includes a processor configured to process the first sensor output and the second sensor output to determine a processed user parameter associated with both the first sensor output and the second sensor output. In one example, the processor may be implemented at controller 18 of sensor unit 2 as shown in FIG. 2. In other words, the processed user parameter utilizes both the first sensor output and the second sensor output, e.g., a global positioning system unit output and a foot sensor output.

In one example, the first sensor (e.g., sensor unit 2) is a speed sensor configured to monitor a user speed during the user running activity, such as a global positioning system unit. In one example, the second sensor (e.g., sensor unit 4) comprises a stride rate sensor configured to monitor a user stride rate during the user running activity, such as an inertial sensor worn on the user foot.

In one example, the processed user parameter is a user stride rate as a function of a user speed. In one example, the processed user parameter is an average stride rate for a same user speed. In one example, the processed user parameter is an average stride length for a same user speed. In one example, the processed user parameter is an average time-in-the-air for a same user speed.

In one example, the processed user parameter is an indicator of an efficiency of the runner stride. For example, the indicator of the efficiency of the runner stride is a measure of stride compactness.

In one example, a system for determining an improved user stride includes a first sensor providing a first sensor output, a second sensor providing a second sensor output, and a processor configured to process the first sensor output and the second sensor output to calculate a user motion parameter associated with both the first sensor output and the second sensor output, retrieve a baseline value of the user motion parameter, and identify an improved user stride associated with an increase in the user motion parameter relative to the baseline value. In one example, the first sensor may be implemented with sensor unit 2 and the second sensor may be implemented with sensor unit 4, as described above in reference to FIG. 1 and FIG. 2.

In one example, the first sensor output is a speed sensor output, the second sensor output is a stride rate, and the user motion parameter is a stride rate as a function of speed. In one example, the improved user stride is a stride with reduced overstride.

FIG. 15 illustrates a table 1500 having split, average page, and average run cadence data for a first run performed by a user. Each split represents a covered distance (e.g., 1 mile), with the average page and average stride rate given for each split. In other words, the average stride rate shown is the average for a distance. For example, during split 1 (e.g., mile 1), the average pace was 8:26 minutes per mile, and the average stride rate was 78 steps per minute. For example, average pace data may be calculated from data output from a speed sensor at sensor unit 2. Average run cadence (i.e., stride rate) may be calculated from data output from sensor unit 4.

FIG. 16 illustrates a table 1600 where the data shown in table 1500 has been processed to show a use stride rate as a function of speed (e.g., pace). Stride rate as a function of speed is a parameter associated with both a stride rate sensor output and a speed sensor output. For example, the data in table 1500 has been sorted and processed to identify that when the user had an average pace of 6:50, his stride rate was 87, 88, and 88, producing an average stride rate of 87.67. In other words, the user had an average stride rate of 87.67 when he was running a same speed of 6:50 during the first run.

FIG. 17 illustrates a table 1700 having split, average page, and average run cadence data for a second run performed by a user. For example, the second run may be performed some time later in the training cycle than the first run to see if the runner has improved. Thus, the first run serves as a baseline value.

FIG. 18 illustrates a table 1800 where the data shown in table 1700 has been processed to show a use stride rate as a function of speed (e.g., pace). For example, the data in table 1700 has been sorted and processed to identify that when the user had an average pace of 6:50, his stride rate was 90, 90, and 90, producing an average stride rate of 90.

FIG. 19 illustrates a table 1900 where the data in table 1600 and table 1800 has been processed to show changes in stride rate from the first run to the second run based on a same average pace. For example, when the runner had an average pace of 6:50 minutes/mile the runner increased his stride rate from 87.67 steps per minute during the first run to 90 steps per minute during the second run. Monitoring of the second run may be performed in real time during the run or after completion of the second run.

In one example, a method for monitoring a user running stride includes receiving a first sensor output data to monitor a first user motion parameter during a user running activity, receiving a second sensor output data to monitor a second user motion parameter during the user running activity, and processing the first sensor output data and the second sensor output data to determine a processed user parameter associated with both the first sensor output data and the second sensor output data.

In one example, the first sensor output data is speed data, the second sensor output data is stride rate data, and the processed user parameter is a user stride rate as a function of user speed. In one example, the stride rate as a function of user speed is monitored in real time during a user run. In a further example, the stride rate as a function of user speed can be calculated at the end of a run using all of the gathered data.

In one example, the processed user parameter is an average stride rate for a same user speed, an average stride length for a same user speed, or an average time-in-the-air for a same user speed.

In one example, the processed user parameter is an indicator of an efficiency of the runner stride. For example, the indicator of the efficiency of the runner stride is a measure of stride compactness.

In one example, a method for determining an improved user stride includes processing a first sensor output and a second sensor output to calculate a user motion parameter associated with both the first sensor output and the second sensor output, retrieving a baseline value of the user motion parameter, and identifying an improved user stride associated with an increase in the user motion parameter relative to the baseline value.

In one example, the first sensor output is a speed sensor output, the second sensor output is a stride rate sensor, and the user motion parameter is a stride rate as a function of speed.

In one example, the improved user stride is a stride with reduced overstride.

In one example, a method for determining an improved user stride includes processing a speed sensor output and a stride rate sensor output to determine a current stride rate as a function of speed, retrieving baseline data associated with a baseline stride rate as a function of speed, and identifying an improved user stride associated with an increase in the current stride rate relative to the baseline stride rate for a same speed. In one example, the calculated and baseline stride rates may be averaged values. In one example, the current stride rate as a function of speed is calculated and monitored in real time during a run. For example, if the user is currently running at 6:50 minutes/mile, the current stride rate is monitored and correlated to this speed. In one example, the current stride rate is then compared to a baseline stride rate for pace 6:50. For example, the baseline stride rate is retrieved from memory. For example, the baseline stride rate may be retrieved from a table such as table 1600. Real time monitoring is advantageous because runner form often deteriorates toward the latter stages of a run. As such, it would be beneficial for the system to determine and notify the runner stride if his stride rate for a given speed falls below a baseline value or threshold level at any time during the run. Similarly, real time monitoring allows the system to calculate if the user is running with improved stride compactness (i.e., an improved stride rate for a given speed) relative to a baseline value and notify the user in real time during the run if they are doing so, thereby providing positive feedback.

Thus, the inventor has further recognized that stride compactness can be measured by tracking stride rate as a function of speed since shorter strides for a given same speed necessarily correlates to a higher stride rate (cadence). By measuring stride rate for a given speed and determining if it has increased relative to a prior measurement at the same speed, it is determine whether the user has increased stride compactness (i.e., reduced their stride length for a given speed). It is noted that better runners have a long stride length when they are running at very fast speeds. What is desired to achieve an efficient stride is not simply that the runner decrease his stride length, but that the runner decrease his or her stride length while maintaining the same speed. Thus, the system advantageously determines whether a runner has increased his or her stride rate (i.e., reduced their stride length) without decreasing his or her speed.

Alternatively, the system can determine if the runner has undesirably decreased his or her stride compactness. This is particularly advantageous for monitoring a user for deteriorating form during a race or long run. For example, using real time monitoring of the current stride compactness relative to a baseline value, the user can be informed if his stride compactness has decreased.

It is important for the user to maintain stride compactness whatever speed the user is running. The user naturally wants to increase their speed if they attempt to increase their cadence. One advantage of the described system is that it monitors the compactness of the runner's stride whatever the current speed of the runner. This is important because the user may have a compact stride at one speed, but not when they increase their speed (i.e., at the increased speed, there is a room for improvement in the stride compactness). Also, the system advantageously monitors efficiency for the runner, which the runner may not need or be able to determine on their own for shorter distances. However, the efficiency/compactness of the stride is important for the user running longer distances requiring greater stamina, as the user will have greater remaining energy towards the end of the run if they have an efficient/compact stride.

Furthermore, the inventor has recognized that measuring an increase in a runner's stride compactness is an advantageous way to measure whether the user has reduced overstride. One of the biggest factors affecting the compactness of the runners stride is where the runner's foot lands relative to the runner's torso (e.g., the runner's center of gravity). If the runner lands his foot beneath his center of gravity, this will enable the runner to achieve a more compact stride. This is true for a variety of reasons. Landing the foot beneath the body's center of gravity provides more stability to the runner than landing the foot in front of the body. Upon landing, less time and energy is required stabilizing the leg and body in preparation for the next step. Furthermore, as a result, the runner can push off more quickly and the amount of time the runner foot must spend on the ground is reduced, thereby allowing the runner to improve his or her stride rate for a given speed. Landing the foot beneath the runner's center of gravity allows the runner to run longer (i.e., farther) because less energy is required to run at a given speed because energy is not wasted with each step (e.g., due to loss of elastic recoil energy or energy wasted to balance the runner).

Furthermore, landing the foot beneath the runner's center of gravity allows the runner to run faster because the runner is able to push off more quickly and forcefully enabling a longer stride length at a same or increased stride rate. An efficient stride allows a runner to either increase his stride rate while maintaining the same stride length or increase his stride length while maintaining the same stride rate, both of which result in greater speed. Thus, although the system measures improvements in stride compactness, which is based on a same runner speed, an improved stride compactness will enable the runner to increase his speed.

As described previously, landing the runner's foot in front of the body's center of gravity instead of beneath it is often referred to as "overstriding". Thus, the inventor has recognized that by measuring/monitoring the compactness of a runner's stride, one can use this as an accurate indicator or proxy to determine if the runner is landing his or her foot beneath their body's center of gravity (i.e., whether the runner is overstriding). Thus, whether a runner has reduced their overstriding can be determined by measuring whether the runner has increased the compactness of their stride.

The inventor has recognized this method of measuring overstriding is advantageous in that it may identify user overstriding where other methods fail to do so. For example, this method of measuring of overstriding is not tied whether the user lands heel first to or midfoot first. Although a runner striking heel first is one indicator of overstriding, a runner may still be overstriding even if he or she lands midfoot or forefoot first, as in the case where the runner is "leaping" forward with each step and landing midfoot/forefoot first in front of the body. Furthermore, this method determines overstriding by correlating it to stride compactness, a variable directly related to improving how far and fast one can run. Other stride defects which may adversely affect a runner's stride compactness include excessive vertical displacement and/or foot motion.

Prompting the User and Measuring Improvement in User Stride

Because it is difficult for runners to modify their running form, the inventor recognizes that it is difficult for a runner to improve the compactness of their stride, or reduce their stride defects in general. In order to improve stride compactness, the runner must reduce their stride length while maintaining the same speed (or, equivalently, increase their stride rate while maintaining the same speed). However, the inventor has recognized it is ineffective to simply instruct the user to increase their stride compactness as the runner will not know how to do so. For example, if a runner simply attempts to increase their cadence, the runner will have a tendency to do one of two things, neither of which increases stride compactness: (1) the runner will simply increase their speed by increasing their cadence while maintaining the same stride length or increasing their stride length, as cadence will naturally increase with increased speed, or (2) the runner may simply decrease their speed by greatly shortening their stride length in order to increase their cadence. By monitoring stride compactness and improvements in stride compactness, the methods and apparatuses described above detect whether a runner has done either of these things.

Furthermore, what are needed are methods and apparatuses to effectively instruct a runner how and/or when to increase their stride compactness, and determine whether they have correspondingly improved their stride. This may involve methods and apparatuses to effectively instruct a runner how and/or when to increase their stride rate or stride length. Furthermore, it is typically the goal of most runners to run with greater speed. What are needed are methods and apparatuses to effectively instruct a runner how or when to run faster and to minimize the increase in energy expenditure required for the user to run faster, and to determine whether they have correspondingly improved their stride. What is desired is the ability to run with both increased speed and endurance.

Other factors affecting the compactness of the runner's stride, in addition to overstriding, include stride inefficiencies such as excessive vertical displacement relative to horizontal displacement and excessive/unnecessary rearward foot motion. These stride defects not only limit the runner's stride compactness, but also the runner's stamina, speed, their stride rate, and their stride length.

Both too much vertical displacement and excessive rearward foot motion result in excessive time in the air of the foot. Excessive time in the air limits the efficiency of the runner stride. However, simply prompting the runner to decrease the amount of time in the air is ineffective if the runner does not know how to reduce their air time. In order to know how to reduce their airtime, the runner must be notified of their type of stride defect (e.g., whether it is due to excessive vertical displacement, excessive rearward foot motion, overstriding, or some other reason) so they can consciously attempt to limit the identified defect. Furthermore, the inventor has recognized that the time during which the runner is attempting to limit the identified defect is the ideal and most beneficial time for the runner to attempt to improve their stride compactness, stride rate, stride length, or speed. This is true because reducing the stride defect enables the runner to improve, their stride compactness, stride rate, stride length, or speed. By encouraging/prompting the runner to improve one or more of these factors simultaneously with reducing the identified stride defect, the runner feels and sees immediate benefits to the reduction of the identified stride defect. Feeling and seeing immediate benefits to the reduction of the identified stride defect operates to reinforce the act of reducing the stride defect on a long term basis. Thus, the runner is more easily trained to avoid reverting back to the stride defect during future running. Furthermore, it is natural for the runner to want to redirect the energy that is conserved by reducing or eliminating the stride defect, so the inventor has recognized this as another reason why this is the ideal time for the runner to improve their stride compactness, stride rate, stride length, speed, or other motion parameter.

Furthermore, by re-directing energy that was wasted due to the prior stride defect, the runner is able to improve their stamina. For example, where the user increases their speed, not only does reducing the stride defect enable the runner to more easily increase the speed, it allows the runner to increase their speed with less additional energy than if they had not reduced their stride defect. As a result, the runner can run for longer (i.e., farther) at the higher speed than if they had not reduced the stride defect in conjunction with increasing their speed. In other words, the runner's stamina at the higher speed is improved utilizing the systems and methods described.

In an example where the runner wishes to improve their stride compactness while maintaining the same speed, the runner is also able to run for longer and farther since increases stride compactness increases stride efficiency. For a given amount of energy, a runner with a more efficient stride can run longer and farther.

Thus, the inventor has recognized that by identifying these stride defects, the runner can be prompted as to how and when to increase their stride compactness or speed. In one example, the system identifies a defect, prompts the runner to both reduce or eliminate the identified defect and improve another stride motion parameter. For example, the stride parameter may be stride compactness, stride rate, stride length, or speed. The system then monitors the runner subsequent stride with respect to the stride defect for improvement and monitors the stride motion parameter for improvement. The system may then provide feedback to the runner regarding whether one or both have improved. In a further example, the user has the option of deciding which stride motion parameter to improve.

In one example, a system for instructing a runner includes a first sensor configured to monitor a first user motion parameter during a user running activity and provide a first sensor output, a second sensor configured to monitor a second user motion parameter during the user running activity and provide a second sensor output, and a processor. The system further includes a memory storing a stride analysis program configured to process the first sensor output and the second sensor output to detect the second user motion parameter in excess of a threshold value and responsively prompt the runner to decrease the second user motion parameter and increase the first user motion parameter.

In one example, the first user motion parameter is a measure of stride of compactness, a runner stride rate, or a runner speed and the second user motion parameter is a vertical displacement or foot motion.

In one example, a system for determining an improved user stride includes a first sensor configured to monitor a first user motion parameter during a user running activity and provide a first sensor output, a second sensor configured to monitor a second user motion parameter during the user running activity and provide a second sensor output, and a processor. The system further includes a memory storing a stride analysis program configured to process the first sensor output and the second sensor output to determine a first user motion parameter in excess of a threshold value and identify an improved user stride associated with both a decrease in the first user motion parameter and an increase in the second user motion parameter.

In one example, the first user motion parameter is a vertical displacement or a user foot motion. In one example, the second user motion parameter is a user stride rate, a user stride length, a user speed, or a user stride compactness.

Depending on the desired motion parameter to be monitored, the first sensor and the second sensor may be implemented using one or more of sensor unit 2, sensor unit 4, or sensor unit 6. In one example, the stride analysis program is stored in a memory and executed by a processor at sensor unit 2. In one example, the stride analysis program is further configured to output a prompt to the user to decrease the first user motion parameter and increase the second user motion parameter following determining the first user motion parameter in excess of the threshold value. In one example, the system includes a user interface display, such as at sensor unit 2, wherein the prompt is a text message on the user interface display.

Thus, whether has improved their stride is measured not only whether the runner has reduced or eliminated unnecessary motion, but whether the runner has taken advantage of the resulting benefits and increased another desirable motion parameter.

In one example, the first user motion parameter is a vertical displacement. A runner may be correctly landing his foot beneath his center of gravity, but still have an unnecessarily inefficient stride due to excessive vertical displacement relative to the amount of horizontal displacement. Excessive vertical displacement often manifests itself as a "bouncy" motion where the runner is bouncing up and down. Excessive vertical displacement detracts from stride efficiency because energy is being wasted directing the runner in an upward direction instead of horizontally in the direction of locomotion. Furthermore, the excessive vertical displacement of the runner foot limits the stride rate of the runner because the runner is spending unnecessary time in the air.

It should be noted that a certain amount of vertical displacement is required, and the amount of vertical displacement may increase with increased runner speed. As such, in one example, whether a vertical displacement is excessive is determined based on comparing the amount of vertical displacement to the amount of horizontal displacement. The greater the horizontal displacement, the greater the amount of vertical displacement is permitted before a vertical displacement is deemed excessive.

Using the methods and apparatuses described above, the system measures the runner vertical displacement and/or vertical displacement/horizontal displacement ratio to identify excessive vertical displacement.

In one example, the first user motion parameter is a user foot motion. A runner may be correctly landing his foot beneath his center of gravity, but still have an unnecessarily inefficient stride due to excessive foot motion relative to the amount of horizontal displacement. For example, excessive foot motion may manifest itself as unnecessary height or time in the rearward and upward direction following toe-off. Excessive foot motion detracts from stride efficiency because time and energy is being wasted directing the foot upward in the rearward direction instead of horizontally in the direction of locomotion. Furthermore, the excessive foot motion of the runner foot limits the stride rate of the runner because the runner is spending unnecessary time in the air.

It should be noted that a certain amount of height and time of the foot in the rearward direction is required, and the amount of rearward foot motion may increase with increased runner speed. As such, in one example, whether a foot motion is excessive is determined based on the user speed. The greater the horizontal displacement or speed, the greater the amount of foot motion is permitted before a foot motion is deemed excessive.

Using the methods and apparatuses described above, the system measures the runner rearward foot motion. The measured foot motion is compared to a threshold to identify excessive foot motion. In one example, the threshold is a time threshold which, above which the foot motion is deemed excessive. In a further example, the threshold is a height threshold, above which the foot motion is deemed excessive. In either case, predetermined thresholds may be set using techniques described herein.

Referring again to FIG. 6, periods in which the user's foot is moving rearward in a backward and upward direction following initial toe-off may be identified by monitoring the signal 602 for: (a) characteristics that indicate the foot is airborne combined with period of positive acceleration, or (b) the period of time immediately following toe-off, but prior to movement of the foot in an identified forward direction. The relatively small negative peaks 604 indicates the beginning of a stride which corresponds to the moment the shoe leaves the ground and starts moving rearward and upward (i.e., a toe-off event). The zero crossing 608 after the large negative peak 606 indicates the end of the stride which corresponds to the moment the shoe lands on the ground again (i.e., a foot strike event). Following foot strike, but before toe-off, the user foot is in contact with the ground for a period of time ("foot on ground time"). Following toe-off, but before foot-strike, the user foot is in the air ("foot in air time" or simply "air-time"). The stride time may be measured as the time between zero crossings after the large negative peak 606.

In one example, the threshold value is specific to the user. For example, the system including sensor unit 4 may enter a learning mode whereby the user runs in the desired form for a test interval and the foot motion is measured. In a further example, the threshold value is determined using test measurements of other runners or using established norms and stored by the system prior to use by the runner. In yet another example, the threshold value is set to a specific amount. In yet another example, the threshold value is adjusted in real-time based upon the speed of the user. For example, as the speed of the user increases while running, the threshold value may be adjusted in an upward direction. As the speed of the user decreases while running, the threshold value may be adjusted in a downward direction. As described elsewhere herein, threshold values may be set or determined in a variety of ways, including a learning mode whereby values are set specific to the user and/or preset during manufacturing based on tests of other runners, such as elite runners known to perform at high levels, or based on theoretical calculations.

Again, the amount of adjustment maybe set/calibrated specific to the user based on the learning mode tests at different speeds and/or pre-set during manufacturing. The average foot motion displacement in a rearward direction or the amount of time of the foot in the rearward direction for each stride over a given time or distance interval may be calculated and output to the user in real time or during subsequent workout analysis.

In one example, a method for instructing a runner includes monitoring a first user motion parameter, detecting a second user motion parameter in excess of a threshold value, and prompting the runner to decrease the second user motion parameter and increase the first user motion parameter.

In one example, the first user motion parameter is a measure of stride of compactness, a runner stride rate, or a runner speed, and the second user motion parameter is a vertical displacement or foot motion.

In one example, a method for determining an improved user stride includes detecting a first user motion parameter in excess of a threshold value, determining a second user motion parameter, and identifying an improved user stride associated with both a decrease in the first user motion parameter and an increase in the second user motion parameter.

In one example, the first user motion parameter comprises a vertical displacement or a user foot motion.

In one example, the second user motion parameter comprises a user stride rate, a user stride length, a user speed, or a user stride compactness.

In one example, the threshold value is dependent on a current user speed.

In one example, the method further includes prompting the user to decrease the first user motion parameter and increase the second user motion parameter following detecting the first user motion parameter in excess of the threshold value. For example, prompting the user may include outputting a text message at a wrist worn device or outputting an audible prompt at a head worn device or at the wrist worn device.

In one example, the method further includes monitoring a third user motion parameter, wherein identifying an improved user stride further comprises identifying an increase in the third user motion parameter. For example, the third user motion parameter may be a user stride rate, a user stride length, a user speed, or a user stride compactness.

In one example, the method further includes monitoring a user heart rate, wherein identifying an improved user stride further comprises identifying the user heart rate to be approximately the same or less than a value prior measured prior to the decrease in the first user motion parameter and the increase in the second user motion parameter.

Increasing Stride Compactness: Eliminate Unnecessary Motion (e.g., Vertical Displacement or Foot Motion) and Redirect Energy to Increasing Stride Rate while Maintaining Same Speed (Decrease Stride Length).

In one example, the first user motion parameter is a vertical displacement or foot motion and the second user motion parameter is a stride compactness.

In addition to wasting energy, the inventor has recognized that excessive vertical displacement is correlated to (i.e., limits) the compactness of the runner stride. Similarly, excessive foot motion is correlated to (i.e., limits) the compactness of the runner stride. Energy wasted can be re-directed toward increasing stride rate. Since less time is spent in the air, the runner is able to stride faster while maintaining the same speed. Thus, by identifying unnecessarily vertical displacement or foot motion, the system has identified a stride inefficiency which if corrected can allow the runner to improve their stride compactness.

Thus, recognizing this correlation, upon identifying unnecessary vertical displacement, the system both prompts the runner to decrease vertical displacement and increase stride rate while maintaining the same speed. Simply instructing the user to reduce-air time (or reduce vertical displacement) does not necessarily operate to improve the compactness of the stride because the runner does not naturally or automatically increase their stride rate or decrease their stride length for a given speed. The inventor has recognized this is an effective way to instruct the runner to increase their stride compactness. By eliminating the unnecessary vertical displacement, the runner can easily increase their stride rate while maintaining the same speed, thereby increasing stride compactness. Thus, the system advantageously informs the runner how to improve their stride compactness.

Thus, recognizing this correlation, upon identifying unnecessary foot motion, the system both prompts the runner to decrease foot motion (e.g., reduce the extent of rearward motion of the foot during striding) and increase stride rate while maintaining the same speed. Simply instructing the user to reduce-air time (or reduce foot motion) does not necessarily operate to improve the compactness of the stride because the runner does not naturally or automatically increase their stride rate or decrease their stride length for a given speed. The inventor has recognized this is an effective way to instruct the runner to increase their stride compactness. By eliminating the unnecessary foot motion, the runner can easily increase their stride rate while maintaining the same speed, thereby increasing stride compactness. Thus, the system advantageously informs the runner how to improve their stride compactness.

Eliminate Unnecessary Motion (e.g., Vertical Displacement or Foot Motion) and Redirect Energy to Increasing Stride Rate while Maintaining Same Stride Length (Increase Speed).

In one example, the first user motion parameter is a vertical displacement or foot motion and the second user motion parameter is a stride rate.

By eliminating unnecessarily vertical displacement and directing this energy in a horizontal direction and minimizing the time spent in the air, the runner is able to increase their stride rate while maintaining the same stride length. In other words, the runner is able to increase their speed (while consuming a comparable amount of energy) because energy is re-directed. Thus, recognizing this correlation, upon identifying unnecessary vertical displacement, the system both prompts the runner to decrease vertical displacement and increase their stride rate.

By eliminating unnecessarily foot motion and directing this energy in a horizontal direction and minimizing the time spent in the air, the runner is able to increase their stride rate while maintaining the same stride length. In other words, the runner is able to increase their speed (while consuming a comparable amount of energy) because energy is re-directed. Thus, recognizing this correlation, upon identifying unnecessary foot motion, the system both prompts the runner to decrease foot motion and increase their stride rate.

Eliminate Unnecessary Motion (e.g., Vertical Displacement or Foot Motion) and Redirect Energy to Increasing Stride Rate and Increase Stride Length (Increase Speed).

In one example, the first user motion parameter is a vertical displacement or foot motion and the second user motion parameter is a user speed.

By eliminating unnecessarily vertical displacement and directing this energy in a horizontal direction and minimizing the time spent in the air, the runner can both increase stride rate and stride length. Again, the runner is able to increase their speed (while consuming a comparable amount of energy).

By eliminating unnecessarily foot motion and directing this energy in a horizontal direction and minimizing the time spent in the air, the runner can both increase stride rate and stride length. Again, the runner is able to increase their speed (while consuming a comparable amount of energy).

Eliminate Unnecessary Motion (e.g., Vertical Displacement) and Redirect Energy to Increasing Stride Length while Maintaining Same Stride Rate (Increase Speed).

In one example, the first user motion parameter is a vertical displacement or foot motion and the second user motion parameter is a stride length.

By eliminating unnecessarily vertical displacement and directing this energy in a horizontal direction, the runner is able to increase their stride length while maintaining the same stride rate. In other words, the runner is able to increase their speed (while consuming the same amount of energy). Thus, recognizing this correlation, upon identifying unnecessary vertical displacement, the system both prompts the runner to decrease vertical displacement and increase their stride length.

By eliminating unnecessarily foot motion and directing this energy in a horizontal direction, the runner is able to increase their stride length while maintaining the same stride rate. In other words, the runner is able to increase their speed (while consuming the same amount of energy). Thus, recognizing this correlation, upon identifying unnecessary foot motion, the system both prompts the runner to decrease foot motion and increase their stride length.

Eliminate Unnecessary Motion (e.g., Vertical Displacement) and Redirect Energy to Increasing Endurance (Maintain Same Speed).

Furthermore, by eliminating the unnecessarily vertical displacement, the runner has the option of maintaining the same stride rate and same stride length (i.e., maintain the same speed), but do so with less expended energy, thereby allowing the runner to run for a longer period of time. This is particularly advantageous in ultra-distance style events.

In one example, a method for determining an improved user stride includes detecting a first user motion parameter in excess of a threshold value, determining a second user parameter, and identifying an improved user stride associated with both a decrease in the first user motion parameter and a maintenance of the second user motion parameter at an approximately same value.

In one example, the approximately same value is within five percent of a value prior to the decrease in the first user motion parameter.

In one example, the second user parameter is a motion parameter comprising a user speed.

In one example, the second user parameter is a physiological parameter comprising a user heart rate.

Advantageously, these methods and apparatuses provide a solution to the problem of how to instruct the user to improve the efficiency or compactness of their stride. Furthermore, these methods and apparatuses provide a solution to the problem of how to monitor the compactness of a user stride and determine whether the runner has improved the compactness of their stride.

Advantageously, these methods and apparatuses provide a solution to the problem of how to instruct the user to efficiently increase their speed, stride rate, or stride length. Furthermore, these methods and apparatuses provide a solution to the problem of how to monitor whether the user has efficiently increased their speed, stride rate, or stride length.

Figure 20:
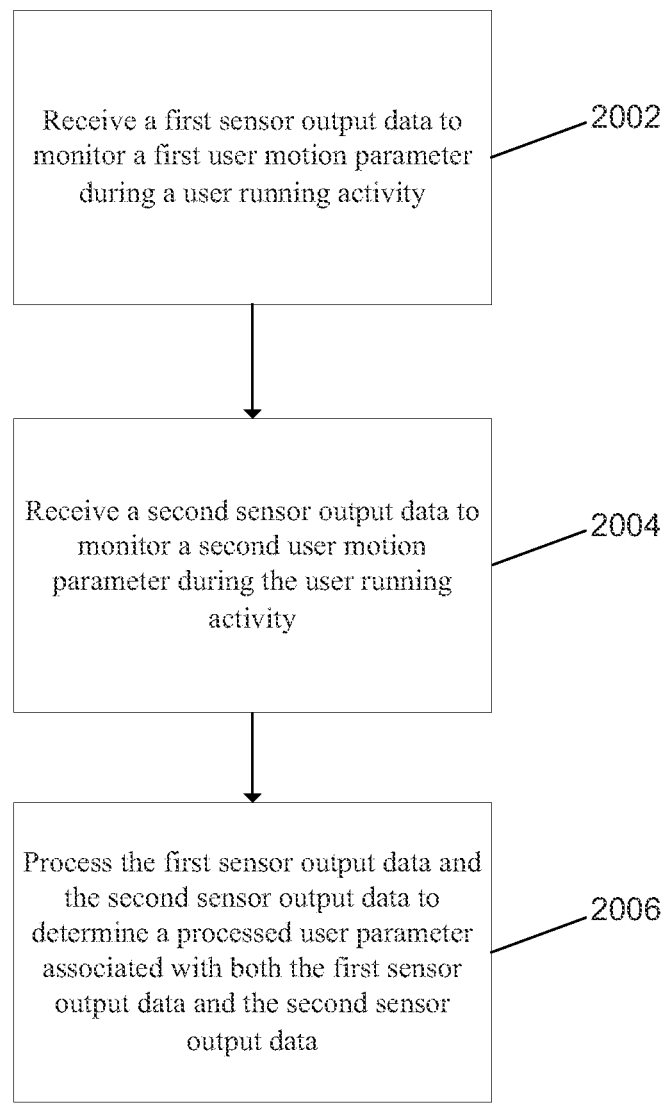
FIG. 20 is a flow diagram illustrating a method for monitoring a user running stride in one example.

FIG. 20 is a flow diagram illustrating a method for monitoring a user running stride in one example. At block 2002, a first sensor output data is received to monitor a first user motion parameter during a user running activity. At block 2004, a second sensor output data is received to monitor a second user motion parameter during the user running activity. At block 2006, the first sensor output data and the second sensor output data are processed to determine a processed user parameter associated with both the first sensor output data and the second sensor output data.

In one example, the first sensor output data is speed data, the second sensor output data is stride rate data, and the processed user parameter includes a user stride rate as a function of user speed. In one example, the processed user parameter includes an average stride rate for a same user speed, an average stride length for a same user speed, or an average time-in-the-air for a same user speed. In one example, the processed user parameter is an indicator of an efficiency of the runner stride. For example, the indicator of the efficiency of the runner stride is a measure of stride compactness.

Figure 21:
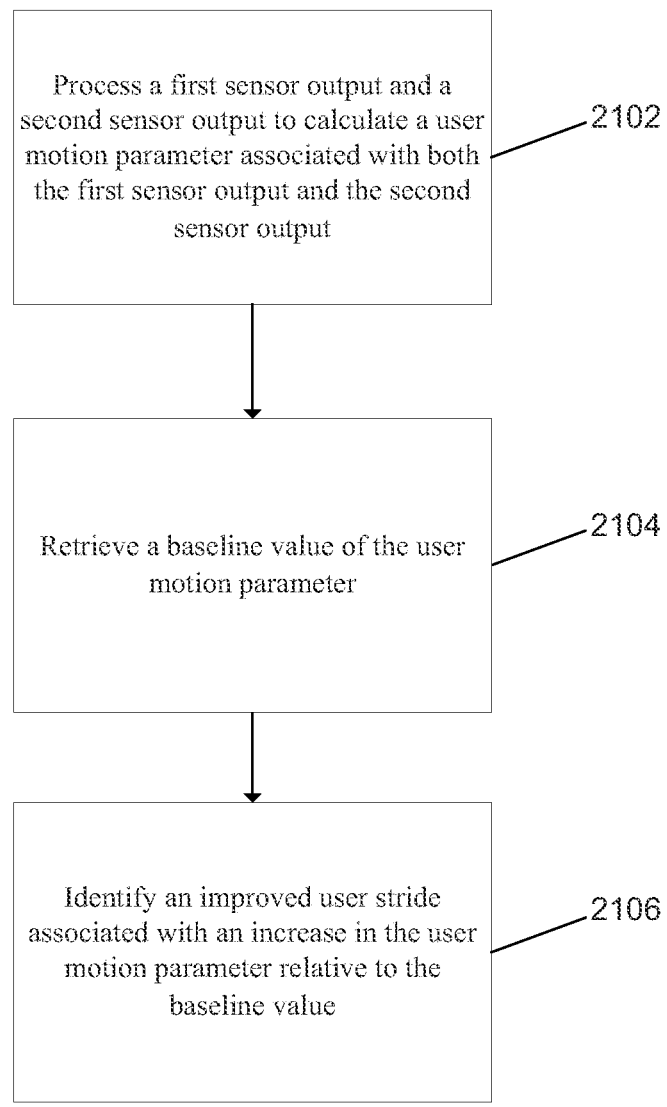
FIG. 21 is a flow diagram illustrating a method for determining an improved user stride in one example.

FIG. 21 is a flow diagram illustrating a method for determining an improved user stride in one example. At block 2102, a first sensor output and a second sensor output are processed to calculate a user motion parameter associated with both the first sensor output and the second sensor output. At block 2104, a baseline value of the user motion parameter is retrieved. At block 2106, an improved user stride associated with an increase in the user motion parameter relative to the baseline value is identified. In one example, the first sensor output is a speed sensor output, the second sensor output is a stride rate sensor, and the user motion parameter is a stride rate as a function of speed. In one example, the improved user stride is a stride with reduced overstride.

Figure 22:
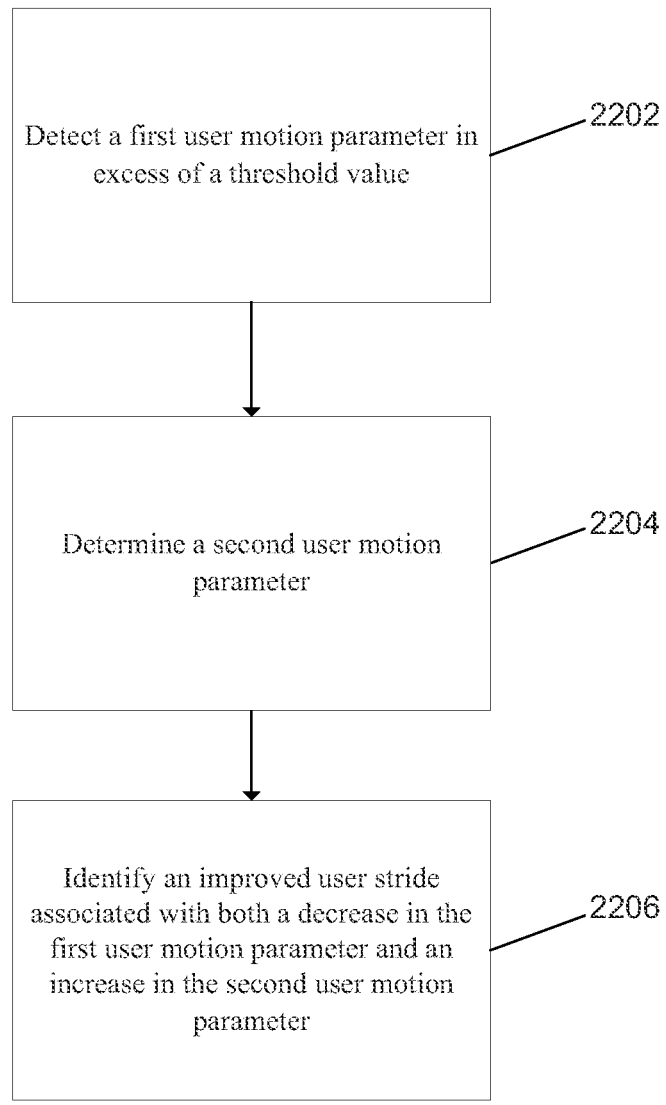
FIG. 22 is a flow diagram illustrating a method for determining an improved user stride in one example.

FIG. 22 is a flow diagram illustrating a method for determining an improved user stride in one example. At block 2202, a first user motion parameter in excess of a threshold value is detected. At block 2204, a second user motion parameter is determined (i.e., monitored). At block 2206, an improved user stride associated with both a decrease in the first user motion parameter and an increase in the second user motion parameter is identified.

In one example, the first user motion parameter includes a vertical displacement or a user foot motion. In one example, the second user motion parameter includes a user stride rate, a user stride length, a user speed, or a user stride compactness. In one example, the threshold value is dependent on a current user speed.

The method may further include prompting the user to decrease the first user motion parameter and increase the second user motion parameter following detecting the first user motion parameter in excess of the threshold value. Prompting the user may include outputting a text message at a wrist worn device or outputting an audible prompt at a head worn device or at the wrist worn device.

The method may further include monitoring a third user motion parameter, wherein identifying an improved user stride further includes identifying an increase in the third user motion parameter. For example, the third user motion parameter includes a user stride rate, a user stride length, a user speed, or a user stride compactness. The method may further include monitoring a user heart rate, wherein identifying an improved user stride further includes identifying the user heart rate to be approximately the same or less than a value prior measured prior to the decrease in the first user motion parameter and the increase in the second user motion parameter.

Figure 23:
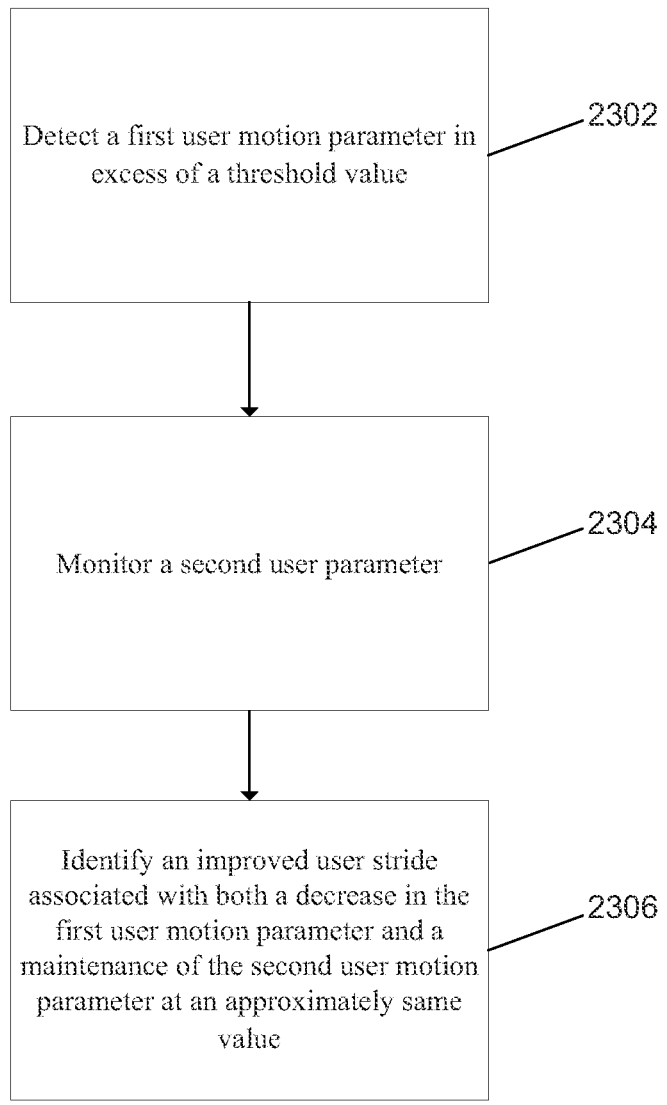
FIG. 23 is a flow diagram illustrating a method for determining an improved user stride in one example.

FIG. 23 is a flow diagram illustrating a method for determining an improved user stride in one example. At block 2302, a first user motion parameter in excess of a threshold value is detected. At block 2304, a second user parameter is monitored. In one example, the second user parameter is a motion parameter including a user speed. In one example, the second user parameter is a physiological parameter including a user heart rate.

At block 2306, an improved user stride associated with both a decrease in the first user motion parameter and a maintenance of the second user motion parameter at an approximately same value is identified. In one example, the approximately same value is within five percent of a value prior to the decrease in the first user motion parameter.

Figure 24:
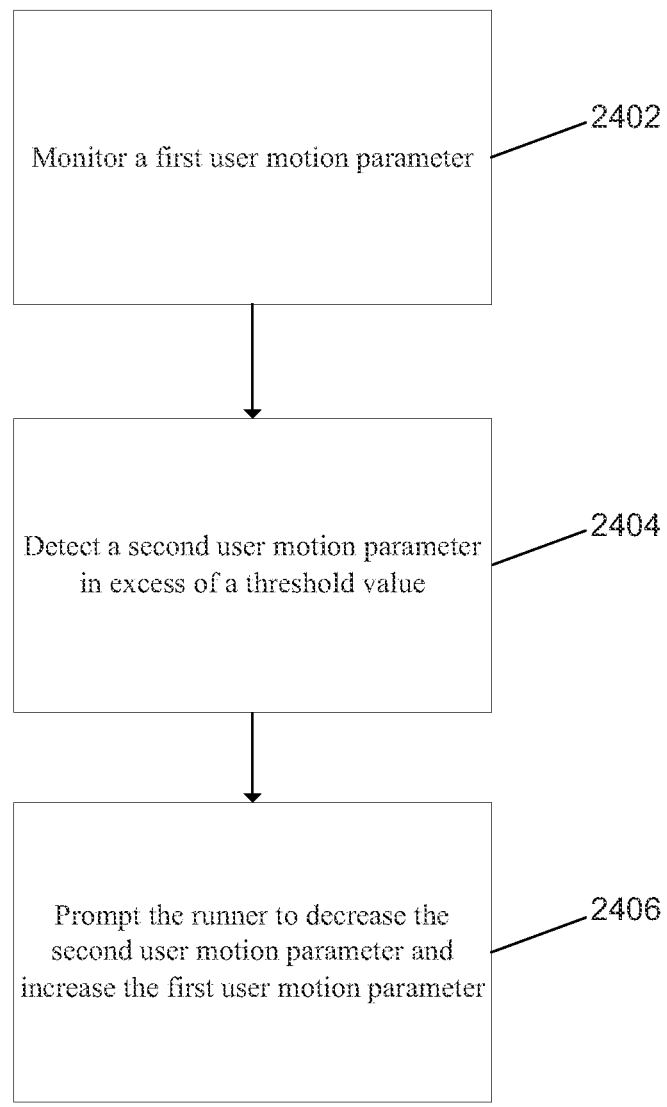
FIG. 24 is a flow diagram illustrating a method for instructing a runner in one example.

FIG. 24 is a flow diagram illustrating a method for instructing a runner in one example. At block 2402, a first user motion parameter is monitored. At block 2404, a second user motion parameter in excess of a threshold value is detected. At block 2406, the runner is prompted to decrease the second user motion parameter and increase the first user motion parameter. In one example, the first user motion parameter is a measure of stride of compactness, a runner stride rate, or a runner speed, and the second user motion parameter is a vertical displacement or foot motion.

Figure 25:
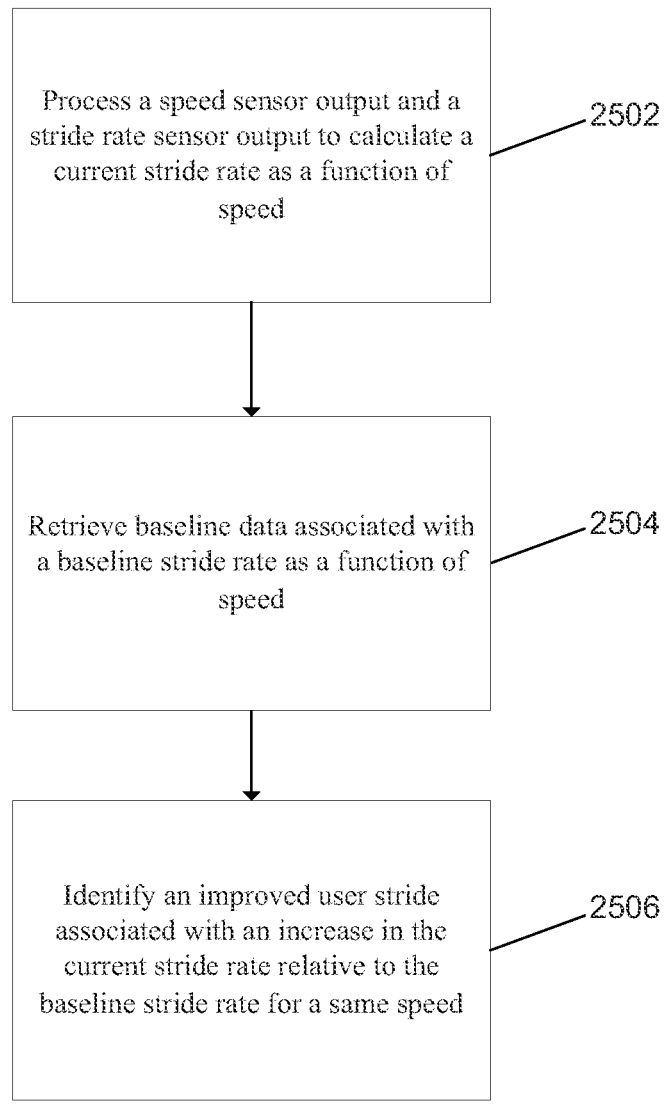
FIG. 25 is a flow diagram illustrating a method for determining an improved user stride in one example.

FIG. 25 is a flow diagram illustrating a method for determining an improved user stride in one example. At block 2502, a speed sensor output and a stride rate sensor output are processed to calculate a current stride rate as a function of speed. At block 2504, baseline data associated with a baseline stride rate as a function of speed is retrieved. At block 2506, an improved user stride associated with an increase in the current stride rate relative to the baseline stride rate for a same speed is identified.

Instructions of the various software/firmware applications performing methods and functionality discussed herein are loaded for execution on a corresponding control unit or processor. The control unit or processor may include a microcontroller, a microprocessor, a processor module, or subsystem including one or more microprocessors and microcontrollers, or other control or computing devices. The term controller refers to either software or hardware, or a combination of both, and may refer to multiple software or hardware modules.

While the exemplary embodiments of the present invention are described and illustrated herein, it will be appreciated that they are merely illustrative and that modifications can be made to these embodiments without departing from the spirit and scope of the invention. For example, methods, techniques, and apparatuses described as applying to one embodiment or example may also be utilized with other embodiments or examples described herein. Thus, the scope of the invention is intended to be defined only in terms of the following claims as may be amended, with each claim being expressly incorporated into this Description of Specific Embodiments as an embodiment of the invention.

What is claimed is:

1. A method comprising:
    determining a current user motion parameter from an output of a motion sensor in real-time during a user motion;
    tracking a current user speed in real-time during the user motion utilizing a global positioning system device mounted on a user body;
    outputting the user speed at a device user interface in real-time during the user motion;
    utilizing the global positioning system device in conjunction with the motion sensor to identify a current user stride efficiency utilizing both the current user motion parameter and the current user speed in real-time during the user motion;
    identifying a change in user stride efficiency in real-time during the user motion comprising receiving the current user motion parameter over an electronic data communications interface and receiving the current user speed, and determining from the current user motion parameter and the current user speed a change in the current user stride efficiency relative to a prior user stride efficiency occurring prior in time to the current user stride efficiency, the prior user stride efficiency identified utilizing a prior user motion parameter and a prior user speed; and
    providing the user real-time notice of the change in user stride efficiency comprising outputting an indication at a device user interface of the change in user stride efficiency in real-time during the user motion.

2. The method of claim 1, wherein the electronic data communications interface comprises a wireless communications link.

3. The method of claim 1, wherein the prior user speed and the current user speed satisfy a predetermined condition.

4. The method of claim 3, wherein the predetermined condition satisfied by the prior user speed and the current user speed is a same user speed.

5. The method of claim 1, wherein the change in user stride efficiency comprises an increased stride rate for a same user speed or a reduced stride rate for a same user speed.

6. The method of claim 1, wherein the current user motion parameter comprises a user stride rate.

7. The method of claim 1, wherein the current user motion parameter comprises a user stride length.

8. The method of claim 1, wherein the current user stride efficiency and the prior user stride efficiency are determined during a same run.

9. A system comprising:
one or more processors;
a wireless communications transceiver to receive a motion sensor data from a motion sensor;
a navigation system comprising a global positioning system (GPS) receiver or a cellular communications system to output a current user speed;
a user interface; and
one or more memories storing one or more application programs comprising instructions executable by the one or more processors configured to determine a current user motion parameter from the motion sensor data received on the wireless communications transceiver and receive the current user speed from the navigation system, the instructions further configured to identify from the current user motion parameter and the current user speed a change in a user stride efficiency relative to a prior user stride efficiency, the user stride efficiency identified utilizing the current user motion parameter and the current user speed.

10. The system of claim 9, wherein the prior user stride efficiency utilizes a prior user speed and a prior user motion parameter, and the prior user speed and the current user speed satisfy a predetermined condition.

11. The system of claim 10, wherein the predetermined condition satisfied by the prior user speed and the current user speed is a same user speed.

12. The system of claim 9, wherein the change in user stride efficiency comprises an increased stride rate for a same user speed or a reduced stride rate for a same user speed.

13. The system of claim 9, wherein the current user motion parameter comprises a user stride rate or a user stride length.

14. One or more non-transitory computer-readable storage media having computer-executable instructions stored thereon which, when executed by one or more processors, cause the one more processors to perform operations comprising:
determining a first user motion parameter from an output of a first motion sensor;
determining a second user motion parameter from an output of a second motion sensor;
identifying a change in a user stride comprising receiving the first user motion parameter over an electronic data communications interface and receiving the second user motion parameter, and determining from the first user motion parameter and the second user motion parameter a change in a user stride parameter relative to a prior user stride parameter, the user parameter identified utilizing the first motion parameter and the second motion parameter; and
outputting an indication at a device user interface of the change in the user stride.

15. The one or more non-transitory computer-readable storage media of claim 14, wherein the second user motion parameter comprises a user speed and the second motion sensor comprises a GPS receiver or a cellular device.

16. The one or more non-transitory computer-readable storage media of claim 14, wherein the user stride parameter comprises a user stride compactness and the prior user stride parameter comprises a prior user stride compactness.

17. The one or more non-transitory computer-readable storage media of claim 14, wherein the electronic data communications interface comprises a wireless communications link.

18. The one or more non-transitory computer-readable storage media of claim 14, wherein the first user motion parameter comprises a user stride rate and the second user motion parameter comprises a user speed, and wherein the change in the user stride comprises an increased stride rate for a same user speed or a reduced stride rate for a same user speed.

19. The one or more non-transitory computer-readable storage media of claim 14, wherein the first user motion parameter comprises a user stride rate or a user stride length and the second user motion parameter comprises a user speed.

20. One or more non-transitory computer-readable storage media having computer-executable instructions stored thereon which, when executed by one or more processors, cause the one more processors to perform operations comprising:
monitoring a user stride rate or a user stride length from a first electronic device output;
monitoring a user speed parameter from a second electronic device output;
outputting the user speed parameter at a device user interface;
determining a user stride parameter indicative of a user stride comprising the user stride rate and the user speed parameter, or the user stride length and the user speed parameter; and
outputting an indication at the device user interface of the user stride parameter.

21. The one or more non-transitory computer-readable storage media of claim 20, wherein the second electronic device output comprises output from a GPS receiver or a cellular device.

22. The one or more non-transitory computer-readable storage media of claim 20, wherein the user stride parameter comprises an average stride rate for a same speed.

23. The one or more non-transitory computer-readable storage media of claim 20, wherein the user stride parameter comprises an average stride length for a same speed.

24. The one or more non-transitory computer-readable storage media of claim 20, wherein the operations further comprising determining a second user stride parameter comprising an average time-in-the-air of a user body part for a same user speed.

25. The one or more non-transitory computer-readable storage media of claim 20, wherein outputting the indication at the device user interface of the user stride parameter comprises outputting a message of a user stride efficiency.

26. One or more non-transitory computer-readable storage media having computer-executable instructions stored thereon which, when executed by one or more processors, cause the one more processors to perform operations comprising:
- receiving on an electronic communications interface a user stride rate data or a user stride length data associated with a user athletic activity;
- receiving on an electronic communications interface a user speed data associated with the user athletic activity;
- outputting the user speed data at a device user interface;
- determining at an electronic device a user stride parameter indicative of a user stride comprising the user stride rate data and the user speed data, or the user stride length data and the user speed data; and
- outputting an indication at the device user interface of the user stride parameter.

27. The one or more non-transitory computer-readable storage media of claim 26, wherein the electronic device comprises a body-worn device including a GPS unit.

28. The one or more non-transitory computer-readable storage media of claim 26, wherein the user stride parameter comprises an average stride rate for a same speed.

29. The one or more non-transitory computer-readable storage media of claim 26, wherein the user stride parameter comprises an average stride length for a same speed.

30. The one or more non-transitory computer-readable storage media of claim 26, wherein the operations further comprising determining at the electronic device a second user stride parameter comprising an average time-in-the-air of a user body part for a same user speed.

31. The one or more non-transitory computer-readable storage media of claim 26, wherein outputting the indication at the device user interface of the user stride parameter comprises outputting a message of a user stride efficiency.

* * * * *